(12) United States Patent
Ulmer et al.

(10) Patent No.: US 8,165,823 B2
(45) Date of Patent: Apr. 24, 2012

(54) PAMPS, PATHOGEN ASSOCIATED MOLECULAR PATTERNS

(75) Inventors: Jeffrey Ulmer, Emeryville, CA (US); Nicholas Valiante, Emeryville, CA (US); Feng Xu, Emeryville, CA (US); Claudio Donati, Siena (IT); Antonello Covacci, Siena (IT)

(73) Assignee: Novartis AG, Basel (CH)

( * ) Notice: Subject to any disclaimer, the term of this patent is extended or adjusted under 35 U.S.C. 154(b) by 304 days.

(21) Appl. No.: 11/988,895

(22) PCT Filed: Jul. 15, 2006

(86) PCT No.: PCT/US2006/027484
§ 371 (c)(1),
(2), (4) Date: Jan. 15, 2008

(87) PCT Pub. No.: WO2007/011776
PCT Pub. Date: Jan. 25, 2007

(65) Prior Publication Data
US 2009/0155306 A1 Jun. 18, 2009

Related U.S. Application Data

(60) Provisional application No. 60/699,524, filed on Jul. 15, 2005.

(51) Int. Cl.
*G06F 19/00* (2011.01)
*G06F 17/30* (2006.01)

(52) U.S. Cl. .......................................... 702/20; 707/706

(58) Field of Classification Search ........................ None
See application file for complete search history.

(56) References Cited

U.S. PATENT DOCUMENTS

| | | | |
|---|---|---|---|
| 6,251,399 B1 | 6/2001 | Diamond | |
| 6,812,337 B1 | 11/2004 | St. George-Hyslop | |
| 6,841,155 B1 | 1/2005 | Del Giudice et al. | |
| 2003/0194695 A1 | 10/2003 | Johnston | |
| 2007/0274992 A1* | 11/2007 | Michalovich et al. | 424/139.1 |

FOREIGN PATENT DOCUMENTS

| | | |
|---|---|---|
| WO | 99/35260 A | 7/1999 |
| WO | 01/00857 A | 1/2001 |
| WO | 01/54720 A | 8/2001 |
| WO | WO-01/74130 | 10/2001 |
| WO | 02/46410 A | 6/2002 |
| WO | 03/047500 A | 6/2003 |
| WO | WO-2005/000780 | 1/2005 |

OTHER PUBLICATIONS

Hayashi et al. The innate immune response to bacterial flagellin is mediated by Toll-like receptor 5 Nature vol. 410, pp. 1099-1103 (2001).*
Marciani Vaccine adjuvants: role and mechanisms of action in vaccine immunogenicity. Drug Discovery Today vol. 8, pp. 934-943 (2003).*
Janssens et al. Role of Toll-Like Receptors in Pathogen Recognition. Clinical Microbiology Reviews vol. 16, pp. 637-646 (2003).*
Moingeon, P. et al. "Towards the rational design of Th1 adjuvants," Vaccine, vol. 19, No. 31, 2001, pp. 4363-4372.
Habermann et al., Molecular & Cellular Proteomics (2004) 3:238-249.
International Search Report for PCT/US06/27484, mailed on Apr. 4, 2007, 5 pages.
Lliev, Pathogen-associated Molecular Pattern (PAMP)-Modulated Gene Expression in monuclear phagocytes of rainbow trout (Oncorhynchus Mykiss) a dissertation, Notre Dame, Indiana, Jun. 2006.
Nevill-Manning et al., (1998) 95:5865-5871, Proc. Natl. Acad. Sci. USA.
Womble, Methods Mol. Biol. (2000) 132:3-22.

* cited by examiner

*Primary Examiner* — John S Brusca
(74) *Attorney, Agent, or Firm* — Helen Lee; Robert Gorman; Otis Littlefield

(57) ABSTRACT

A method for identifying a polypeptide which acts as an adjuvant in a host organism. The invention further provides adjuvant compositions comprising said polypeptides and optionally further comprising an antigen.

17 Claims, No Drawings

PAMPS, PATHOGEN ASSOCIATED MOLECULAR PATTERNS

CROSS REFERENCE TO RELATED APPLICATIONS

This application is a U.S. National Phase patent application of PCT/US2006/027484, filed Jul. 15, 2006, which claims priority to Provisional patent application Ser. No. 60/699,524 filed Jul. 15, 2005.

All documents cited herein are incorporated by reference in their entirety.

TECHNICAL FIELD

This invention is in the field of vaccine adjuvants.

BACKGROUND ART

Sub-unit vaccines often require the aid of an adjuvant to help boost immune activity. Chemical adjuvants such as aluminium salts and MF59™ have been approved for human use. However, aluminium salts are subject to safety concerns and are incompatible with some antigens. Furthermore, it produces a Th2 type of helper T cell response, which is often inappropriate or insufficient for protective immunity.

The best known adjuvant in laboratory use is Complete Freund's Adjuvant, which consists of killed *Mycobacterium tuberculosis* suspended in oil. Although this adjuvant is not suitable for human use due to its toxicity, safer adjuvants have been derived from other pathogenic organisms.

The immunostimulatory activity of materials derived from pathogens is believed to reflect the natural host-pathogen interaction. When the antigen-specific immune response evolved, it would have done so in an environment containing adjuvant-active bacterial components. The response to a pure bacterial antigen, injected without adjuvant-active bacterial components, is therefore an artificial situation to which the host would not be adapted to respond.

Components of pathogens are therefore believed to act as "danger signals", which put the immune system on alert. Examples of adjuvants in this category are components of bacterial capsules, LPS (lipopolysaccharides) from Gram negative bacteria, the glycolipids and arabinogalactans in mycobacteria and the peptidoglycans of spirochaetes. Other known adjuvants include DNA comprising unmethylated CpG dinucleotide motifs, which are relatively rare in vertebrate DNA compared to bacterial DNA, and double-stranded RNA, which mimics the presence of an invading virus.

Polypeptides from pathogens have not received much attention as potential adjuvants. One means to identify adjuvant-active polypeptide sequences from pathogens would be by high-throughput screening, but this approach is essentially random and undirected, such that effort will be wasted on screening polypeptides which are unlikely to function as adjuvants.

Many of the most widely used vaccines consist of whole organisms. These include live organisms that have been rendered safe by attenuating mutations (e.g. tuberculosis and rubella) and organisms killed or inactivated by chemical treatment (e.g. influenza and hepatitis A virus). That these types of vaccines are based on whole organisms presents both advantages and disadvantages. While having all of the components of the pathogen contained within the vaccine is useful for eliciting immune responses against multiple antigens that are structurally similar to those found on the infecting pathogen, some components of whole organism vaccines can cause undesirable side effects. Furthermore, live organism vaccines, although attenuated, can sometimes cause problems in immunosuppressed individuals and have the potential to revert to a virulent state. These disadvantages spurred a movement towards potentially safer, more defined vaccines consisting of partially purified subunits known to be targets for protective immune responses (e.g. tetanus toxoid and influenza haemagglutinin). With the advent of recombinant DNA technology came the ability to produce protein antigens in heterologous expression systems (e.g. hepatitis B surface antigen). In this way, high levels of protein can be manufactured, while eliminating contamination by toxic components of the pathogen. The progression from whole organisms to subunit vaccines has highlighted a need to augment these more purified vaccine components with adjuvants, as vaccines based on live attenuated organisms contain built-in adjuvants in the form of PAMPs. In contrast, subunit vaccines often lack these elements, thus requiring that they be added back.

There is thus a need for new adjuvants, particularly for human vaccines, and for methods for identifying them. It is an object of the invention to provide further and improved adjuvants for use in vaccines and also a directed method for identifying such adjuvants.

DISCLOSURE OF THE INVENTION

The invention is based on the identification of various pathogen-associated molecular patterns (PAMPs [refs. 1-6]) and the use of these patterns in identifying adjuvant-active polypeptides. Polypeptide PAMPs are motifs present in pathogenic polypeptides but rare or absent in the host organism's own polypeptides. Such motifs are commonly found in microbes but not in vertebrates. Thus, they are recognised as foreign by the host, resulting in the triggering of an appropriate immune response, which makes these polypeptide PAMPs ideal candidates for adjuvants in vaccines. Furthermore, because they are proteinaceous in nature, their amino acid sequence could be directly incorporated into the amino acid sequence of a protein antigen to increase potency.

Methods for Identifying Adjuvant-Active Polypeptides

The invention thus provides a method for identifying a polypeptide which acts as an adjuvant in a host organism comprising the steps of:
a) generating protein families by grouping together amino acid sequences from at least a different pathogenic organisms, which sequences share a BLAST alignment with an E-score less than $1E^{-05}$ (i.e. $1E^{-06}$, $1E^{-07}$, $1E^{-08}$, $1E^{-09}$, $1E^{-10}$, $1E^{-15}$, $1E^{-20}$ or less);
b) selecting a protein family of step a) wherein:
   (i) the family includes sequences from at least b different pathogenic organisms, and
   (ii) at least one of the proteins in the family does not share a BLAST alignment with an E-score smaller than $1E^{-05}$ (i.e. $1E^{-06}$, $1E^{-07}$, $1E^{-08}$, $1E^{-09}$, $1E^{-10}$, $1E^{-15}$, $1E^{-20}$ or smaller) with amino acid sequences from a chosen non-pathogenic organism;
c) determining the sequence motifs from the resulting families of step b) that are conserved within the family; and
d) selecting polypeptide sequences that comprise the motifs of step c), wherein: a is at least 60 (e.g. 62, 64, 66, 68, 70, 72, 74, 76, 78, 80, 82, 84, 86, 88, 90, 92, 94, 96, 98, 99 or more); and b is at least 30 (e.g. 32, 34, 36, 38, 40, 42, 44, 46, 48, 50, 52, 54, 56, 58, 60 or more), where b≦a.

Compared to random high throughput screening methods, the method of the invention is a more directed approach for identifying polypeptide adjuvants, as it takes into account that a host immune response is invoked against compounds considered to be foreign rather than compounds considered to be self. The method therefore selects polypeptide motifs that are present in pathogens but not in the host organism.

By "BLAST E score" we mean the E score achieved when amino acid sequences are aligned using BLAST P 2.2.1 from the Wisconsin GCG package version 10.3 [7].

"Pathogenic" or "pathogen" in the context of this invention refers to an organism that is capable of causing disease, for example, viruses and bacteria. Preferably, the pathogenic organism is a bacterium as most known pathogen-derived adjuvants are from bacteria.

"Non-pathogenic" in the context of this invention refers to an organism that is not capable of directly causing disease in a host organism. For example, a rat is considered to be non-pathogenic to a human even though the rat may be harbouring fleas which in turn carry the pathogen Yersinia pestis which can give rise to bubonic plague in a human host.

A "host organism" in the context of this invention refers to the organism being targeted by the pathogen. Preferably, the host organism is a human.

Step a)—Generating Protein Families

Step a) provides protein families from which the polypeptide adjuvant is derived. By starting with amino acid sequences derived from pathogenic organisms, however, rather than just random sequences, the method minimises the total number of sequences needed to be screened compared to random methods such as high throughput screening. Some of the protein families identified in this step will not be exclusive to pathogen genomes and will be excluded later on in the method. Preferably, the amino acid sequences used to generate the protein families of step a) are available from a genomic database, more preferably, a cDNA or expressed sequence database.

The most desirable immune response to be generated by an adjuvant is the innate host response, a response which is based on 'broad spectrum' mechanisms. Such 'broad spectrum' mechanisms, including but not limited to activation of complement via the alternative pathway, are known to be triggered by common microbial (i.e. pathogenic) components. Such microbial components have common amino acid sequences. Step a) therefore specifies that the organisms used to generate the protein families are pathogenic. At least a different pathogenic organisms are used for generating the families, and higher values of a give a higher probability that the protein families encode a common microbial component present in a large number of pathogens.

Step b)—Selecting a Protein Family

Having created a number of protein families, the method selects only those families which include sequences from at least b different pathogenic organisms, where b is equal to or less than a. This step excludes any protein family that does not encompass sequences from a large number of pathogenic organisms, as the objective of the method of this invention is to identify polypeptides that encode a common or conserved microbial component present in several pathogens. The closer the value of b is to a, the higher is the stringency of this step.

The second part of step b) is a filter to exclude those sequence motifs common to pathogenic and non-pathogenic organisms. Thus, only those families containing at least one sequence having no BLAST alignment over their full length with an E-score exceeding $1E^{-05}$ (i.e. $1E^{-05}$, $1E^{-06}$, $1E^{-07}$, $1E^{-08}$, $1E^{-09}$, $1E^{-10}$, $1E^{-15}$, $1E^{-20}$ or smaller) with a chosen non-pathogenic organism are selected for the next step. In most cases, this guarantees that all members of the selected family share a domain that is not present in the chosen non-pathogenic organism. By excluding protein families that include sequences common to both pathogens and non-pathogens, the probability that the selected protein family contains a PAMP is increased and therefore the probability of identifying a polypeptide which acts as an adjuvant is increased.

The non-pathogenic organism used in step b) may be the host organism (e.g. a human). However, it is preferably not a human, particularly when the method comprises a further step of selecting polypeptide sequences not present in the human genome (see below). A preferred non-pathogenic genome is a fly genome such as that of Drosophila melanogaster.

Step c)—Selecting a Polypeptide Sequence from the Selected Protein Family

Having selected a protein family that includes sequences common to a number of pathogenic organisms but not to a non-pathogenic organism, step c) identifies conserved sub-sequences or motifs within the selected protein family. These sub-sequences are tested for by means of their statistical relevance.

Preferably, a computer program is used for step c). Conserved patterns in protein sequences can be conveniently represented as a set of regular expressions, i.e. strings of symbols that, for each sequence position, specify the amino acid or list of amino acids that can occur in such a position. Efficient algorithms exist, both for the extraction of conserved motifs in the form of regular expressions from a set of related sequences, and for testing the occurrence of a given pattern in a set of sequences and will be well-known to a skilled artisan. More preferably, the PRATT program is used for step c) [8]. The PRATT program is able to discover patterns conserved in sets of unaligned protein sequences and can be found on-line at the website us.expasy.org under the directory /tools/pratt/.

FURTHER EMBODIMENTS OF THE PRESENT METHOD

Preferably, the sequences of step a) are derived from expressed or open reading frame (ORF) sequences. This is because the adjuvants of the present invention are based on expressed peptide sequences of pathogens.

Preferably, the host organism is a vertebrate, more preferably a mammal, most preferably a human.

In addition to the steps described above, the method may comprise the step of selecting those polypeptide sequences that are found, or predicted to be found, on the surface of, or are secreted by, a pathogenic cell. This is because in nature, the host immune system is more likely to initially encounter a secreted protein or surface protein of the pathogen rather than any intracellular component. This step therefore mimics the natural environment in this respect.

In a preferred embodiment, this step is carried out between steps b) and c) of the method. More preferably, only a protein family that included at least one amino acid sequence that is predicted, or has been annotated, as a surface or secreted protein is selected for use in step c).

Preferably, this step comprises inferring whether the polypeptide sequence is expressed on the surface or secreted by a pathogenic cell by making use of published annotation data. Such annotation data are generally available on public databases known to a skilled person including the NCBI databases available at the web site www.ncbi.nlm.nih.gov.

Alternatively, this step may comprise predicting whether the polypeptide sequence is expressed on the surface or secreted by a pathogenic cell by using an algorithm or program that provides accurate predictions of function. Such programs may make use of certain characteristics that are known to be shared by surface or secreted peptides such as a localisation signal. Usually, the localisation signal takes the form of a short peptide sequence. Often, but not always, this constitutes a signal sequence (or leader sequence). In the case of bacterial secreted proteins, most comprise leader sequences that are often of 15-40 amino acids in length (most commonly about 20), have a charged segment at the amino terminus, with one or two basic amino acids (e.g. lysine) followed by a stretch of hydrophobic amino acids, which usually includes two glycines or prolines, have a hydrophobic sequence followed by a stretch of about six amino acids that is thought to make a reverse turn in the chain.

An example of such a program is SignalP, a powerful tool for the detection of signal peptides and their cleavage sites [9] and available on-line at the website www.cbs.dtu.dk under the directory /services/SignalP/. Another example is PSORT, which annotates sequences as surface exposed or as surface, membrane or periplasm related and available at the website psort.nibb.ac.jp. Preferably, the PSORT program is used to predict whether the polypeptide sequence is expressed on the surface or secreted by a pathogenic cell.

The method may additionally comprise the step of selecting a polypeptide sequence from step b) or step c) that is not identical to an endogenous human amino acid sequence. Like step b) ii), this provides a filtering step to exclude those protein families or amino acid sequences within a protein family that are not exclusive to pathogenic organisms. This step therefore preferably excludes all patterns that encode at least one amino acid sequence present in the human genome.

In addition to those steps described above, the method may additionally comprise the further step of producing a polypeptide comprising or consisting of the sequence identified by the method of the present invention. Methods for producing such polypeptides are well known to a skilled person and are described in more detail below.

Adjuvant Polypeptides

The method of the invention reveals amino acid sequences suitable for use/testing as adjuvants. Therefore the invention provides a polypeptide comprising an amino acid sequence obtainable by the method described above. Because of their pathogen-specific nature, such polypeptides are ideal candidates for vaccine adjuvants. The immune stimulating properties of polypeptides are well known [e.g. see ref. 10]. Many known polypeptide adjuvants are modified with lipids or glycans (especially from bacteria, e.g. MDP), but unmodified peptide adjuvants have also been disclosed [17].

The invention provides polypeptides identified by methods of the invention. For instance, the invention provides a polypeptide comprising any one of the amino acid sequences listed in Table 3. The amino acid sequences in Table 3 are represented in PROSITE notation, with the amino acids being represented by their one-letter codes [11]. Briefly, a peptide comprising the following formula:

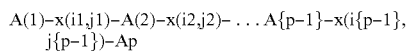

is to be interpreted in the following manner: A(k) is a component, either specifying one amino acid, e.g. C, or a set of amino acids, e.g. [ILVF]. A component A(k) is an identity component if it specifies exactly one amino acid (for instance C or L) or an ambiguous component if it specifies more than one (for instance [ILVF] or [FWY]). i(k), j(k) are integers so that i(k)<=j(k) for all k. The part x(ik,jk) specifies a wildcard region of the pattern matching between ik and jk arbitrary amino acids. A wildcard region x(ik,jk) is "flexible" if jk is bigger than ik (for example x(2,3)). The flexibility of such a region is jk−ik. For example the flexibility of x(2,3) is 1. The wildcard region is fixed if j(k) is equal to i(k), e.g., x(2,2) which can be written as x(2). The product of flexibility for a pattern is the product of the flexibilities of the flexible wildcard regions in the pattern, if any, otherwise it is defined to be one.

For example, C–x(2)–H is a pattern with two components (C and H) and one fixed wildcard region. It matches any sequence containing a C followed by any two arbitrary amino acids followed by an H. Amino acid sequences ChgHyw (SEQ ID NO: 1) and liChgHlyw (SEQ ID NO: 2) would be included in the formula. C–x(2,3)–H is a pattern with two components (C and H) and one flexible wildcard region. It matches any sequence containing a C followed by any two or three arbitrary amino acids followed by an H such as aaChgHywk (SEQ ID NO: 3) and liChgaHlyw (SEQ ID NO: 4). C–x(2,3)–[ILV] is a pattern with two components (C and [ILV]) and one flexible wildcard region. It matches any sequence containing a C followed by any two or three arbitrary amino acids followed by an I, L or V.

The invention also provides a polypeptide comprising an amino acid sequence having at least c % sequence identity to the amino acid sequences in Table 3 and/or comprising an amino acid sequence consisting of a fragment of at least x contiguous amino acids from an amino acid sequence of Table 3. Preferably the polypeptide has adjuvant activity e.g. in humans. The value of c is at least 85 e.g. 86, 87, 88, 89, 90, 91, 92, 93, 94, 95, 96, 97, 98, 99, 99.5, or more. The value of x is at least 5 e.g. 6, 7, 8, 9, 10, 11, 12, 13, 14, 15, 16, 17, 18, 19, 20, 21, 22, 23, 24, 25, 26, 27, 28, 29, 30, 35, 40, 45, 50. The fragment preferably retains adjuvant activity. Adjuvant activity can be assessed by measuring the immune response induced following co administration of antigen in the presence or absence of the test adjuvant. Adjuvants enhance the immune response against a co-administered antigen. Examples of such methods are described in references 12 and 13.

The invention also provides a polypeptide comprising an amino acid sequence listed in Table 3, except that the amino acid sequence contains one or more variations. The mutations may each independently be a substitution, an insertion, or a deletion. Preferably, the amino acid sequences contains fewer than twenty mutations (e.g. 19, 18, 17, 16, 15, 14, 13, 12, 11, 10, 9, 8, 7, 6, 5, 4, 3, 2 or 1). Each variation preferably involves a single amino acid. It is preferred that substitutions are conservative i.e. replacement of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity.

Polypeptides of the invention will be at least 3 (e.g. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more) amino acids in length. Polypeptides as short as 3 amino acids have been shown in the prior art to stimulate an immune response [14, 15, 16]. A 5-mer peptide (ALTTE) (SEQ ID NO: 5) from a bacterial fimbriae protein has also been shown to induce cytokine production from cells in vitro [17]. Although the over-riding factor that determines the length of the polypeptide is that it has to possess adjuvant activity, other factors may also contribute to the determination of the final length of the polypeptide. Such factors may include the expense involved in manufacturing said polypeptide, with shorter polypeptides being generally cheaper to synthesise.

Polypeptides of the invention may comprise fewer than 100 (e.g. 90, 80, 70, 60, 50, 45, 40, 35, 30, 25, 20, 19, 18, 17, 16, 15, 14, 13, 12, 11, 10, 9, 8, 7, 6, 5, 4) amino acids.

Also provided in this invention is a polypeptide comprising the formula $NH_2$-A-(B-C)$_n$-D-COOH, wherein: A is an optional N-terminal amino acid sequence; B is an adjuvant polypeptide sequence obtainable by the method of the invention (e.g. a sequence in Table 3); C is an optional amino acid linker sequence; D is an optional C-terminal amino acid sequence; and $n \geq 1$. Where $n>1$, each B and/or C may be the same or different in each of the n repetitions of B-C. Thus the polypeptide sequence A-($B_1$-$C_1$)-($B_2$-$C_2$)-D, where $B_1 \neq B_2$ and $C_1 \neq C_2$, still satisfies the formula A-(B-C)$_n$-D.

The/each sequence -B- may consist of fewer than 100 (e.g. 90, 80, 70, 60, 50, 45, 40, 35, 30, 25, 20, 19, 18, 17, 16, 15, 14, 13, 12, 11, 10, 9, 8, 7, 6, 5, 4) amino acids.

The sequences -A-, -C- and -D- may comprise a tag sequence to aid in purification, a sequence that confers higher protein stability, etc. The sequence(s) -C- may comprise a linker sequence (e.g. a poly-glycine linker). The optional N-terminal -A- may contain a secretory or leader sequence for directing protein trafficking. The/each sequence -A-, -C- and/ or -D- may consist of fewer than 100 (e.g. 90, 80, 70, 60, 50, 45, 40, 35, 30, 25, 20, 19, 18, 17, 16, 15, 14, 13, 12, 11, 10, 9, 8, 7, 6, 5, 4) amino acids.

When A and/or D sequences are present, these may be short (e.g. each $\leq$30 amino acids) or long (e.g. each longer than 30 amino acids). In the long form, A and/or D preferably comprises an immunogenic polypeptide sequence, thereby giving a fusion polypeptide including an antigen that makes use of the adjuvant sequence B. Having an antigen and adjuvant in the same polypeptide molecule simplifies production and purification, and enhancement of immunogenicity in this way has been shown using adjuvant portions of HSP [18].

Polypeptides of the invention can be prepared in any suitable manner e.g. by chemical synthesis (at least in part), by digesting longer polypeptides using proteases, by translation from RNA, by purification from cell culture (e.g. from recombinant expression), etc. The choice of how to prepare the polypeptide will depend on various factors. For short polypeptides, in vitro chemical synthesis [19, 20] will usually be the choice. Solid-phase peptide synthesis is particularly preferred, such as methods based on t-Boc or Fmoc [21] chemistry. Enzymatic synthesis [22] may also be used in part or in full.

For longer polypeptides, particularly those which include antigen and adjuvant within a single fusion polypeptide chain, biological synthesis will generally be the choice e.g. the polypeptides may be produced by translation. Translation may be carried out in vitro or in vivo.

In addition to their essential nature as polymers of amino acids, polypeptides of the invention may include modifications at various positions, including the peptide backbone, the amino acid side-chains and at the amino or carboxyl termini. Blockage of the amino and/or carboxyl terminus of a polypeptide by a covalent modification is common in naturally-occurring and synthetic polypeptides and such modifications may be present in polypeptides of the present invention. Similarly, modified amino acids (e.g. hydroxyproline, γ-carboxyglutamate, O-phosphoserine, homoserine, norleucine, methionine sulfoxide, methionine methyl sulfonium, N-formyl-methionine) may be present.

Polypeptides of the invention are generally provided in substantially pure form e.g. such that less than 50%, usually less than 60% and more usually less than 90% of the composition is made up of other polypeptide(s).

Polypeptides of the invention can be prepared in various forms (e.g. native, fusions, glycosylated, non-glycosylated, etc.). Polypeptides of the invention may be attached to a solid support. Polypeptides of the invention may comprise a detectable label (e.g. a radioactive or fluorescent label, or a biotin label).

The polypeptide of the invention is preferably not a full-length wild type polypeptide. It is preferably not an unmodified $NH_2$-ALTTE-COOH pentapeptide (SEQ ID NO: 5).

Peptidomimetics

Polypeptides of the invention are useful adjuvants in their own right. However, they may be refined to improve adjuvant activity (either general or specific) or to improve pharmacologically important features such as bio-availability, toxicology, metabolism, pharmacokinetics, etc. The polypeptides may therefore be used as lead compounds for further research and refinement.

Polypeptides of the invention can be used for designing peptidomimetic molecules [e.g. refs. 23 to 28] with adjuvant activity. These will typically be isosteric with respect to the polypeptides of the invention but will lack one or more of their peptide bonds. For example, the peptide backbone may be replaced by a non-peptide backbone while retaining important amino acid side chains.

The invention therefore provides a polymer comprising any one of the sequences listed in Table 3, wherein (a) the polymer comprises monomers selected from the group consisting of (but not limited to): L-amino acids; D-amino acids; and amino acid mimetics (such as those discussed in reference 29), and/or (b) the bonds between monomers are not peptide bonds. This polymer will not consist of a chain of L-amino acids joined by peptide bonds to form a linear unbranched polypeptide chain.

Different types of monomers (e.g. L- and D-amino acids) may be included in the same polymer, or the polymer may include a single type of monomer (e.g. all D-amino acids).

The polymer may include "peptoid" residues may be used. "Peptoids" result from the oligomeric assembly of N-substituted glycines [30]. Peptidomimetic compounds are advantageous because they omit classical peptide characteristics such as enzymatically scissille peptidic bonds. The polymer may comprise sugar amino acids [31].

Peptidomimetic compounds of the invention will generally be prepared by chemical synthetic routes, as biological methods are in general restricted to the production of polypeptides based on L-amino acids. However, manipulation of translation machinery (e.g. of aminoacyl-tRNA molecules) can be used to allow the introduction of D-amino acids (or of other non-natural amino acids, such as iodotyrosine or methylphenylalanine, azidohomoalanine, etc.) [32].

Nucleic Acid Molecules Encoding the Adjuvant Polypeptide Sequences and Related Products The invention provides nucleic acid comprising a nucleotide sequence which encodes a polypeptide of the invention.

The invention also provides nucleic acid which hybridises under high stringency conditions to a nucleic acid which encodes a polypeptide of the invention.

The invention also provides nucleic acid comprising a nucleotide sequence which has at least 75% identity (e.g. 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 100% identity) to a nucleotide sequence which encodes a polypeptide of the invention.

Further, the invention provides a vector, such as an expression vector, including such nucleic acids as plasmid DNA and recombinant viral and bacterial sequences.

The invention further provides a host cell transformed with a vector of the invention.

Medicaments and Immunogenic Compositions

The invention provides a composition comprising a polypeptide or polymer of the invention, and a pharmaceutically acceptable carrier.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolised macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Pharmaceutically acceptable salts can also be present in the pharmaceutical composition, e.g. mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in reference 33. Preferred medicaments are aqueous, buffered at pH 7.0±0.5, pyrogen-free and sterile.

In one embodiment, the invention provides a composition comprising microparticles and/or microemulsions and a polypeptide or polymer of the invention. Such microparticles and emulsions have been shown to potentiate the adjuvant activity of other known adjuvants [34-36].

Compositions of the invention are preferably immunogenic e.g. vaccines. Vaccines according to the invention may either be prophylactic (i.e. to prevent infection) or therapeutic (i.e. to treat disease after onset), but will typically be prophylactic. Therapeutic vaccines can also be used to treat non-infectious diseases such as cancer, allergy and asthma.

Immunogenic compositions used as vaccines comprise an immunologically effective amount of an antigen, as well as any other of the above-mentioned components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Compositions of the invention may be administered in conjunction with one or more antigens for use in therapeutic, prophylactic, or diagnostic methods of the present invention. Preferred antigens include those listed below. Additionally, the compositions of the present invention may be used to treat or prevent infections caused by any of the below-listed microbes.

In addition to combination with the antigens described below, the compositions of the invention may also be combined with an adjuvant as described herein. Antigens for use with the invention include, but are not limited to, one or more of the following antigens set forth below, or antigens derived from one or more of the pathogens set forth below:

A. Bacterial Antigens

Bacterial antigens suitable for use in the invention include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides*: Meningitides antigens may include proteins (such as those identified in References A-G), saccharides (including a polysaccharide, oligosaccharide or lipopolysaccharide), or outer-membrane vesicles (References H, I, J, K) purified or derived from *N. meningitides* serogroup A, C, W135, Y, and/or B. Meningitides protein antigens may be selected from adhesions, autotransporters, toxins, Fe acquisition proteins, and membrane associated proteins (preferably integral outer membrane protein).

*Streptococcus pneumoniae*: *Streptococcus pneumoniae* antigens may include a saccharide (including a polysaccharide or an oligosaccharide) or protein from *Streptococcus pneumoniae*. Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. No. 6,699,703, U.S. Pat. No. 6,800,744, WO 97/43303, and WO 97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis*: *Moraxella* antigens include antigens identified in WO 02/18595 and WO 99/58562, outer membrane protein antigens (HMW-OMP), C-antigen, and/or LPS.

*Bordetella pertussis*: Pertussis antigens include pertussis holotoxin (PT) and filamentous haemagglutinin (FHA) from *B. pertussis*, optionally also combination with pertactin and/or agglutinogens 2 and 3 antigen.

*Staphylococcus aureus*: Staph aureus antigens include *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis*: *S. epidermidis* antigens include slime-associated antigen (SAA).

Tetanus: Tetanus antigens include tetanus toxoid (TT), preferably used as a carrier protein in conjunction/conjugated with the compositions of the present invention.

Diphtheria: Diphtheria antigens include diphtheria toxin, preferably detoxified, such as $CRM_{197}$, additionally antigens capable of modulating, inhibiting or associated with ADP ribosylation are contemplated for combination/co-administration/conjugation with the compositions of the present invention, the diphtheria toxoids are preferably used as carrier proteins.

*Haemophilus influenzae* B (Hib): Hib antigens include a Hib saccharide antigen.

*Pseudomonas aeruginosa*: *Pseudomonas* antigens include endotoxin A, Wzz protein, *P. aeruginosa* LPS, more particularly LPS isolated from PAO1 (O5 serotype), and/or Outer Membrane Proteins, including Outer Membrane Proteins F (OprF) (*Infect Immun.* 2001 May; 69(5): 3510-3515).

*Legionella pneumophila* (Legionnaires' Disease): *L. pneumophila* antigens may optionally derived from cell lines with disrupted asd genes (*Infect Immun.* 1998 May; 66(5): 1898).

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, III, III, IV, V, VI, VII and VIII).

*Neiserria gonorrhoeae*: Gonorrhoeae antigens include Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al., J Infectious Disease (2000) 182:848-855), also see e.g. WO99/24578, WO99/36544, WO99/57280, WO02/079243).

*Chlamydia trachomatis*: *Chlamydia trachomatis* antigens include antigens derived from serotypes A, B, Ba and C are (agents of trachoma, a cause of blindness), serotypes $L_1$, $L_2$ & $L_3$ (associated with Lymphogranuloma venereum), and serotypes, D-K. *Chlamydia trachomas* antigens may also include an antigen identified in WO 00/37494, WO 03/049762, WO 03/068811, or WO 05/002619.

*Treponema pallidum* (Syphilis): Syphilis antigens include TmpA antigen.

*Haemophilus ducreyi* (causing chancroid): *Ducreyi* antigens include outer membrane protein (DsrA).

*Enterococcus faecalis* or *Enterococcus faecium*: Antigens include a trisaccharide repeat or other *Enterococcus* derived antigens provided in U.S. Pat. No. 6,756,361.

*Helicobacter pylori*: *H. pylori* antigens include Cag, Vac, Nap, HopX, HopY and/or urease antigen.

*Staphylococcus saprophyticus*: Antigens include the 160 kDa hemagglutinin of *S. saprophyticus* antigen.

*Yersinia enterocolitica* Antigens include LPS (*Infect Immun.* 2002 August; 70(8): 4414).

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which can share a common B-component known as protective antigen (PA).

*Yersinia pestis* (plague): Plague antigens include F1 capsular antigen (*Infect Immun.* 2003 January; 71(1)): 374-383, LPS (*Infect Immun.* 1999 October; 67(10): 5395), *Yersinia pestis* V antigen (*Infect Immun.* 1997 November; 65(11): 4476-4482).

*Mycobacterium tuberculosis*: Tuberculosis antigens include lipoproteins, LPS, BCG antigens, a fusion protein of antigen 85B (Ag85B) and/or ESAT-6 optionally formulated in cationic lipid vesicles (*Infect Immun.* 2004 October; 72(10): 6148), *Mycobacterium tuberculosis* (Mtb) isocitrate dehydrogenase associated antigens (*Proc Natl Acad Sci USA*. 2004 Aug. 24; 101(34): 12652), and/or MPT51 antigens (*Infect Immun.* 2004 July; 72(7): 3829).

*Rickettsia*: Antigens include outer membrane proteins, including the outer membrane protein A and/or B (OmpB) (*Biochim Biophys Acta*. 2004 Nov. 1; 1702(2):145), LPS, and surface protein antigen (SPA) (*J Autoimmun.* 1989 June; 2 Suppl:81).

*Listeria monocytogenes*: Antigens derived from *L. monocytogenes* are preferably used as carriers/vectors for intracytoplasmic delivery of conjugates/associated compositions of the present invention.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, O1 Inaba O-specific polysaccharides, *V. cholera* 0139, antigens of IEM108 vaccine (*Infect Immun.* 2003 October; 71 (10):5498-504), and/or Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, *Infect Immun.* 2001 May; 69(5): 3323-3334), VIsE Antigenic Variation Protein (*J Clin Microbiol.* 1999 December; 37(12): 3997).

*Porphyromonas gingivalis*: Antigens include *P. gingivalis* outer membrane protein (OMP).

*Klebsiella*: Antigens include an OMP, including OMP A, or a polysaccharide optionally conjugated to tetanus toxoid.

Where not specifically referenced, further bacterial antigens of the invention may be capsular antigens, polysaccharide antigens or protein antigens of any of the above. Further bacterial antigens may also include an outer membrane vesicle (OMV) preparation. Additionally, antigens include live, attenuated, split, and/or purified versions of any of the aforementioned bacteria. The bacterial or microbial derived antigens of the present invention may be gram-negative or gram-positive and aerobic or anaerobic.

Additionally, any of the above bacterial-derived saccharides (polysaccharides, LPS, LOS or oligosaccharides) can be conjugated to another agent or antigen, such as a carrier protein (for example $CRM_{197}$). Such conjugation may be direct conjugation effected by reductive amination of carbonyl moieties on the saccharide to amino groups on the protein, as provided in U.S. Pat. No. 5,360,897 and *Can J Biochem Cell Biol.* 1984 May; 62(5):270-5. Alternatively, the saccharides can be conjugated through a linker, such as, with succinamide or other linkages provided in *Bioconjugate Techniques,* 1996 and *CRC, Chemistry of Protein Conjugation and Cross-Linking,* 1993.

B. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens may be derived from viruses propagated on cell culture or expressed recombinantly. Viral antigens preferably include epitopes which are exposed on the surface of the virus during at least one stage of its life cycle. Viral antigens are preferably conserved across multiple serotypes. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Alternatively influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., *J Gen Virol.* 2004 November; 85(Pt 11):3229). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Hepamavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Hepamavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 or NSP-4. Togavirus antigens are preferably selected from E1, E2 or E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions (Houghton et al., *Hepatology* (1991) 14:381; See also WO92/08734).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens may be derived from Caliciviridae, such as Norwalk virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$.

Reovirus: Viral antigens may be derived from a Reovirus, such as an Orthoreovirus, a Rotavirus, an Orbivirus, or a Coltivirus. Reovirus antigens may be selected from structural proteins λ1, λ2, λ3, μ1, μ2, σ1, σ2, or σ3, or nonstructural proteins σNS, μNS, σ1s. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV): Viral antigens may be derived HDV, particularly δ-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins.

Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomavirus viruses include BK virus and JK virus. Polyomavirus antigens may be selected from VP1, VP2 or VP3.

Further provided are antigens, compositions, methods, and microbes included in *Vaccines*, 4$^{th}$ Edition (Plotkin and Orenstein ed. 2004); *Medical Microbiology* 4$^{th}$ Edition (Murray et al. ed. 2002); *Virology*, 3rd Edition (W. K. Joklik ed. 1988); *Fundamental Virology*, 2nd Edition (B. N. Fields and D. M. Knipe, eds. 1991), which are contemplated in conjunction with the compositions of the present invention.

Fungal Antigens

In some embodiments compositions of the present invention are combined with fungal antigens for use in methods of the present invention, including treatment or prevention of mycoses. Fungal antigens for use herein, associated with vaccines include those described in: U.S. Pat. Nos. 4,229,434 and 4,368,191 for prophylaxis and treatment of trichopytosis caused by *Trichophyton mentagrophytes*; U.S. Pat. Nos. 5,277,904 and 5,284,652 for a broad spectrum dermatophyte vaccine for the prophylaxis of dermatophyte infection in animals, such as guinea pigs, cats, rabbits, horses and lambs, these antigens comprises a suspension of killed *T. equinum, T. mentagrophytes* (var. *granulare*), *M. canis* and/or *M. gypseum* in an effective amount optionally combined with an adjuvant; U.S. Pat. Nos. 5,453,273 and 6,132,733 for a ringworm vaccine comprising an effective amount of a homogenized, formaldehyde-killed fungi, i.e., *Microsporum canis* culture in a carrier; U.S. Pat. No. 5,948,413 involving extracellular and intracellular proteins for pythiosis. Additional antigens identified within antifungal vaccines include Ringvac bovis LTF-130 and Bioveta.

Further, fungal antigens for use herein may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*.

Fungal pathogens for use as antigens or in derivation of antigens in conjunction with the compositions of the present invention comprise *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobo-*

*lus* spp., *Conidiobolus* spp., *Rhizopus* spp, *Mucor* spp, *Absidia* spp, *Mortierella* spp, *Cunninghamella* spp, and *Saksenaea* spp.

Other fungi from which antigens are derived include *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

STD Antigens

Embodiments of the invention include compositions and methods related to a prophylactic and therapeutic treatments for microbes that can be neutralized prior to infection of a cell. In particular embodiments, microbes (bacteria, viruses and/or fungi) against which the present compositions and methods can be implement include those that cause sexually transmitted diseases (STDs) and/or those that display on their surface an antigen that can be the target or antigen composition of the invention. In a preferred embodiment of the invention, compositions are combined with antigens derived from a viral or bacterial STD. Antigens derived from bacteria or viruses can be administered in conjunction with the compositions of the present invention to provide protection against at least one of the following STDs, among others: chlamydia, genital herpes, hepatitis (particularly HCV), genital warts, gonorrhoea, syphilis and/or chancroid (See, WO00/15255).

In another embodiment the compositions of the present invention are co-administered with an antigen for the prevention or treatment of an STD.

Antigens derived from the following viruses associated with STDs, which are described in greater detail above, are preferred for co-administration with the compositions of the present invention: hepatitis (particularly HCV), HPV, HIV, or HSV.

Additionally, antigens derived from the following bacteria associated with STDs, which are described in greater detail above, are preferred for co-administration with the compositions of the present invention: *Neiserria gonorrhoeae, Chlamydia pneumoniae, Chlamydia trachomatis, Treponema pallidum*, or *Haemophilus ducreyi*.

Respiratory Antigens

The invention provides methods of preventing and/or treating infection by a respiratory pathogen, including a virus, bacteria, or fungi such as respiratory syncytial virus (RSV), PIV, SARS virus, influenza, *Bacillus anthracis*, particularly by reducing or preventing infection and/or one or more symptoms of respiratory virus infection. A composition comprising an antigen described herein, such as one derived from a respiratory virus, bacteria or fungus is administered in conjunction with the compositions of the present invention to an individual which is at risk of being exposed to that particular respiratory microbe, has been exposed to a respiratory microbe or is infected with a respiratory virus, bacteria or fungus. The composition(s) of the present invention is/are preferably co-administered at the same time or in the same formulation with an antigen of the respiratory pathogen. Administration of the composition results in reduced incidence and/or severity of one or more symptoms of respiratory infection.

Tumor Antigens

One embodiment of the present involves a tumor antigen or cancer antigen in conjunction with the compositions of the present invention. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen. The tumor antigen can further be, for example, a polynucleotide-containing tumor antigen that expresses a polypeptide-containing tumor antigen, for instance, an RNA vector construct or a DNA vector construct, such as plasmid DNA.

Tumor antigens appropriate for the practice of the present invention encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

The tumor antigens can be, for example, (a) full length molecules associated with cancer cells, (b) homologs and modified forms of the same, including molecules with deleted, added and/or substituted portions, and (c) fragments of the same. Tumor antigens can be provided in recombinant form. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Additional tumor antigens which are known in the art include p15, Hom/Mel-40, H-Ras, E2A-PRL, H4-RET, IGH-IGK, MYL-RAR, Epstein Barr virus antigens, EBNA, human papillomavirus (HPV) antigens, Including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like. These as well as other cellular components are described for example in United States Patent Application 20020007173 and references cited therein.

Polynucleotide-containing antigens in accordance with the present invention typically comprise polynucleotides that encode polypeptide cancer antigens such as those listed above. Preferred polynucleotide-containing antigens include DNA or RNA vector constructs, such as plasmid vectors (e.g., pCMV), which are capable of expressing polypeptide cancer antigens in vivo.

Tumor antigens may be derived, for example, from mutated or altered cellular components. After alteration, the cellular components no longer perform their regulatory functions, and hence the cell may experience uncontrolled growth. Representative examples of altered cellular components include ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described for example in U.S. Pat. No. 5,693, 522 and references cited therein.

Additionally, bacterial and viral antigens, may be used in conjunction with the compositions of the present invention for the treatment of cancer. In particular, carrier proteins, such as CRM$_{197}$, tetanus toxoid, or *Salmonella typhimurium* antigen can be used in conjunction/conjugation with compounds of the present invention for treatment of cancer. The cancer antigen combination therapies will show increased efficacy and bioavailability as compared with existing therapies.

Additional information on cancer or tumor antigens can be found, for example, in Moingeon P, "Cancer vaccines," Vaccine, 2001, 19:1305-1326; Rosenberg S A, "Progress in human tumor immunology and Immunotherapy," Nature, 2001, 411:380-384; Dermine, S. et al, "Cancer Vaccines and Immunotherapy," British Medical Bulletin, 2002, 62, 149-162; Espinoza-Delgado I., "Cancer Vaccines," The Oncologist, 2002, 7(suppl3):20-33; Davis, I. D. et al., "Rational approaches to human cancer immunotherapy," Journal of Leukocyte Biology, 2003, 23: 3-29; Van den Eynde B, et al., "New tumor antigens recognized by T cells," Curr. Opin. Immunol., 1995, 7:674-81; Rosenberg S A, "Cancer vaccines based on the identification of genes encoding cancer regression antigens, Immunol. Today, 1997, 18:175-82; Offringa R et al., "Design and evaluation of antigen-specific vaccination strategies against cancer," Current Opin. Immunol., 2000, 2:576-582; Rosenberg S A, "A new era for cancer immunotherapy based on the genes that encode cancer antigens," Immunity, 1999, 10:281-7; Sahin U et al., "Serological identification of human tumor antigens," Curr. Opin. Immunol., 1997, 9:709-16; Old L J et al., "New paths in human cancer serology," J. Exp. Med., 1998, 187:1163-7; Chaux P, et al., "Identification of MAGE-3 epitopes presented by HLA-DR molecules to CD4(+) T lymphocytes," J. Exp. Med., 1999, 189:767-78; Gold P, et al., "Specific carcinoembryonic antigens of the human digestive system," J. Exp. Med., 1965, 122:467-8; Livingston P O, et al., Carbohydrate vaccines that induce antibodies against cancer: Rationale," Cancer Immunol. Immunother., 1997, 45:1-6; Livingston P O, et al., Carbohydrate vaccines that induce antibodies against cancer: Previous experience and future plans," Cancer Immunol. Immunother., 1997, 45:10-9; Taylor-Papadimitriou J, "Biology, biochemistry and immunology of carcinoma-associated mucins," Immunol. Today, 1997, 18:105-7; Zhao X-J et al., "GD2 oligosaccharide: target for cytotoxic T lymphocytes," J. Exp. Med., 1995, 182:67-74; Theobald M, et al., "Targeting p53 as a general tumor antigen," Proc. Natl. Acad. Sci. USA, 1995, 92:11993-7; Gaudernack G, "T cell responses against mutant ras: a basis for novel cancer vaccines," Immunotechnology, 1996, 2:3-9; WO 91/02062; U.S. Pat. No. 6,015,567; WO 01/08636; WO 96/30514; U.S. Pat. No. 5,846,538; and U.S. Pat. No. 5,869,445.

Pediatric/Geriatric Antigens

In one embodiment the compositions of the present invention are used in conjunction with an antigen for treatment of a pediatric population, as in a pediatric antigen. In a more particular embodiment the pediatric population is less than about 3 years old, or less than about 2 years, or less than about 1 years old. In another embodiment the pediatric antigen (in conjunction with the composition of the present invention) is administered multiple times over at least 1, 2, or 3 years.

In another embodiment the compositions of the present invention are used in conjunction with an antigen for treatment of a geriatric population, as in a geriatric antigen.

Other Antigens

Other antigens for use in conjunction with the compositions of the present include hospital acquired (nosocomial) associated antigens.

In another embodiment, parasitic antigens are contemplated in conjunction with the compositions of the present invention. Examples of parasitic antigens include those derived from organisms causing malaria and/or Lyme disease.

In another embodiment, the antigens in conjunction with the compositions of the present invention are associated with or effective against a mosquito born illness. In another embodiment, the antigens in conjunction with the compositions of the present invention are associated with or effective against encephalitis. In another embodiment the antigens in conjunction with the compositions of the present invention are associated with or effective against an infection of the nervous system.

In another embodiment, the antigens in conjunction with the compositions of the present invention are antigens transmissible through blood or body fluids.

Antigen Formulations

In other aspects of the invention, methods of producing microparticles having adsorbed antigens are provided. The methods comprise: (a) providing an emulsion by dispersing a mixture comprising (i) water, (ii) a detergent, (iii) an organic solvent, and (iv) a biodegradable polymer selected from the group consisting of a poly($\alpha$-hydroxy acid), a polyhydroxy butyric acid, a polycaprolactone, a polyorthoester, a polyanhydride, and a polycyanoacrylate. The polymer is typically present in the mixture at a concentration of about 1% to about 30% relative to the organic solvent, while the detergent is typically present in the mixture at a weight-to-weight detergent-to-polymer ratio of from about 0.00001:1 to about 0.1:1 (more typically about 0.0001:1 to about 0.1:1, about 0.001:1 to about 0.1:1, or about 0.005:1 to about 0.1:1); (b) removing the organic solvent from the emulsion; and (c) adsorbing an antigen on the surface of the microparticles. In certain embodiments, the biodegradable polymer is present at a concentration of about 3% to about 10% relative to the organic solvent.

Microparticles for use herein will be formed from materials that are sterilizable, non-toxic and biodegradable. Such materials include, without limitation, poly($\alpha$-hydroxy acid), polyhydroxybutyric acid, polycaprolactone, polyorthoester, polyanhydride, PACA, and polycyanoacrylate. Preferably, microparticles for use with the present invention are derived from a poly($\alpha$-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

Further antigens may also include an outer membrane vesicle (OMV) preparation.

Additional formulation methods and antigens (especially tumor antigens) are provided in U.S. patent Ser. No. 09/581,772.

Antigen References

The following references include antigens useful in conjunction with the compositions of the present invention:
A. International patent application WO99/24578
B. International patent application WO99/36544.
C. International patent application WO99/57280.
D. International patent application WO00/22430.
E. Tettelin et al. (2000) Science 287:1809-1815.
F. International patent application WO96/29412.
G. Pizza et al. (2000) Science 287:1816-1820.
H. PCT WO 01/52885.
I. Bjune et al. (1991) Lancet 338(8775).
J. Fuskasawa et al. (1999) Vaccine 17:2951-2958.
K. Rosenqist et al. (1998) Dev. Biol. Strand 92:323-333.
Constantino et al. (1992) Vaccine 10:691-698.
Constantino et al. (1999) Vaccine 17:1251-1263.
Watson (2000) Pediatr Infect Dis J 19:331-332.
Rubin (20000) Pediatr Clin North Am 47:269-285, v.
Jedrzejas (2001) Microbiol Mol Biol Rev 65:187-207.
International patent application filed on 3 Jul. 2001 claiming priority from GB-0016363.4; WO 02/02606; PCT IB/01/00166.
Kalman et al. (1999) Nature Genetics 21:385-389.
Read et al. (2000) Nucleic Acids Res 28:1397-406.
Shirai et al. (2000) J. Infect. Dis 181(Suppl 3):S524-S527.
International patent application WO99/27105.
International patent application WO00/27994.
International patent application WO00/37494.
International patent application WO99/28475.
Bell (2000) Pediatr Infect Dis J 19:1187-1188.
Iwarson (1995) APMIS 103:321-326.
Gerlich et al. (1990) Vaccine 8 Suppl:S63-68 & 79-80.
Hsu et al. (1999) Clin Liver Dis 3:901-915.
Gastofsson et al. (1996) N. Engl. J. Med. 334:349-355.
Rappuoli et al. (1991) TIBTECH 9:232-238.
Vaccines (1988) eds. Plotkin & Mortimer. ISBN 0-7216-1946-0.
Del Guidice et al. (1998) Molecular Aspects of Medicine 19:1-70.
International patent application WO93/018150.
International patent application WO99/53310.
International patent application WO98/04702.
Ross et al. (2001) Vaccine 19:135-142.
Sutter et al. (2000) Pediatr Clin North Am 47:287-308.
Zimmerman & Spann (1999) Am Fan Physician 59:113-118, 125-126.
Dreensen (1997) Vaccine 15 Suppl" S2-6.
MMWR Morb Mortal Wkly rep 1998 January 16:47(1):12, 9.
McMichael (2000) Vaccine 19 Suppl 1:S101-107.
Schuchat (1999) Lancer 353(9146):51-6.
GB patent applications 0026333.5, 0028727.6 & 0105640.7.
Dale (1999) Infect Disclin North Am 13:227-43, viii.
Ferretti et al. (2001) PNAS USA 98: 4658-4663.
Kuroda et al. (2001) Lancet 357(9264):1225-1240; see also pages 1218-1219.
Ramsay et al. (2001) Lancet 357(9251):195-196.
Lindberg (1999) Vaccine 17 Suppl 2:S28-36.
Buttery & Moxon (2000) J R Coil Physicians Long 34:163-168.
Ahmad & Chapnick (1999) Infect Dis Clin North Am 13:113-133, vii.
Goldblatt (1998) J. Med. Microbiol. 47:663-567.
European patent 0 477 508.
U.S. Pat. No. 5,306,492.
International patent application WO98/42721.
Conjugate Vaccines (eds. Cruse et al.) ISBN 3805549326, particularly vol. 10:48-114.
Hermanson (1996) Bioconjugate Techniques ISBN: 012323368 & 012342335X.
European patent application 0372501.
European patent application 0378881.
European patent application 0427347.
International patent application WO93/17712.
International patent application WO98/58668.
European patent application 0471177.
International patent application WO00/56360.
International patent application WO00/67161.

Compositions of the invention may be formulated for administration by mucosal or parenteral routes, including intravenous, intramuscular, intraperitoneal, subcutaneous, transdermal, airway (aerosol), oral, intranasal, rectal, vaginal and topical (including buccal and sublingual) administration. Thus the compositions may be prepared in injectable form.

Methods of Treatment

The invention provides a method of raising an immune response in a patient, comprising administering a patient with a composition of the invention. The composition may be administered intravenously, intramuscularly, intraperitoneally, subcutaneously, transdermally, orally, intranasally, rectally, vaginally or topically. The immune response is preferably protective.

The invention also provides the use of a polypeptide or polymer of the invention in the manufacture of a medicament for immunising a patient. The invention also provides a polypeptide or polymer of the invention for use in medicine.

Medicaments may be administered by mucosal or parenteral routes, including intravenous, intramuscular, intraperitoneal, subcutaneous, transdermal, airway (aerosol), oral, intranasal, rectal, vaginal and topical (including buccal and sublingual) administration. Intramuscular administration to the thigh or the upper arm is preferred. Injection may be via a needle (e.g. a hypodermic needle), but needle-free injection may alternatively be used.

Administration may be a single dose schedule or a multiple dose schedule. A primary dose schedule may be followed by a booster dose schedule. Suitable timing between priming and boosting can be routinely determined.

Administration will generally be to an animal and, in particular, human subjects can be treated. The compositions are particularly useful for vaccinating children and teenagers.

Certain bacterial proteins (e.g., flagellin, fimbriae, HSP) are known, or thought, to signal to the innate immune system through toll-like receptors (TLRs) [37, 38], and this may be mediated through linear peptide sequences (e.g., ALTTE in fimbriae). Thus, another aspect of the present invention is the use of a polypeptide of the invention as an agonist or antagonist of a toll-like receptor or a related receptor of the innate immune system. The term "agonist" refers to a substance that has affinity for and stimulates physiological activity at a cell receptor normally stimulated by naturally occurring substances, thus triggering a biochemical response. Assays for TLR agonism are known [e.g. 39]. One indicator of activity of a TLR agonist is the production of cytokines from one or more cells of the immune system, such as antigen presenting cells, lymphocytes or macrophages. The term "antagonist" refers to a substance that nullifies the action of another, such as a drug binding to a cell receptor without eliciting a biological response. Antagonists are sometimes referred to as inhibitors. Assays for TLR agonism are known [e.g. 40].

DEFINITIONS

The term "comprising" can mean "including" as well as "consisting" e.g. a composition "comprising" X may consist exclusively of X or may include something additional e.g. X+Y.

As well as being adjuvants, it would be understood by a skilled person that the polypeptides of the present invention may also be useful in immune-based therapies for cancer or infectious diseases, and immunomodulatory agents for autoimmune diseases such as allergies and asthma.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 41. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 42.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 41. A preferred alignment program is GCG Gap (Genetics Computer Group, Wisconsin, Suite Version 10.1), preferably using default parameters, which are as follows: open gap=3; extend gap=1.

MODES FOR CARRYING OUT THE INVENTION

1. Generation of Protein Families

A database consisting of 60 complete bacterial genomes (see Table 1 below) was found to comprise 148251 open reading frames (ORFs). The polypeptides encoded by these 148251 ORFs were grouped together into protein families according to their sequence identity. The BLAST program from the GCG program suite was used, using the BLOSUM62 substitution matrix and default parameters to identify all pairs of proteins sharing an alignment with an E-score smaller than $1.0E^{-05}$. The BLAST E-score is the probability that an alignment of better quality, as measured by the alignment score, is found by chance in the same data set. The protein dataset was then partitioned into non-overlapping families, which include only proteins that share an alignment with an E-score smaller than $1.0E^{-05}$ with all other members of the same family.

2. Selecting a Protein Family that Comprises a PAMP

In order to identify only those protein families containing PAMPs, which by definition are motifs that are exclusive to pathogens (and not present in the host human), only those protein families that did not contain proteins from the *Drosophila* genome were chosen. This means that at least one of the proteins in the family had no BLAST alignment with any protein in the *Drosophila* genome with an E-score smaller than the threshold of $1.0E^{-05}$. Although the *Drosophila* is not the host organism for the present example, a pathogenic protein family sequence that shares a high identity with a *Drosophila* (i.e. non-pathogenic) protein sequence has an increased probability of sharing a high identity with a human sequence.

3. Predicting the Cellular Localisation of the Protein Families

Protein families that encode a secreted protein or surface protein of a pathogen are preferred. Only those protein families that contained at least one amino acid sequence which was either already annotated as encoding a surface related protein or was predicted as being a protein that is localised on the cell surface by PSORT were kept. 251 protein families were identified at this stage.

4. Identifying a Conserved Polypeptide Sequence from within the Protein Family

Of the families that passed the previous selections, a list of conserved polypeptide sequences from within the protein family sequences were identified. The list was compiled with the aid of the PRATT algorithm. The following default parameters were used, i.e. i) pattern conserved in 100% of the sequences, ii) max length: 50, iii) max number of consecutive x's is 5, iv) max number of flexible spacers is 2, v) max flexibility is 2 and vi) mac flexible product is 10. The patterns were ranked using PRATT as specified in [8]. For each protein family, only the top 10 scoring patterns were retained. PRATT analysis of the 251 families yielded a list of over 2500 polypeptide sequences.

5. Excluding Pathogenic Polypeptide Sequences that are also Present in the Human Genome Using the list of over 2500 polypeptide sequences in the EMBOSS [43] software suite, a pattern search was carried out on the published human genome sequence. EMBOSS was able to test whether any of the over 2500 polypeptide sequences shared a high identity with any human polypeptide sequences. Using fuzzpro, which is part of the EMBOSS suite, a search was run for each pattern against the complete set of human proteins. Those patterns having at least one hit in the human genome were discarded. This last selection step yielded a list of 312 polypeptide sequences, which are listed in Table 3.

6. Confirmation of Adjuvant Activity

To evaluate adjuvant activity of the putative peptide PAMPs listed in Table 2, a set of peptides relating to the bacterial signature sequence PDCG-[LM]-[KR] were synthesised, purified and demonstrated to be free of endotoxin. The possible combinations of sequences included PDCGLR, PDCGLK, PDCGMR, and PDCGMK. The human monocytic cell line THP-1 was incubated with each of the peptides and adjuvant activity was observed for the peptide PDCGLR, as measured by the specific production of cytokines (IL1-β, IL-8 and TNFα). This peptide was further evaluated on primary human peripheral blood mononuclear cells (hPBMC), where cytokine production (IL-6 and TNFα) was also demonstrated. Therefore, the specific peptide sequence PDCGLR, which was identified as a bacterial signature found commonly in bacterial proteins but not in *Drosophila*, is recognised by the human immune system as a PAMP.

For the assay, the human cells used were cultured at 1 million cells/ml in 96-well plates with the peptides in complete RPMI medium with 5% FBS. After culture for 18 hours at 37° C. and 5% CO$_2$, the culture supernatants were measured for the cytokines generated by the cells with an Upstate multiplex cytokine kit. The peptide solutions made in PBS buffer were found to have <0.01 U/ml endotoxin, and this level of endotoxin can not stimulate the immune cells used to secrete detectable cytokines.

It will be understood that the invention has been described by way of example only and modifications may be made whilst remaining within the scope and spirit of the invention.

TABLE 1

*Aeropyrum pernix*
*Aquifex aeolicus*
*Archaeoglobus fulgidus*
*Bacillus halodurans*
*Bacillus subtilis*
*Borrelia burgdorferi*
*Buchnera* sp. APS
*Campylobacter jejuni*
*Caulobacter crescentus*
*Chlamydia muridarum*
*Chlamydia trachomatis*
*Chlamydophila pneumoniae*
*Chlamydophila pneumoniae* AR39
*Chlamydophila pneumoniae* CWL029
*Clostridium acetobutylicum*
*Deinococcus radiodurans*
*Escherichia coli*
*Escherichia coli* O157:H7
*Haemophilus influenzae* Rd
*Halobacterium* sp. NRC-1
*Helicobacter pylori* 26695
*Helicobacter pylori* J99

TABLE 1-continued

*Lactococcus lactis* subsp. *Lactis*
*Listeria innocua*
*Listeria monocytogenes* EGD-e
*Mesorhizobium loti*
*Methanobacterium thermoautotrophicum*
*Methanococcus jannaschii*
*Mycobacterium leprae*
*Mycobacterium tuberculosis* CDC1551
*Mycoplasma genitalium*
*Mycoplasma pneumoniae*
*Mycoplasma pulmonis*
*Neisseria meningitidis*
*Neisseria meningitidis* Z2491
*Pasteurella multocida*
*Pseudomonas aeruginosa*
*Pyrococcus abyssi*
*Pyrococcus horikoshii*
*Ralstonia solanacearum*
*Rickettsia conorii*
*Rickettsia prowazekii*
*Salmonella enterica* subsp. *Enterica* serovar *Typhi*
*Salmonella typhimurium* LT2
*Sinorhizobium meliloti*
*Staphylococcus aureus*
*Staphylococcus aureus* subsp. *Aureus* Mu50
*Staphylococcus aureus* subsp. *Aureus* N315
*Streptococcus pneumoniae*
*Streptococcus pyogenes*
*Sulfolobus solfataricus*
*Sulfolobus tokodaii*
*Synechocystis* PCC6803
*Thermoplasma acidophilum*
*Thermoplasma volcanium*
*Thermotoga maritima*
*Treponema pallidum*
*Ureaplasma urealyticum*
*Vibrio cholerae*
*Xylella fastidiosa*

TABLE 2

Cytokine production (pg/ml) by human cells after peptide stimulation

| Peptide | hPBMC #1643 | | THP-1 | | |
|---|---|---|---|---|---|
| | IL-6 | TNF-α | IL-1β | IL-8 | TNF-α |
| PDCGLR (SEQ ID NO: 6) | 31.42 | 3.6 | 11.32 | 171.11 | 4.42 |
| PDCGLK (SEQ ID NO: 7) | ND | ND | 1.33 | 24.29 | <1 |
| PDCGMR (SEQ ID NO: 8) | ND | ND | 1.61 | 25.71 | <1 |
| PDCGMK (SEQ ID NO: 9) | ND | ND | 1.59 | 19.28 | <1 |
| Cell only (control) | 8.31 | <1 | 1.53 | 21.47 | <1 |

Note:
ND, not determined.

TABLE 3

312 pathogenic adjuvant polypeptide sequences identified using the method of the invention

| | |
|---|---|
| G-[FY]-x(2)-R-x(2)-[ST]-x(2)-G-[QR]-x-[ILV]-[ILV]-x(2)-R-R-x-[HKR]-[GNQ]-R-x(2)-L | (SEQ ID NO: 10) |
| H-E-x-[AG]-H-x(3)-[AG]-x(4)-[IMV]-x(4)-[FY]-x-[ILV]-G-[FIM]-G-x(2)-[FIL] | (SEQ ID NO: 11) |
| H-E-x(2)-H-x(3)-[AG]-x(4)-[IMV]-x(4)-[FY]-x-[ILV]-G-[FIM]-G-x(2)-[FIL] | (SEQ ID NO: 12) |

TABLE 3-continued 312 pathogenic adjuvant polypeptide sequences identified using the method of the invention

| Sequence | SEQ ID NO |
|---|---|
| G-[ILMV]-x-L-x-G-x-E-[IV]-x-[AS]-[ILMV] | 13 |
| D-[DEGNQS]-x-[DEG]-x-D-x-K-[ILV]-[ILV]-[ACG]-[LV]-x(3)-[DHK] | 14 |
| G-G-x-S-x-E-[HR]-x-[IV]-S-x(2)-[ST]-[AGS] | 15 |
| G-x-S-x-E-[HR]-x-[IV]-S-x(2)-[ST]-[AGS] | 16 |
| H-G-x(2)-G-x(0,2)-E-[DT]-G-x-[ILMV]-x-[AGS] | 17 |
| V-x(3)-[ASV]-x-K-x(2)-[AILV]-x(2)-A-[IMV]-x(2)-[AILV]-F-x(1,2)-V-x(1,2)-V | 18 |
| K-x(2)-[AILV]-x(2)-A-[IMV]-x(2)-[AILV]-F-x(1,2)-V-x(1,2)-V | 19 |
| A-x(3)-G-x(2)-E-x-[DNP]-x(3)-D-[ILV]-x-[AG]-x-D-x(3)-K-x(2)-[ILV] | 20 |
| A-x(3)-G-x(2)-E-x(5)-D-[ILV]-x-[AG]-x-D-x(3)-K-x(2)-[ILV] | 21 |
| G-x(2)-E-x-[DNP]-x(3)-D-[ILV]-x-[AG]-x-D-x(3)-K-x(2)-[ILV] | 22 |
| G-x(2)-E-x(5)-D-[ILV]-x-[AG]-x-D-x(3)-K-x(2)-[ILV] | 23 |
| E-x-[DNP]-x(3)-D-[ILV]-x-[AG]-x-D-x(3)-K-x(2)-[ILV] | 24 |
| Q-[FILM]-[IV]-x-H-x(2)-[FIV]-x-[ILV]-[ADGN]-[DGN]-x(2)-[AILV]-x(3)-[GS] | 25 |
| D-x-[AIV]-[FILV]-[AS]-G-[IV]-N-x(1,2)-G-x(0,1)-N | 26 |
| N-D-D-G-x(2)-[AS]-x-[GS]-[ILMV]-x(2)-[AL] | 27 |
| D-[FILMV]-x-[FILV]-S-G-x(0,1)-N-x-[AGT]-x-[NT] | 28 |
| K-x-[AS]-R-x-[ILMV]-[AGS]-L-[ILMV]-P-[FY] | 29 |
| G-W-x(5)-G-R-x-P-[WY] | 30 |
| H-[AGS]-x(2)-H-[ILM]-x-G-x-[DK]-[DH] | 31 |
| G-x-G-N-x(0,1)-Y-x(2,3)-E-x(2)-[FHW]-x(3)-[FILV]-x-[GP] | 32 |
| G-N-x(0,1)-Y-x(2,3)-E-x(2)-[FHW]-x(3)-[FILV]-x-[GP] | 33 |
| R-x(2)-L-N-x-G-H-[ST]-[FILV]-[AG]-x-[AGLV]-[ILV]-E | 34 |
| R-x(1,2)-L-x(0,1)-N-x-G-H-[ST]-[FILV]-[AG]-x-[AGLV]-[ILV]-E | 35 |
| G-G-G-[ATV]-x(2)-D-x-[AGTV]-G-x(1,2)-A-x(4,5)-R-G | 36 |
| L-N-x-G-H-[ST]-[FILV]-[AG]-x-[AGLV]-[ILV]-E | 37 |
| L-x(0,1)-N-x-G-H-[ST]-[FILV]-[AG]-x-[AGLV]-[ILV]-E | 38 |
| D-[AST]-[AS]-[AIV]-G-G-K-[NTV]-[AG]-[ILV] | 39 |
| R-x(2,3)-L-x(2,3)-G-H-[ST]-[FILV]-[AG]-x-[AGLV]-[ILV]-E | 40 |
| G-G-[ATV]-x(2)-D-x-[AGTV]-G-x(1,2)-A-x(4,5)-R-G | 41 |
| G-[ATV]-x(2)-D-x-[AGTV]-G-x(1,2)-A-x(4,5)-R-G | 42 |
| D-E-P-x-[AG]-[AENS]-L-D | 43 |
| G-S-S-R-E-x-A-[APV]-x(2)-[ILP]-x(4)-[FIV]-x(2)-[ILMV]-[ILV]-[AGS]-x(2)-[FYHAGS]-x-I-[FHY]-x(2)-N | 44 |
| S-S-R-E-x-A-[APV]-x(2)-[ILP]-x(4)-[FIV]-x(2)-[ILMV]-[ILV]-[AGS]-x(2)-[FY]-[AGS]-x-I-[FHY]-x(2)-N | 45 |
| S-R-E-x-A-[APV]-x(2)-[ILP]-x(4)-[FIV]-x(2)-[ILMV]-[ILV]-[AGS]-x(2)-[FY]-[AGS]-x-I-[FHY]-x(2)-N | 46 |
| R-E-x-A-[APV]-x(2)-[ILP]-x(4)-[FIV]-x(2)-[ILMV]-[ILV]-[AGS]-x(2)-[FY]-[AGS]-x-I-[FHY]-x(2)-N | 47 |
| S-R-x(3,5)-W-x-K-G-[ADES]-x-S-G-x(4)-[ILV]-x(2)-[FILMV]-x(2)-D-C-D-x-D-[ATV]-[ILMV]-x(3)-[AIV]-x(3)-G-x(2)-[ACG] | 48 |
| S-x(2,4)-R-x(1,3)-W-x-K-G-[ADES]-x-S-G-x(4)-[ILV]-x(2)-[FILMV]-x(2)-D-C-D-x-D-[ATV]-[ILMV]-x(3)-[AIV]-x(3)-G-x(2)-[ACG] | 49 |
| R-x(3,5)-W-x-K-G-[ADES]-x-S-G-x(4)-[ILV]-x(2)-[FILMV]-x(2)-D-C-D-x-D-[ATV]-[ILMV]-x(3)-[AIV]-x(3)-G-x(2)-[ACG] | 50 |
| W-x-K-G-[ADES]-x-S-G-x(4)-[ILV]-x(2)-[FILMV]-x(2)-D-C-D-x-D-[ATV]-[ILMV]-x(3)-[AIV]-x(3)-G-x(2)-[ACG] | 51 |
| K-G-[ADES]-x-S-x(4)-[ILV]-x(2)-[FILMV]-x(2)-D-C-D-x-D-[ATV]-[ILMV]-x(3)-[AIV]-x(3)-G-x(2)-[ACG] | 52 |
| K-G-x(2)-S-G-x(4)-[ILV]-x(2)-[FILMV]-x(2)-D-C-D-x-D-[ATV]-[ILMV]-x(3)-[AIV]-x(3)-G-x(2)-[ACG] | 53 |
| G-x(2,4)-C-H-x-G-x(2)-[AST]-C-[FW] | 54 |
| C-H-x-G-x(2)-[AST]-C-[FW] | 55 |
| I-x(3,5)-D-x-V-x-[ILV]-[AE]-[FILM]-[ST]-[APT]-[HY]-[DS]-x(3)-[AG]-R-[IV]-x(2)-R | 56 |
| D-x-V-x(2)-E-x(2)-[APT]-x-[DST]-x(3)-[AGV]-[QR]-[ILV] | 57 |
| Y-[IV]-G-K-[AS]-x(2)-[IL]-x(2)-R-x(3)-[HY] | 58 |

TABLE 3-continued 312 pathogenic adjuvant polypeptide sequences identified using the method of the invention

| Sequence | SEQ ID NO |
|---|---|
| P-[FL]-[ADEG]-x-G-x(2,3)-T-[ILV]-[AG]-x(2)-[ILM]-R-R-x(4)-[CGNS]-x(2)-[AGS]-x-[ASV] | 59 |
| P-x(3)-G-x-[AGV]-x-T-[ILV]-[AG]-x(2)-[ILM]-R-R-x(1,2)-L-x-[ACGST] | 60 |
| P-x(2,3)-G-x-[AGV]-x-T-[ILV]-[AG]-x(2)-[ILM]-R-R-x(1,2)-L-x-[ACGST] | 61 |
| P-x(3)-G-x(3)-T-[ILV]-[AG]-x(2)-[ILM]-R-R-x(1,2)-L-x-[ACGST] | 62 |
| P-x(2,3)-G-x(3)-T-[ILV]-[AG]-x(2)-[ILM]-R-R-x(1,2)-L-x-[ACGST] | 63 |
| G-x-[AGV]-x-T-[ILV]-[AG]-x(2)-[ILM]-R-R-x(1,2)-L-x-[ACGST] | 64 |
| T-[ILV]-[AG]-x(2)-[ILM]-R-R-x(1,2)-L-x-[ACGST] | 65 |
| P-x(1,2)-L-x(2,3)-G-[ACGSTV]-x-G-I-[AS]-[ASV]-G-x-[AST]-[AT]-x-[IMV]-x-[PST]-H-x(3)-[DE]-x(3)-[AGS] | 66 |
| P-x-[ILV]-[FIL]-x(2)-G-x(1,2)-G-x(0,1)-I-[AS]-[ASV]-G-x-[AST]-[AT]-x-[IMV]-x-[PST]-H-x(3)-[DE]-x(3)-[AGS] | 67 |
| L-x(2,3)-G-[ACGSTV]-x-G-I-[AS]-[ASV]-G-x-[AST]-[AT]-x-[IMV]-x-[PST]-H-x(3)-[DE]-x(3)-[AGS] | 68 |
| L-x(1,3)-G-[ACGSTV]-x-G-I-[AS]-[ASV]-G-x-[AST]-[AT]-x[IMV]-x-[PST]-H-x(3)-[DE]-x(3)-[AGS] | 69 |
| G-x(2)-G-I-[AS]-[ASV]-G-x-[AST]-[AT]-x-[IMV]-x-[PST]-H-x(3)-[DE]-x(3)-[AGS] | 70 |
| D-G-x-K-P-[SV]-x-R-R-[AILV]-[ILMV]-[FHWY]-[AGST] | 71 |
| G-x-K-P-[SV]-x-R-R-[AILV]-[ILMV]-[FHWY]-[AGST] | 72 |
| A-x-[AIPV]-x(3)-D-x(0,1)-G-x(2)-[LP]-[SV]-x-R-x-[AILV]-x-[FHWY]-[AGST] | 73 |
| K-P-[SV]-x-R-R-[AILV]-[ILMV]-[FHWY]-[AGST] | 74 |
| K-P-x(2)-R-R-[AILV]-[ILMV]-[FHWY]-[AGST] | 75 |
| R-x(3)-R-x(5)-G-x-[ILV]-P-G-x(2)-K-[AS]-S-W | 76 |
| R-x(2)-[FILV]-R-x(5)-G-x-[ILV]-P-G-x(1,2)-K-x(1,2)-S-W | 77 |
| R-x(5)-G-x-[ILV]-P-G-x(1,2)-K-x(1,2)-S-W | 78 |
| G-x(2)-P-G-x(2)-K-[AS]-S-W | 79 |
| G-x-[ILV]-P-G-x(1,2)-K-x(1,2)-S-W | 80 |
| G-x(4)-F-x-R-x-[AGNQST]-x-C-x(3)-[CS]-x(3)-[ADNQ] | 81 |
| G-x(3,4)-F-x-R-x-[AGNQST]-x-C-x(3)-[CS]-x(3)-[ADNQ] | 82 |
| F-N-[FILV]-A-D-x(2)-[ILV]-x(2)-[CG] | 83 |
| F-N-x-A-D-x(2)-[ILV]-x(2)-[CG] | 84 |
| G-x-[PS]-x-[ILV]-[ACNS]-D-P-G-x(2)-[ILM]-[AIV] | 85 |
| G-[AST]-[ANPST]-[APS]-G-Y-[IV]-G-x(3)-[AGNS]-[GNST]-x(3)-[DENQT] | 86 |
| E-[FL]-[DPST]-[DE]-x-Q-G-x(2)-G-x(0,2)-Y-x(4)-[ADEGN]-x(4)-[AIV]-[ACST]-x(4)-[DEGQ]-x-[HY] | 87 |
| P-x(3,4)-D-P-[FY]-[AG]-L-x-[RS]-x-[ASTV]-x-[AEGT]-[AILV] | 88 |
| Q-G-x(2)-G-x(0,2)-Y-x(4)-[ADEGN]-x(4)-[AIV]-[ACST]-x(4)-[DEGQ]-x-[HY] | 89 |
| T-x-[ANPST]-H-x-[FILMV]-x(3)-[FILMV]-[ILMV]-x-E-[AQS]-[ILV]-[FY]-R-[AG]-x(2)-[ILV] | 90 |
| L-[DE]-[IV]-[AST]-S-x-G-x(2)-R-x-[ILM] | 91 |
| R-x(0.2)-L-x(0,2)-D-x(2)-[AST]-x-G-[ALV]-[ILMV]-[FILV]-[FILMV]-[ST]-[DNQT] | 92 |
| L-D-x(2)-[AST]-x-G-x(0,1)-L-[ILMV]-[FILV]-x-[DNQST]-[DNQST] | 93 |
| M-[KR]-[IV]-[NQR]-x-S-V-K-x(2)-C-x(2)-C-[KR]-x-[IV]-[KR]-R | 94 |
| S-V-K-x(2)-C-x(2)-C-[KR]-x-[IV]-[KR]-R | 95 |
| V-K-x(2)-C-x(2)-C-[KR]-x-[IV]-[KR]-R | 96 |
| K-x(2)-C-x(2)-C-[KR]-x-[IV]-[KR]-R | 97 |
| I-[GV]-x(2)-[EG]-x-N-x(2)-L-x-[ANST]-x-[ILV]-x-[DEGNQS]-x(3)-[DENT] | 98 |
| Q-F-H-[PT]-E-[KR]-S-x(3)-G-x(2)-[FILMV] | 99 |
| G-[IV]-C-[LV]-G-x-Q-x-[FLM]-x(3)-[GS]-x-E | 100 |
| Q-F-H-[PT]-E-[KR]-S-x(2,3)-G-x(2)-[FILMV] | 101 |
| F-H-[PT]-E-[KR]-S-x(3)-G-x(2)-[FILMV] | 102 |
| F-H-x-E-[KR]-S-x(3)-G-x(2)-[FILMV] | 103 |
| C-[LV]-G-x-Q-x-[FLM]-x(3)-[GS]-x-E | 104 |
| H-[PT]-E-[KR]-S-x(3)-G-x(2)-[FILMV] | 105 |

TABLE 3-continued

312 pathogenic adjuvant polypeptide sequences identified using the method of the invention

| Sequence | ID |
|---|---|
| H-P-x-W-x-M-G-x(3)-[ST]-[ILV]-[DN]-S-[AS]-[ST]-[LM]-x-N-K-[AGL]-[FL]-E-x-[ILM]-E-[ACT]-x(2)-[FL]-[FY] | (SEQ ID NO: 106) |
| P-x-W-x-M-G-x(3)-[ST]-[ILV]-[DN]-S-[AS]-[ST]-[LM]-x-N-K-[AGL]-[FL]-E-x-[ILM]-E-[ACT]-x(2)-[FL]-[FY] | (SEQ ID NO: 107) |
| S-[AS]-[ST]-[LM]-x-N-K-[AGL]-[FL]-E-x-[ILM]-E-[ACT]-x(2)-[FL]-[FY] | (SEQ ID NO: 108) |
| N-K-[AGL]-[FL]-E-x-[ILM]-E-[ACT]-x(2)-[FL]-[FY] | (SEQ ID NO: 109) |
| P-[AIV]-D-S-E-H-x-[AG]-[ILV]-x(3)-[ILM] | (SEQ ID NO: 110) |
| D-S-E-H-x-[AG]-[ILV]-x(3)-[ILM] | (SEQ ID NO: 111) |
| G-x(3)-E-x-A-x(2)-E-x(3,5)-E-x(3)-[ILV]-x-[DNR]-x-[FILMV]-x(4)-[FILMV] | (SEQ ID NO: 112) |
| E-[CGTV]-x(2)-D-L-x(1,3)-G-x(4,5)-L-x-G | (SEQ ID NO: 113) |
| E-x-A-x(2)-E-x(3,5)-E-x(3)-[ILV]-x-[DNR]-x-[FILMV]-x(4)-[FILMV] | (SEQ ID NO: 114) |
| F-x(2,4)-E-x(3,5)-D-L-[FIM]-x-E-x-[AGTV] | (SEQ ID NO: 115) |
| L-x(2,4)-L-x(1,3)-R-x(3)-[EST]-[IL]-S-[GP]-G-E-x(2)-R-[AILV]-x-[ILM]-x(3)-[ILV] | (SEQ ID NO: 116) |
| V-x(2,3)-G-[ILPV]-[AS]-G-[AS]-G-K-[ST]-[STV]-L-[AIL] | (SEQ ID NO: 117) |
| R-x(0,1)-S-[ILM]-N-[ILV]-[AS]-x-[ACST]-[AV]-[ACGSV]-x(4)-E-x(2)-[KR]-Q | (SEQ ID NO: 118) |
| L-x(2,3)-P-x(4)-N-[TV]-G-[ANST]-x(2)-R-x-[ACT] | (SEQ ID NO: 119) |
| P-x(4)-N-[TV]-G-[ANST]-x(2)-R-x-[ACT] | (SEQ ID NO: 120) |
| D-[AP]-G-H-G-[DG]-x-[DEN]-x-G | (SEQ ID NO: 121) |
| L-x(2)-W-A-x-[EQR]-G-x(1,2)-L-x(1,2)-N-x(3)-[ST]-[TV] | (SEQ ID NO: 122) |
| A-x-[ENQR]-G-[FIMV]-L-[GL]-x-N-x(3)-[ST]-[ATV] | (SEQ ID NO: 123) |
| W-A-x-[EQR]-G-x(1,2)-L-x(1,2)-N-x(3)-[ST]-[TV] | (SEQ ID NO: 124) |
| I-x(1,2)-G-Q-D-P-Y-x-[GNQST] | (SEQ ID NO: 125) |
| L-x(1,3)-A-x-[EQR]-G-x(1,2)-L-[GIL]-x-[NT]-x(3)-[STV] | (SEQ ID NO: 126) |
| W-A-x(2)-G-x(1,2)-L-x(1,2)-N-x(3)-[ST]-[TV] | (SEQ ID NO: 127) |
| G-Q-D-P-Y-x-[GNQST] | (SEQ ID NO: 128) |
| E-x(4)-R-x-Q-x-[FY]-x-G-x-[CV]-[ILM]-x(3)-[GN]-x-G | (SEQ ID NO: 129) |
| V-x(0,1)-R-x(4)-Y-x(1,2)-R-x(3)-G-K | (SEQ ID NO: 130) |
| R-x(4,5)-Y-[ILM]-R-x(3)-G-K | (SEQ ID NO: 131) |
| T-G-x-E-M-E-A-[ILV]-x-[ACGS]-[ATV]-[NQST]-x-[ACGST]-x(2)-[ANTV]-[ILV]-[WY]-D-M-x-K-x(2)-[DEQS]-x-[ADEGS]-x(2)-[GIV] | (SEQ ID NO: 132) |
| G-x-E-M-E-A-[ILV]-x-[ACGS]-[ATV]-[NQST]-x-[ACGST]-x(2)-[ANTV]-[ILV]-[WY]-D-M-x-K-x(2)-[DEQS]-x-[ADEGS]-x(2)-[GIV] | (SEQ ID NO: 133) |
| E-M-E-A-[ILV]-x-[ACGS]-[ATV]-[NQST]-x-[ACGST]-x(2)-[ANTV]-[ILV]-[WY]-D-M-x-K-x(2)-[DEQS]-x-[ADEGS]-x(2)-[GIV] | (SEQ ID NO: 134) |
| G-x(1,2)-M-E-A-[ILV]-x-[ACGS]-[ATV]-[NQST]-x-[ACGST]-x(2)-[ANTV]-[ILV]-[WY]-D-M-x-K-x(2)-[DEQS]-x-[ADEGS]-x(2)-[GIV] | (SEQ ID NO: 135) |
| M-E-A-[ILV]-x-[ACGS]-[ATV]-[NQST]-x-[ACGST]x(2)-[ANTV]-[ILV]-[WY]-D-M-x-K-x(2)-[DEQS]-x-[ADEGS]-x(2)-[GIV] | (SEQ ID NO: 136) |
| L-x(3,4)-D-M-x-K-x(2)-[DEQS]-x-[ADEGS]-x(2)-[GIV] | (SEQ ID NO: 137) |
| G-x(1,3)-Y-x(1,3)-G-x-[IV]-x(2)-[FLV]-A-[DET]-x(2)-R-x(2)-[GI] | (SEQ ID NO: 138) |
| Y-x(1,3)-G-x-[IV]-x(2)-[FLV]-A-[DET]-x(2)-R-x(2)-[GI] | (SEQ ID NO: 139) |
| G-x-[IV]-x(2)-[FLV]-A-[DET]-x(2)-R-x(2)-[GI] | (SEQ ID NO: 140) |
| C-x-[FHY]-x-[LP]-[ST]-C-S-x-Y-x(4)-[FILV]-x(3)-[GNPS] | (SEQ ID NO: 141) |
| P-x(0,2)-G-G-[CD]-x(2)-G-x-R-x(4)-[FH]-x(3)-[FILM]-x(3)-G | (SEQ ID NO: 142) |
| G-G-[CD]-x(2)-G-x-R-x(4)-[FH]-x(3)-[FILM]-x(3)-G | (SEQ ID NO: 143) |
| P-x(0,2)-G-G-x(3)-G-x-R-x(4)-[FH]-x(3)-[FILM]-x(3)-G | (SEQ ID NO: 144) |
| G-G-x(3)-G-x-R-x(4)-[FH]-x(3)-[FILM]-x(3)-G | (SEQ ID NO: 145) |
| I-[AGV]-x-A-G-x-[AES]-[AG]-x-L-x(4,5)-A-x(3,5)-P-V-[FIL]-[AG]-V-P | (SEQ ID NO: 146) |
| A-G-x-[AES]-[AG]-x-L-x(4,5)-A-x(3,5)-P-V-[FIL]-[AG]-V-P | (SEQ ID NO: 147) |
| I-x(2,3)-A-G-x-[AES]-[AG]-x-L-x(4,5)-A-[AGNS]-x(4)-[PV]-[IV]-x-[AGV]-[PV]-[PV] | (SEQ ID NO: 148) |
| G-x-[AES]-[AG]-x-L-x(4,5)-A-x(3,5)-P-V-[FIL]-[AG]-V-P | (SEQ ID NO: 149) |
| A-x(4,5)-P-V-[FIL]-[AG]-V-P | (SEQ ID NO: 150) |
| S-x-G-[IM]-x-C-[AGS]-x(2)-[DE]-[IL] | (SEQ ID NO: 151) |
| G-x-D-x(2)-[AGNS]-G-[AGS]-G-x(2)-[AT]-D-[ILM]-x-[ASTV] | (SEQ ID NO: 152) |

TABLE 3-continued

312 pathogenic adjuvant polypeptide sequences identified using the method of the invention

| | |
|---|---|
| G-x(1,2)-D-x(2)-[AGNS]-G-[AGS]-G-x(2)-[AT]-D-[ILM]-x-[ASTV] | (SEQ ID NO: 153) |
| G-x(1,2)-D-x(3)-G-[AGS]-G-x(2)-[AT]-D-[ILM]-x-[ASTV] | (SEQ ID NO: 154) |
| D-x(2)-[AGNS]-G-[AGS]-G-x(2)-[AT]-D-[ILM]-x-[ASTV] | (SEQ ID NO: 155) |
| G-x-D-x(2,3)-G-x(0,1)-G-x(3)-D-[ILM]-x-[ASTV] | (SEQ ID NO: 156) |
| G-x(0,1)-G-x(0,1)-G-[ST]-G-[AST]-G-[ACGS]-[AST]-P-x-[FILV]-[ASV] | (SEQ ID NO: 157) |
| G-x(0,1)-G-x(0,1)-G-T-G-[AST]-[AG]-x-[ASTV]-[IPV] | (SEQ ID NO: 158) |
| H-x-D-N-[AILV]-x-[AP]-x(3)-G-[GN] | (SEQ ID NO: 159) |
| N-L-x-[KR]-G-x(0,1)-A-x(2,3)-A-x(2)-[ACNS]-x-[DEN]-x(3)-[DGNS] | (SEQ ID NO: 160) |
| D-N-L-x(0,2)-G-x(2,4)-A-x(2)-[ACNSV]-x-[CNV]-x(3)-[DEGN] | (SEQ ID NO: 161) |
| E-A-D-D-x-[AILV]-[AG]-x(2)-[ADSTV] | (SEQ ID NO: 162) |
| G-x-[IV]-[ACGTV]-[ILV]-[DN]-G-x-S-L-T-[ILV] | (SEQ ID NO: 163) |
| G-x(0,1)-S-[FIV]-[ACGSTV]-x-[DN]-G-x-[CS]-L-T-[ILV] | (SEQ ID NO: 164) |
| S-[FIV]-[ACGSTV]-x-[DN]-G-x-[CS]-L-T-[ILV] | (SEQ ID NO: 165) |
| G-[ADES]-S-[FIV]-[AS]-x-[ADGNQ]-G-x-C-x(1,3)-T | (SEQ ID NO: 166) |
| G-H-[FILV]-[LMV]-x-G-H-[IV]-x(3)-[AGTV]-x-[FILV] | (SEQ ID NO: 167) |
| S-[ANS]-G-x-H-[AST]-N-G-x-[ST]-x-[AIV]-R-x-[AILV] | (SEQ ID NO: 168) |
| S-x(0,1)-G-x-H-[AST]-N-G-x-[ST]-x-[AIV]-R-x-[AILV] | (SEQ ID NO: 169) |
| G-x-H-[AST]-N-G-x-[ST]-x-[AIV]-R-x-[AILV] | (SEQ ID NO: 170) |
| G-x-H-[ASTV]-N-G-x-[ST]-x-[AIV]-R-x-[AILV] | (SEQ ID NO: 171) |
| G-G-E-T-A-x(2)-[GP]-[DEGS]-[FILMV] | (SEQ ID NO: 172) |
| D-G-[IV]-G-[ST]-K-x(2)-[ILV] | (SEQ ID NO: 173) |
| G-E-T-A-x(2)-[GP]-[DEGS]-[FILMV] | (SEQ ID NO: 174) |
| E-x-[AS]-x-R-[PTV]-H-[DN]-[ST]-G-x(2)-[ST] | (SEQ ID NO: 175) |
| E-x-[AS]-x-R-x-H-[DN]-[ST]-G-x(2)-[ST] | (SEQ ID NO: 176) |
| R-[PTV]-H-[DN]-[ST]-G-x(2)-[ST] | (SEQ ID NO: 177) |
| R-G-R-[ST]-[FIL]-x(4)-[ILMV]-[FIL]-[ILV]-D-[DE]-[ACSV]-Q-[ENS]-x-[EPQST]-x(3)-[ILMV]-x(2)-[FILV]-[ILV]-x-R-G-x(2)-[AGSTV]-x(2)-[IV]-x(3)-[DN]-x(4)-[DRS] | (SEQ ID NO: 178) |
| G-x-[AT]-G-[CST]-G-K-[ST]x-[FILM]-[AST]-x-[ACSTV]-x-[AG] | (SEQ ID NO: 179) |
| N-x(3,4)-G-[LPV]-x(2)-G-[FWY]-x(3)-[LM]-x-[ILMV]-x(4)-[FY] | (SEQ ID NO: 180) |
| L-[HY]-Q-[ILMV]-x-G-R-x-[AGS]-R-x(4)-[AGQS] | (SEQ ID NO: 181) |
| L-[HY]-Q-x(2)-G-R-x-[AGS]-R-x(4)-[AGQS] | (SEQ ID NO: 182) |
| L-x-Q-[ILMV]-x-G-R-x-[AGS]-R-x(4)-[AGQS] | (SEQ ID NO: 183) |
| G-x(3)-L-x-[QT]-[ILM]-x-[GN]-R-x(2)-[NR]-x(4)-[AGNQS] | (SEQ ID NO: 184) |
| D-[ILV]-G-[AST]-G-x-G-x-P-[AGSV]-[ILV] | (SEQ ID NO: 185) |
| D-[AILV]-G-[AST]-G-x-G-x-P-[AGSV]-[ILV] | (SEQ ID NO: 186) |
| R-x(0,1)-R-R-x-C-x(2)-C-x(2)-R-[FY]-[GST]-T-x-E | (SEQ ID NO: 187) |
| R-x(0,1)-R-R-x(1,2)-C-x(2)-C-x(2)-R-[FY]-[GST]-T-x-E | (SEQ ID NO: 188) |
| R-R-R-x-C-x(2)-C-x(2)-R-x(1,2)-T-x(0,2)-T-x-E | (SEQ ID NO: 189) |
| R-R-R-x(1,2)-C-x(2)-C-x(2)-R-x(1,2)-T-x-E | (SEQ ID NO: 190) |
| R-R-x-C-x(2)-C-x(2)-R-x(1,2)-T-x(0,2)-T-x-E | (SEQ ID NO: 191) |
| L-x(1,3)-C-T-H-[FY]-x(2)-[FILMV]-x(3)-[FIL] | (SEQ ID NO: 192) |
| C-T-H-[FY]-x(2)-[FILMV]-x(3)-[FIL] | (SEQ ID NO: 193) |
| G-R-D-x-[GT]-x(2)-[ILV]-x(3)-[AS]-x(2)-[KR]-x-[FY]-[ILMV]-x-[AST]-x(4)-R-[AV]-x-R-[KR]-x(2)-[DEQ] | (SEQ ID NO: 194) |
| D-G-[PV]-[AGST]-[AGS]-[ASTV]-G-K-[GS]-[ST]-x-[ACGST]-x(2)-[ILMV]-[AGS] | (SEQ ID NO: 195) |
| D-G-x-[AGST]-[AGS]-[ASTV]-G-K-[GS]-[ST]-x-[ACGST]-x(2)-[ILMV]-[AGS] | (SEQ ID NO: 196) |
| D-G-x(2)-[AGS]-[ASTV]-G-K-[GS]-[ST]-x-[ACGST]-x(2)-[ILMV]-[AGS] | (SEQ ID NO: 197) |
| D-G-x(3)-[ASTV]-G-K-[GS]-[ST]-x-[ACGST]-x(2)-[ILMV]-[AGS] | (SEQ ID NO: 198) |
| D-G-x(4)-G-K-[GS]-[ST]-x-[ACGST]-x(2)-[ILMV]-[AGS] | (SEQ ID NO: 199) |
| D-G-x(3,4)-G-K-[GS]-[ST]-x-[ACGST]-x(2)-[ILMV]-[AGS] | (SEQ ID NO: 200) |
| G-[AST]-x-G-K-x(0,1)-T-x(0,1)-T-[ASTV]-x(2)-[ILMV]-x(3)-[FILMV] | (SEQ ID NO: 201) |
| G-[AST]-x-G-K-[AST]-[GST]-[TV]-[AST]-x-[FILM] | (SEQ ID NO: 202) |
| E-[ILMV]-I-[FILV]-A-x-[ADGNPST]-x-[NST]-x-[ADEN]-[GNS]-[DENQ] | (SEQ ID NO: 203) |

TABLE 3-continued

312 pathogenic adjuvant polypeptide sequences identified using the method of the invention

| | |
|---|---|
| L-A-A-G-x-[GS]-x-R-[FIM]-x-S-x(3)-K-[TV]-[LM]-x(2)-[ILV]-x-[DGQ]-x(2)-[LM]-[ILV]-x(3)-[FILV] | (SEQ ID NO: 204) |
| A-A-G-x-[GS]-x-R-[FIM]-x-S-x(3)-K-[TV]-[LM]-x(2)-[ILV]-x-[DGQ]-x(2)-[LM]-[ILV]-x(3)-[FILV] | (SEQ ID NO: 205) |
| A-G-x-[GS]-x-R-[FIM]-x-S-x(3)-K-[TV]-[LM]-x(2)-[ILV]-x-[DGQ]-x(2)-[LM]-[ILV]-x(3)-[FILV] | (SEQ ID NO: 206) |
| G-x-[GS]-x-R-[FIM]-x-S-x(3)-K-[TV]-[LM]-x(2)-[ILV]-x-[DGQ]-x(2)-[LM]-[ILV]-x(3)-[FILV] | (SEQ ID NO: 207) |
| G-x(1,3)-R-[FIM]-x-S-x(3)-K-[TV]-[LM]-x(2)-[ILV]-x-[DGQ]-x(2)-[LM]-[ILV]-x(3)-[FILV] | (SEQ ID NO: 208) |
| R-[FIM]-x-S-x(3)-K-[TV]-[LM]-x(2)-[ILV]-x-[DGQ]-x(2)-[LM]-[ILV]-x(3)-[FILV] | (SEQ ID NO: 209) |
| C-x(4)-T-A-[GNST]-[ST]-x-[AGNQST]-x(3)-[DE]-x-[LM]-G-[FILMV]-x(4)-[ACNST]-[AGS] | (SEQ ID NO: 210) |
| G-x(0,1)-S-[ST]-N-x(3)-H-x(2)-A-x-[AS] | (SEQ ID NO: 211) |
| C-D-K-x(2)-P-[AGS]-x(2)-[ILM]-[AG] | (SEQ ID NO: 212) |
| E-x-H-H-x(2)-K-x-D-x-[ILP]-S-G-[ST]-[AGL] | (SEQ ID NO: 213) |
| H-H-x(2)-K-x-D-x-[ILP]-S-G-[ST]-[AGL] | (SEQ ID NO: 214) |
| E-x-H-x(3)-K-x-D-x-[ILP]-S-G-[ST]-[AGL] | (SEQ ID NO: 215) |
| H-x(2)-K-x-D-x-[ILP]-S-G-[ST]-[AGL] | (SEQ ID NO: 216) |
| E-T-G-A-G-x-[HW]-G-x(1,3)-A-x(3)-A | (SEQ ID NO: 217) |
| E-T-G-A-G-x-[HW]-G-x(1,3)-A-x(1,3)-A | (SEQ ID NO: 218) |
| T-G-A-G-x-[HW]-G-x(1,3)-A-x(3)-A | (SEQ ID NO: 219) |
| G-x(3)-A-x-E-[PST]-[ACNS]-H-A-[FILV]-x(2)-[ALV] | (SEQ ID NO: 220) |
| T-G-A-G-x-[HW]-G-x(1,3)-A-x(1,3)-A | (SEQ ID NO: 221) |
| G-x(3)-A-x(0,1)-E-[PST]-[ACNS]-H-A-[FILV]-x(2)-[ALV] | (SEQ ID NO: 222) |
| G-x(2,3)-A-x(1,2)-E-[PST]-[ACNS]-H-A-[FILV]-x(2)-[ALV] | (SEQ ID NO: 223) |
| G-H-x-P-x(2)-[AP]-x(2)-P-G-V-x-[ILM]-x-E-x(2,4)-A-[AQST] | (SEQ ID NO: 224) |
| H-x-P-x(2)-[AP]-x(2)-P-G-V-x-[ILM]-x-E-x(2,4)-A-[AQST] | (SEQ ID NO: 225) |
| H-x-P-x(5)-P-G-V-x-[ILM]-x-E-x(2,4)-A-[AQST] | (SEQ ID NO: 226) |
| P-x(2)-[AP]-x(2)-P-G-V-x-[ILM]-x-E-x(2,4)-A-[AQST] | (SEQ ID NO: 227) |
| P-G-V-x-[ILM]-x-E-x(2,4)-A-[AQST] | (SEQ ID NO: 228) |
| G-[HR]-[FY]-E-[AG]-x-D-x-R | (SEQ ID NO: 229) |
| D-E-[IMV]-D-x-[GN]-[ILV]-[GS]-G-x(2)-[AGS]-x(2)-[IMV]-[AGS]-x(2)-[ILM]-x(2)-[ILV]-[AGS]-x(3)-Q-[ILV]-[FILMV]-[ACSTV]-[IV]-[ST]-H-x-[APV]-x-[ILV]-x-[ACGS]-x-[AGS] | (SEQ ID NO: 230) |
| G-x-[ST]-G-[ASTV]-G-K-[ST]-[ILMV]-x-[FILV]-x-[AGS]-[ILM]-x(4)-[GS]-x(3)-[DEGNST] | (SEQ ID NO: 231) |
| S-x(0,1)-G-x(0,1)-E-x-[ANS]-R-[FILMV]-x-L-[AS]-[FILMV] | (SEQ ID NO: 232) |
| S-x(1,2)-G-x(0,1)-E-x-[ANS]-R-[FILMV]-x-L-[AS]-[FILMV] | (SEQ ID NO: 233) |
| K-x-[IL]-P-x(2)-[AGS]-G-x(1,2)-G-G-x(0,1)-S-[ADNST]-[ADN]-x-[AGT]-[AGSTV]-x-[FLMV]-x(2)-[ILMV] | (SEQ ID NO: 234) |
| P-x(2)-[AGS]-G-x(1,2)-G-G-x(0,1)-S-[ADNST]-[ADN]-x-[AGT]-[AGSTV]-x-[FLMV]-x(2)-[ILMV] | (SEQ ID NO: 235) |
| G-[FILMV]-[AG]-G-G-S-x(2,3)-A-[AGSTV]-x-[AILV] | (SEQ ID NO: 236) |
| G-x(1,2)-G-G-x(0,1)-S-[ADNST]-[ADN]-x-[AGT]-[AGSTV]-x-[FLMV]-x(2)-[ILMV] | (SEQ ID NO: 237) |
| G-[ACTV]-[ILV]-[IV]-x-G-[ADEGNQS]-T-x-H-x(3)-[IV]-[ACSV]-x(3)-[AGNST]-x(2)-[ILMV] | (SEQ ID NO: 238) |
| D-[IV]-[AILV]-[IV]-[ACSTV]-[DE]-G-[FY]-x-G-N-x(2)-L-K-x(2-E-x(0,2)-G | (SEQ ID NO: 239) |
| G-[FY]-x-G-N-x(2)-L-K-x(2)-E-x(0,2)-G | (SEQ ID NO: 240) |
| V-[ACSTV]-x-G-x(1,3)-N-x(2,3)-L-K-x(2)-[EG]-[AGS] | (SEQ ID NO: 241) |
| G-N-x(2)-L-K-x(2)-E-x(0,2)-G | (SEQ ID NO: 242) |
| G-x(0,2)-G-x-P-x(4)-[EGNQ]-x(4)-[ILM]-x(2)-[DG]-[EG]-[FIL]-[DS]-[AS]-x-[AIV] | (SEQ ID NO: 243) |
| C-x-G-V-x(2)-A-[IMV]-x(2)-[AV] | (SEQ ID NO: 244) |
| N-x-D-G-[EGS]-x-[AGPV]-x(2)-C-G-N-[AG]-R-[ACTV]-x(4)-[AILV] | (SEQ ID NO: 245) |
| E-R-G-x(3,4)-T-x-[AS]-C-G-[ST]-[AG]-x(2)-[AGS]-[ACSTV] | (SEQ ID NO: 246) |
| D-G-[EGS]-x-[AGPV]-x(2)-C-G-N-[AG]-x-R-[ACTV]-x(4)-[AILV] | (SEQ ID NO: 247) |
| R-G-x(3,4)-T-x-[AS]-C-G-[ST]-[AG]-x(2)-[AGS]-[ACSTV] | (SEQ ID NO: 248) |
| G-[EGS]-x-[AGPV]-x(2)-C-G-N-[AG]-x-R-[ACTV]-x(4)-[AILV] | (SEQ ID NO: 249) |
| G-x(3,4)-T-x-[AS]-C-G-[ST]-[AG]-x(2)-[AGS]-[ACSTV] | (SEQ ID NO: 250) |

TABLE 3-continued 312 pathogenic adjuvant polypeptide sequences identified using the method of the invention

| Sequence | SEQ ID NO |
|---|---|
| C-G-N-[AG]-x-R-[ACTV]-x(4)-[AILV] | (SEQ ID NO: 251) |
| T-G-[IV]-[NST]-[AD]-x-[DE]-R-x(0,2)-T | (SEQ ID NO: 252) |
| R-x-G-x-T-E-x-[AGST]-x-[ADEST]-[IL]-x(4)-[GN] | (SEQ ID NO: 253) |
| T-x(0,2)-G-[IV]-[NST]-[AD]-x-[DE]-R-x(0,2)-T | (SEQ ID NO: 254) |
| K-x(2)-[IL]-T-[AG]-P-x-T-[IM]-x(3)-[STV] | (SEQ ID NO: 255) |
| P-D-C-G-[LM]-[KR] | (SEQ ID NO: 256) |
| G-[ST]-F-D-P-x(3)-G-H-x(2)-[ILMV]-[FILV]-x(2)-[AGST] | (SEQ ID NO: 257) |
| F-D-P-x(3)-G-H-x(2)-[ILMV]-[FILV]-x(2)-[AGST] | (SEQ ID NO: 258) |
| D-P-x(3)-G-H-x(2)-[ILMV]-[FILV]-x(2)-[AGST] | (SEQ ID NO: 259) |
| G-x(3)-H-H-x(2)-E-[AGST]-x(2)-K-[AGSV]-x-[AGS]-x-[ASTV]-[ILMV]-x(2)-[AC] | (SEQ ID NO: 260) |
| H-H-x(2)-E-D-x-[AG]-[IL]-[ACSTV]-[IL]-G-x(2)-[FILV] | (SEQ ID NO: 261) |
| H-H-x(2)-E-[AGST]-x(2)-K-[AGSV]-x-[AGS]-x-[ASTV]-[ILMV]-x(2)-[AC] | (SEQ ID NO: 262) |
| G-x(3)-H-x(2,3)-E-[AGST]-x(2)-K-[AGSV]-x-[AGS]-x-[ASTV]-[ILMV]-x(2)-[AC] | (SEQ ID NO: 263) |
| G-x(3,4)-H-x(2)-E-[AGST]-x(2)-K-[AGSV]-x-[AGS]-x-[ASTV]-[ILMV]-x(2)-[AC] | (SEQ ID NO: 264) |
| T-[DGP]-x-[ADGNPS]-F-x-[DENT]-H-[LM]-[ILM]-x(2)-[FILMV]-x(2)-[HY] | (SEQ ID NO: 265) |
| H-x(2)-E-D-x-[AG]-[IL]-[ACSTV]-[IL]-G-x(2)-[FILV] | (SEQ ID NO: 266) |
| E-D-x-[AG]-[IL]-[ACSTV]-[IL]-G-x(2)-[FILV] | (SEQ ID NO: 267) |
| G-G-Y-x-R-[ILMV]-x-[KR]-x(3)-R-x(2)-[DG]-x-[AGSTV]-x(4)-[ILV] | (SEQ ID NO: 268) |
| G-Y-x-R-[ILMV]-x-[KR]-x(3)-R-x(2)-[DG]-x-[AGSTV]-x(4)-[ILV] | (SEQ ID NO: 269) |
| G-Y-x(0,1)-R-[ILMV]-x-[KR]-x(3)-R-x(2)-[DG]-x-[AGSTV]-x(4)-[ILV] | (SEQ ID NO: 270) |
| Y-x-N-[CST]x(4)-K-[AST]-x-[ACSTV]-[ADG]-x(2)-[CDGV]-[GT]-x-[AGSTV]-x-[AGTV]-x(3)-[AIV] | (SEQ ID NO: 271) |
| G-V-x-F-M-[ACG]-E-x-[ASV]-x(2)-[ILV]-[ACNST] | (SEQ ID NO: 272) |
| V-x-F-M-[ACG]-E-x-[ASV]-x(2)-[ILV]-[ACNST] | (SEQ ID NO: 273) |
| S-G-x-A-x-G-[AIV]-D-x-(2)-[ACS]-x(3)-[ACSTV]-[ILMV] | (SEQ ID NO: 274) |
| G-x-A-x-G-[AIV]-D-x(2)-[ACS]-x(3)-[ACSTV]-[ILMV] | (SEQ ID NO: 275) |
| E-M-x-T-G-E-G-K-T-[IL]-x(4)-[APV]-x(4)-[AGSV]-[FILM]-x(4)-[CTV]-x-[ILMV]-x-T-x-N-[DE]-Y-L-[ASV]-x(2)-[DGQ] | (SEQ ID NO: 276) |
| M-x-T-G-E-G-K-T-[IL]-x(4)-[APV]-x(4)-[AGSV]-[FILM]-x(4)-[CTV]-x-[ILMV]-x-T-x-N-[DE]-Y-L-[ASV]-x(2)-[DGQ] | (SEQ ID NO: 277) |
| R-x(0,1)-D-x-Q-[IL]-x-G-R-[ACST]-[AG]-R-x-G-D-x-G-x-[AST]-x-[FI]-x(2)-S-x-[DEGQ]-D-x-[LV]-[FILMV] | (SEQ ID NO: 278) |
| R-[ILV]-D-x(0,2)-L-x(1,3)-G-R-[ACST]-[AG]-R-x-G-D-x-G-x-[AST]-x-[FI]-x(2)-S-x-[DEGQ]-D-x-[LV]-[FILMV] | (SEQ ID NO: 279) |
| Q-[IL]-x-G-R-[ACST]-[AG]-R-x-G-D-x-G-x-[AST]-x-[FI]-x(2)-S-x-[DEGQ]-D-x-[LV]-[FILMV] | (SEQ ID NO: 280) |
| D-x(0,2)-L-x(1,3)-G-R-[ACST]-[AG]-R-x-G-D-x-G-x-[AST]-x-[FI]-x(2)-S-x-[DEGQ]-D-x-[LV]-[FILMV] | (SEQ ID NO: 281) |
| R-x(2,4)-L-x(1,3)-G-R-[ACST]-[AG]-R-x-G-D-x-G-x-[AST]-x-[FI]-x(2)-S-x-[DEGQ]-D-x-[LV]-[FILMV] | (SEQ ID NO: 282) |
| L-x(1,3)-G-R-[ACST]-[AG]-R-x-G-D-x-G-x-[AST]-x-[FI]-x(2)-S-x-[DEGQ]-D-x-[LV]-[FILMV] | (SEQ ID NO: 283) |
| T-[NQS]-M-A-G-R-G-[TV]-D-I-x-[ILP]-[DGST]-x-[DEGNS] | (SEQ ID NO: 284) |
| M-A-G-R-G-[TV]-D-I-x-[ILP]-[DGST]-x-[DEGNS] | (SEQ ID NO: 285) |
| G-[DES]-S-H-G-x(2)-[ILMV]-[GTV]-[ILV]-[ILV]-[DENST]-G | (SEQ ID NO: 286) |
| G-H-[AE]-x-D-x(2)-[IL]-x-D-x-[ASV]-[ASV]-[CD]-x-[RS]-x(2)-T-P-[ST]-x-A-x(3)-[ALV] | (SEQ ID NO: 287) |
| H-[AE]-x-D-x(2)-[IL]-x-D-x-[ASV]-[ASV]-[CD]-x-[RS]-x(2)-T-P-[ST]-x-A-x(3)-[ALV] | (SEQ ID NO: 288) |
| D-[ILV]-x-[DEGQST]-[ST]-G-x-T-L-x(4)-L | (SEQ ID NO: 289) |
| L-x(1,2)-Q-[AILV]-[AGPST]-G-x(0,1)-R-x-[GV]-R | (SEQ ID NO: 290) |
| H-[IL]-G-[ILV]-T-E-[AS]-G-x(4)-[AGS]-x-[IV]-x-S-[AST]-x-[AGS]-[FIL]-[AGS]-x-[ILM]-[LM]-x(2)-[GN]-[IL]-G-[ADN]-T-[ILMV]-R-x-S-[ILM]-[AST] | (SEQ ID NO: 291) |
| L-x(0,2)-G-[ILV]-T-E-[AS]-G-x(4)-[AGS]-x-[IV]-x-S-[AST]-x-[AGS]-[FIL]-[AGS]-x-[ILM]-[LM]-x(2)-[GN]-[IL]-G-[ADN]-T-[ILMV]-R-x-S-[ILM]-[AST] | (SEQ ID NO: 292) |
| G-C-x(0,1)-V-x(0,1)-N-[AG]-[ILP]-G-E-x(3)-[AST]-x(2)-[AG]-x-[ASTV] | (SEQ ID NO: 293) |

TABLE 3-continued

312 pathogenic adjuvant polypeptide sequences identified using the method of the invention

| Sequence | SEQ ID NO |
|---|---|
| C-x(0,1)-V-x(0,1)-N-[AG]-[ILP]-G-E-x(3)-[AST]1-x(2)-[AG]-x-[ASTV] | 294 |
| R-[IV]-G-[AV]-N-x-G-S-[IL] | 295 |
| L-x(3,5)-G-[ADN]-T-[ILMV]-R-x-S-[ILM]-[AST] | 296 |
| L-x(3,4)-G-x(1,3)-T-[ILMV]-R-x-S-[ILM]-[AST] | 297 |
| I-x(0,2)-G-[AV]-N-x-G-S-[IL] | 298 |
| Gx-[ST]-G-[ACS]-G-K-[ST]-[ST]-x-[IL]-[KR]-x-[FILMV]-[DN]-x-[ILM] | 299 |
| R-x(3)-[GS]-M-[LV]-F-Q-x(3)-[LPV]-[FW] | 300 |
| E-x(2)-K-x(2,3)-N-x-[IV]-x-[ANSTV]-x(3)-[CG]-x(4)-[IPV]-x(4)-[AEGN]-x(2)-[ILV] | 301 |
| G-x(2)-[AG]-x-S-D-[AG]-D-[AIV]-[AILV]-x-H-[AST]-[ILV]-x-[DN]-[AS]-x(2)-[GS]-[AGV] | 302 |
| S-D-[AG]-D-[AIV]-[AILV]-x-H-[AST]-[ILV]-x-[DN]-[AS]-x(2)-[GS]-[AGV] | 303 |
| G-x(4,5)-D-[AGT]-D-[AIPV]-[AILV]-x-H-[AST]-[ILV]-x-[DN]-[LAS]-x(2)-[GS]-[AGV] | 304 |
| D-[AG]-D-[AIV]-[AILV]-x-H-[AST]-[ILV]-x-[DN]-[AS]-x(2)-[GS]-[AGV] | 305 |
| G-x-G-x-D-x-H-x-[FIL]-x(2)-[DEGNS]-x(4)-[ILP]-[ACGV]-[GIV]-[ILV] | 306 |
| G-x-G-x(0,1)-D-x-H-x-[FIL]-x(2)-[DEGNS]-x(4)-[ILP]-[ACGV]-[GIV]-[ILV] | 307 |
| G-x-D-x-H-x-[FIL]-x(2)-[DEGNS]-x(4)-[ILP]-[ACGV]-[GIV]-[ILV] | 308 |
| E-[ASTV]-H-x(0,2)-P-x(2)-A-x-[CS]-D-[AGNS] | 309 |
| E-x-H-x(2)-P-x(2)-A-x-[CS]-D-[AGNS] | 310 |
| E-x(0,1)-H-x(2)-P-x(2)-A-x-[CS]-D-[AGNS] | 311 |
| I-x(2)-[LV]-x(2)-H-x(4,5)-K-x(0,1)-D-x(2)-[GST]-x(2)-[AG]-[FL]-x(4)-[AGNS]-x-R-[KR]-x-[LM]-[IL]-x-[FHY] | 312 |
| H-x(4,5)-K-x(0,1)-D-x(2)-[GST]-x(2)-[AG]-[FL]-x(4)-[AGNS]-x-R-[KR]-x-[LM]-[IL]-x-[FHY] | 313 |
| G-x(2)-[ADEGQS]-[ALV]-Q-x(2,3)-L-x(3,4)-I-x(2)-[LV]-x(2)-H | 314 |
| G-x-[ST]-E-x-[AIL]-P-[IV]-S-S-x-[AGT]-x(3)-[AILV] | 315 |
| G-x(1,2)-E-x-[AIL]-P-[IV]-S-S-x-[AGT]-x(3)-[AILV] | 316 |
| G-x(0,2)-E-x-[AIL]-P-[IV]-S-S-x-[AGT]-x(3)-[AILV] | 317 |
| H-P-x-[FWY]-[ST]-G-x(2)-[KR]-x(4)-[ADEGST]-[GS]-x-[AIV]-[ADES]-x-F-x(2)-[KR]-[FY] | 318 |
| H-P-x-[FWY]-[AEST]-G-x(2)-[KR]-x(4)-[ADEGST]-[GS]-x-[AIV]-[ADES]-x-F-x(2)-[KR]-[FY] | 319 |
| P-x-[FWY]-[ST]-G-x(2)-[KR]-x(4)-[ADEGST]-[GS]-x-[AIV]-[ADES]-x-F-x(2)-[KR]-[FY] | 320 |

REFERENCES (THE CONTENTS OF WHICH ARE HEREBY INCORPORATED IN FULL)

[1] O'Hagan et al. (2001) *Biomol Eng.* 18:69-85.
[2] Moriwaki et al. (2001) *J Biol. Chem.* 276:23065-76.
[3] Zipfel & Felix (2005) *Curr Opin Plant Biol* 8:353-60.
[4] Chalifour et al. (2004) *Blood* 104:1778-83.
[5] Alvarez (2005) *Front Biosci.* 10:582-7.
[6] O'Hagan (2001) *Curr Drug Targets Infect Disord.* 1:273-86.
[7] Altschul et al. (1990) *J. Mol. Biol.* 215(3):403-10.
[8] Jonassen et al. (1995) *Protein Science* 4:1587-1595.
[9] Nielsen et al. (1997) *Protein Eng.* 10:1-6.
[10] Dutta (2002) *Immunol Lett.* 83:153-161.
[11] Bairoch et al. (1997) *Nucl. Acids Res.* 25:217-221.
[12] van Dijk et al. (1986) *Methods Find. Exp. Clin. Pharmacol.* 8(3):189-93.
[13] Ronnberg et al. (1997) *Vaccine* 15(17-18):1820-6.
[14] Berthou et al. (1987) *FEBS Letters* 218:55-58.
[15] Rich et al. (1984) *J. Med. Chem.* 27:417-422.
[16] Audhya et al. (1986) *Science* 231:997-999.
[17] Ogawa et al. (2002) *Eur. J. Immunol.* 32:2543-50.
[18] Suzue & Young (1996) *J Immunol.* 156:873-879.
[19] Bodanszky (1993) *Principles of peptide Synthesis* (ISBN: 0387564314).
[20] Fields et al. (1997) *Methods in Enzymology* 289: *Solid-Phase Peptide Synthesis.* ISBN: 0121821900
[21] Chan & White (2000) *Fmoc Solid Phase Peptide Synthesis* ISBN: 0199637245.
[22] Kullmann (1987) *Enzymatic Peptide Synthesis.* ISBN: 0849368413.
[23] Kazmierski (1999) *Peptidomimetics Protocols.* ISBN: 0896035174.
[24] Abell (1999) *Advances in Amino Acid Mimetics and Peptidomimetics.* ISBN: 0762306149.
[25] U.S. Pat. No. 5,331,573 (Balaji).
[26] Goodman et al. (2001) *Biopolymers* 60:229-245.
[27] Hruby & Balse (2000) *Curr Med Chem* 7:945-970.
[28] Ribka & Rich (1998) *Curr Opin Chem Biol* 2:441-452.
[29] Barron & Zuckermann (1999) *Curr Opin Chem Biol* 3:681-687.
[30] WO 91/19735.
[31] Chakraborty et al. (2002) *Curr Med Chem* 9:421-435.
[32] Ibba (1996) *Biotechnol Genet Eng Rev* 13:197-216.
[33] Gennaro (2000) *Remington: The Science and Practice of pharmacy.* 20th edition, ISBN: 0683306472

[34] Singh et al. (2001) *Pharm Res.* 18:1476-1479.
[35] Singh & O'Hagan (1999) *Nat Biotechnol* 17(11):1075-81
[36] Souberbielle et al. (1996) *Gene Ther* 3(10):853-8
[37] Asai et al. (2001) *Infect Immun.* 69:7387-7395.
[38] Asea et al. (2002) *J Biol Chem.* 277:15028-15034.
[39] Hirschfeld et al. (2001) *Infect Immun* 69(3):1477-82.
[40] Mullarkey et al. (2003) *J Pharmacol Exp Ther* 304(3): 1093-1102.
[41] *Current Protocols in Molecular Biology* (F. M. Ausubel et al., eds., 1987) Supplement 30.
[42] Smith & Waterman (1981) *Adv. Appl. Math.* 2: 482-489.
[43] Rice et al. (2000) *Trends in Genetics* 16:276-277.

---

The invention claimed is:

1. A method for identifying a polypeptide which acts as an adjuvant in a host organism, comprising the steps of:
   a) generating protein families by grouping together amino acid sequences from at least a different pathogenic organisms, which sequences share a BLAST alignment with an E-score less than 1E-05;
   b) selecting a protein family generated in step a), wherein:
      (i) the family includes sequences from at least b different pathogenic organisms, and
      (ii) at least one of the proteins in the family does not share a BLAST alignment with an E-score smaller than 1E-05 with amino acid sequences from a chosen non-pathogenic organism;
   c) determining sequence motifs that are conserved within the family selected in step b) implemented by a computer, wherein the computer comprises a processor; and
   d) selecting a polypeptide sequence that comprises the motifs determined in step c), thereby identifying the polypeptide,
   wherein: a is at least 60 and b is at least 30, where b<a.

2. The method of claim 1, wherein the amino acid sequences used in step a) are available from a genomic database.

3. The method of claim 1, wherein the chosen non-pathogenic organism is *Drosophila melanogaster*.

4. The method of claim 1, further comprising producing a fusion polypeptide that comprises the polypeptide sequence selected in step (d) and an antigen, in a single fusion polypeptide chain.

5. The method of claim 4, wherein the polypeptide sequence selected in step (d) comprises an amino acid sequence selected from the group consisting of the amino acid sequences listed in Table 3.

6. The method of claim 4, wherein the antigen is a bacterial, viral, fungal, or tumor antigen.

7. The method of claim 1, wherein the host organism is a vertebrate.

8. The method of claim 7, wherein the host organism is a human.

9. The method of claim 1, wherein the identified polypeptide comprises an amino acid sequence selected from the group consisting of the amino acid sequences listed in Table 3.

10. The method of claim 1, wherein the polypeptide is at least 8 amino acids in length.

11. The method of claim 1, wherein the polypeptide is fewer than 100 amino acids in length.

12. A method comprising producing the polypeptide identified by
   a) generating protein families by grouping together amino acid sequences from at least a different pathogenic organisms, which sequences share a BLAST alignment with an E score less than 1E-05;
   b) selecting a protein family generated in step a), wherein:
      (i) the family includes sequences from at least b different pathogenic organisms, and
      (ii) at least one of the proteins in the family does not share a BLAST alignment with an E-score smaller than 1E-05 with amino acid sequences from a chosen non pathogenic organism;
   c) determining sequence motifs that are conserved within the family selected in step b) implemented by a computer, wherein the computer comprises a processor; and
   d) selecting a polypeptide sequence that comprises the motifs determined in step c), thereby identifying the polypeptide,
   wherein: a is at least 60 and b is at least 30, where b<a.

13. The method of claim 12, wherein the host organism is a vertebrate.

14. The method of claim 13, wherein the host organism is a human.

15. The method of claim 12, wherein the identified polypeptide comprises an amino acid sequence selected from the group consisting of the amino acid sequences listed in Table 3.

16. The method of claim 12, wherein the polypeptide is at least 8 amino acids in length.

17. The method of claim 12, wherein the polypeptide is fewer than 100 amino acids in length.

* * * * *

SEQUENCE LISTING

```
<160> NUMBER OF SEQ ID NOS: 584

<210> SEQ ID NO 1
<211> LENGTH: 6
<212> TYPE: PRT
<213> ORGANISM: Artificial Sequence
<220> FEATURE:
<223> OTHER INFORMATION: Polypeptide

<400> SEQUENCE: 1

Cys His Gly His Tyr Trp
1               5

<210> SEQ ID NO 2
<211> LENGTH: 9
<212> TYPE: PRT
<213> ORGANISM: Artificial Sequence
<220> FEATURE:
<223> OTHER INFORMATION: Polypeptide

<400> SEQUENCE: 2

Leu Ile Cys His Gly His Leu Tyr Trp
1               5

<210> SEQ ID NO 3
<211> LENGTH: 9
<212> TYPE: PRT
<213> ORGANISM: Artificial Sequence
<220> FEATURE:
<223> OTHER INFORMATION: Polypeptide

<400> SEQUENCE: 3

Ala Ala Cys His Gly His Tyr Trp Lys
1               5

<210> SEQ ID NO 4
<211> LENGTH: 10
<212> TYPE: PRT
<213> ORGANISM: Artificial Sequence
<220> FEATURE:
<223> OTHER INFORMATION: Polypeptide

<400> SEQUENCE: 4

Leu Ile Cys His Gly Ala His Leu Tyr Trp
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Polypeptide

<400> SEQUENCE: 5

Ala Leu Thr Thr Glu
1               5

<210> SEQ ID NO 6
```

```
<211> LENGTH: 6
<212> TYPE: PRT
<213> ORGANISM: Artificial Sequence
<220> FEATURE:
<223> OTHER INFORMATION: Polypeptide

<400> SEQUENCE: 6

Pro Asp Cys Gly Leu Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Polypeptide

<400> SEQUENCE: 7

Pro Asp Cys Gly Leu Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Polypeptide

<400> SEQUENCE: 8

Pro Asp Cys Gly Met Arg
1               5

<210> SEQ ID NO 9
<211> LENGTH: 6
<212> TYPE: PRT
<213> ORGANISM: Artificial Sequence
<220> FEATURE:
<223> OTHER INFORMATION: Polypeptide

<400> SEQUENCE: 9

Pro Asp Cys Gly Met Lys
1               5

<210> SEQ ID NO 10
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 10

Gly Phe Tyr Xaa Xaa Arg Xaa Xaa Ser Thr Xaa Xaa Gly Gln Arg Xaa
1               5                   10                  15

Ile Leu Val Ile Leu Val Xaa Xaa Arg Arg Xaa His Lys Arg Gly Asn
            20                  25                  30

Gln Arg Xaa Xaa Leu
        35

<210> SEQ ID NO 11
<211> LENGTH: 38
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(38)
<223> OTHER INFORMATION: Xaa = any am

```
<210> SEQ ID NO 15
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 15

Gly Gly Xaa Ser Xaa Glu His Arg Xaa Ile Val Ser Xaa Xaa Ser Thr
 1               5                  10                  15

Ala Gly Ser

<210> SEQ ID NO 16
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 16

Gly Xaa Ser Xaa Glu His Arg Xaa Ile Val Ser Xaa Xaa Ser Thr Ala
 1               5                  10                  15

Gly Ser

<210> SEQ ID NO 17
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 17

His Gly Xaa Xaa Gly Glu Asp Thr Gly Xaa Ile Leu Met Val Xaa Ala
 1               5                  10                  15

Gly Ser

<210> SEQ ID NO 18
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid

<400> SEQUENCE: 18

Val Xaa Xaa Xaa Ala Ser Val Xaa Lys Xaa Xaa Ala Ile Leu Val Xaa
 1               5                  10                  15

Xaa Ala Ile Met Val Xaa Xaa Ala Ile Leu Val Phe Xaa Val Xaa Val
                20                  25                  30

<210> SEQ ID NO 19
<211> LENGTH: 24
<212> TYPE: PRT
```

-continued

```
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 19

Lys Xaa Xaa Ala Ile Leu Val Xaa Xaa Ala Ile Met Val Xaa Xaa Ala
 1               5                  10                  15

Ile Leu Val Phe Xaa Val Xaa Val
             20

<210> SEQ ID NO 20
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 20

Ala Xaa Xaa Xaa Gly Xaa Xaa Glu Xaa Asp Asn Pro Xaa Xaa Xaa Asp
 1               5                  10                  15

Ile Leu Val Xaa Ala Gly Xaa Asp Xaa Xaa Xaa Lys Xaa Xaa Ile Leu
             20                  25                  30

Val

<210> SEQ ID NO 21
<211> LENGTH: 31
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(31)
<223> OTHER INFORMATION: Xaa = any amino acid

<400> SEQUENCE: 21

Ala Xaa Xaa Xaa Gly Xaa Xaa Glu Xaa Xaa Xaa Xaa Xaa Asp Ile Leu
 1               5                  10                  15

Val Xaa Ala Gly Xaa Asp Xaa Xaa Xaa Lys Xaa Xaa Ile Leu Val
             20                  25                  30

<210> SEQ ID NO 22
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 22

Gly Xaa Xaa Glu Xaa Asp Asn Pro Xaa Xaa Xaa Asp Ile Leu Val Xaa
 1               5                  10                  15

Ala Gly Xaa Asp Xaa Xaa Xaa Lys Xaa Xaa Ile Leu Val
             20                  25

<210> SEQ ID NO 23
```

```
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 23

Gly Xaa Xaa Glu Xaa Xaa Xaa Xaa Asp Ile Leu Val Xaa Ala Gly
 1               5                  10                  15

Xaa Asp Xaa Xaa Xaa Lys Xaa Xaa Ile Leu Val
            20                  25

<210> SEQ ID NO 24
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 24

Glu Xaa Asp Asn Pro Xaa Xaa Xaa Asp Ile Leu Val Xaa Ala Gly Xaa
 1               5                  10                  15

Asp Xaa Xaa Xaa Lys Xaa Xaa Ile Leu Val
            20                  25

<210> SEQ ID NO 25
<211> LENGTH: 36
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(36)
<223> OTHER INFORMATION: Xaa = any amino acid

<400> SEQUENCE: 25

Gln Phe Ile Leu Met Ile Val Xaa His Xaa Xaa Phe Ile Val Xaa Ile
 1               5                  10                  15

Leu Val Ala Asp Gly Asn Asp Gly Asn Xaa Xaa Ala Ile Leu Val Xaa
            20                  25                  30

Xaa Xaa Gly Ser
        35

<210> SEQ ID NO 26
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 26

Asp Xaa Ala Ile Val Phe Ile Leu Val Ala Ser Gly Ile Val Asn Xaa
 1               5                  10                  15

Gly Asn
```

<210> SEQ ID NO 27
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 27

Asn Asp Asp Gly Xaa Xaa Ala Ser Xaa Gly Ser Ile Leu Met Val Xaa
 1               5                  10                  15

Xaa Ala Leu

<210> SEQ ID NO 28
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 28

Asp Phe Ile Leu Met Val Xaa Phe Ile Leu Val Ser Gly Asn Xaa Ala
 1               5                  10                  15

Gly Thr Xaa Asn Thr
            20

<210> SEQ ID NO 29
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 29

Lys Xaa Ala Ser Arg Xaa Ile Leu Met Val Ala Gly Ser Leu Ile Leu
 1               5                  10                  15

Met Val Pro Phe Tyr
            20

<210> SEQ ID NO 30
<211> LENGTH: 13
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(13)
<223> OTHER INFORMATION: Xaa = any amino acid

<400> SEQUENCE: 30

Gly Trp Xaa Xaa Xaa Xaa Xaa Gly Arg Xaa Pro Trp Tyr
 1               5                  10

<210> SEQ ID NO 31
<211> LENGTH: 17
<212> TYPE: PRT

```
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 31

His Ala Gly Ser Xaa Xaa His Ile Leu Met Xaa Gly Xaa Asp Lys Asp
 1               5                  10                  15

His

<210> SEQ ID NO 32
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 32

Gly Xaa Gly Asn Tyr Xaa Xaa Glu Xaa Xaa Phe His Trp Xaa Xaa Xaa
 1               5                  10                  15

Phe Ile Leu Val Xaa Gly Pro
            20

<210> SEQ ID NO 33
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 33

Gly Asn Tyr Xaa Xaa Glu Xaa Xaa Phe His Trp Xaa Xaa Xaa Phe Ile
 1               5                  10                  15

Leu Val Xaa Gly Pro
            20

<210> SEQ ID NO 34
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 34

Arg Xaa Xaa Leu Asn Xaa Gly His Ser Thr Phe Ile Leu Val Ala Gly
 1               5                  10                  15

Xaa Ala Gly Leu Val Ile Leu Val Glu
            20                  25

<210> SEQ ID NO 35
<211> LENGTH: 24
<212> TYPE: PRT
<213> ORGANISM: Artificial Sequence
```

```
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 35

Arg Xaa Leu Asn Xaa Gly His Ser Thr Phe Ile Leu Val Ala Gly Xaa
 1               5                  10                  15

Ala Gly Leu Val Ile Leu Val Glu
            20

<210> SEQ ID NO 36
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 36

Gly Gly Gly Ala Thr Val Xaa Xaa Asp Xaa Ala Gly Thr Val Gly Xaa
 1               5                  10                  15

Ala Xaa Xaa Xaa Xaa Arg Gly
            20

<210> SEQ ID NO 37
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 37

Leu Asn Xaa Gly His Ser Thr Phe Ile Leu Val Ala Gly Xaa Ala Gly
 1               5                  10                  15

Leu Val Ile Leu Val Glu
            20

<210> SEQ ID NO 38
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 38

Leu Asn Xaa Gly His Ser Thr Phe Ile Leu Val Ala Gly Xaa Ala Gly
 1               5                  10                  15

Leu Val Ile Leu Val Glu
            20

<210> SEQ ID NO 39
<211> LENGTH: 20
<212> TYPE: PRT
<213> ORGANISM: Artificial Sequence
```

```
<220> FEATURE:
<223> OTHER INFORMATION: Polypeptide

<400> SEQUENCE: 39

Asp Ala Ser Thr Ala Ser Ala Ile Val Gly Gly Lys Asn Thr Val Ala
 1               5                  10                  15

Gly Ile Leu Val
         20

<210> SEQ ID NO 40
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 40

Arg Xaa Xaa Leu Xaa Xaa Gly His Ser Thr Phe Ile Leu Val Ala Gly
 1               5                  10                  15

Xaa Ala Gly Leu Val Ile Leu Val Glu
         20                  25

<210> SEQ ID NO 41
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 41

Gly Gly Ala Thr Val Xaa Xaa Asp Xaa Ala Gly Thr Val Gly Xaa Ala
 1               5                  10                  15

Xaa Xaa Xaa Xaa Arg Gly
         20

<210> SEQ ID NO 42
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 42

Gly Ala Thr Val Xaa Xaa Asp Xaa Ala Gly Thr Val Gly Xaa Ala Xaa
 1               5                  10                  15

Xaa Xaa Xaa Arg Gly
         20

<210> SEQ ID NO 43
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
```

```
<222> LOCATION: (1)...(12)
<223> OTHER INFORMATION: Xaa = any amino acid

<400> SEQUENCE: 43

Asp Glu Pro Xaa Ala Gly Ala Glu Asn Ser Leu Asp
1               5                   10

<210> SEQ ID NO 44
<211> LENGTH: 49
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(49)
<223> OTHER INFORMATION: Xaa = any amino acid

<400> SEQUENCE: 44

Gly Ser Ser Arg Glu Xaa Ala Ala Pro Val Xaa Xaa Ile Leu Pro Xaa
1               5                   10                  15

Xaa Xaa Xaa Phe Ile Val Xaa Xaa Ile Leu Met Val Ile Leu Val Ala
                20                  25                  30

Gly Ser Xaa Xaa Phe Tyr Ala Gly Ser Xaa Ile Phe His Tyr Xaa Xaa
            35                  40                  45

Asn

<210> SEQ ID NO 45
<211> LENGTH: 48
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(48)
<223> OTHER INFORMATION: Xaa = any amino acid

<400> SEQUENCE: 45

Ser Ser Arg Glu Xaa Ala Ala Pro Val Xaa Xaa Ile Leu Pro Xaa Xaa
1               5                   10                  15

Xaa Xaa Phe Ile Val Xaa Xaa Ile Leu Met Val Ile Leu Val Ala Gly
                20                  25                  30

Ser Xaa Xaa Phe Tyr Ala Gly Ser Xaa Ile Phe His Tyr Xaa Xaa Asn
            35                  40                  45

<210> SEQ ID NO 46
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 46

Ser Arg Glu Xaa Ala Ala Pro Val Xaa Xaa Ile Leu Pro Xaa Xaa Xaa
1               5                   10                  15

Xaa Phe Ile Val Xaa Xaa Ile Leu Met Val Ile Leu Val Ala Gly Ser
                20                  25                  30

Xaa Xaa Phe Tyr Ala Gly Ser Xaa Ile Phe His Tyr Xaa Xaa Asn
            35                  40                  45
```

<210> SEQ ID NO 47
<211> LENGTH: 46
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(46)
<223> OTHER INFORMATION: Xaa = any amino acid

<400> SEQUENCE: 47

Arg Glu Xaa Ala Ala Pro Val Xaa Xaa Ile Leu Pro Xaa Xaa Xaa Xaa
 1               5                  10                  15

Phe Ile Val Xaa Xaa Ile Leu Met Val Ile Leu Val Ala Gly Ser Xaa
            20                  25                  30

Xaa Phe Tyr Ala Gly Ser Xaa Ile Phe His Tyr Xaa Xaa Asn
        35                  40                  45

<210> SEQ ID NO 48
<211> LENGTH: 59
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(59)
<223> OTHER INFORMATION: Xaa = any amino acid

<400> SEQUENCE: 48

Ser Arg Xaa Xaa Xaa Trp Xaa Lys Gly Ala Asp Glu Ser Xaa Ser Gly
 1               5                  10                  15

Xaa Xaa Xaa Xaa Ile Leu Val Xaa Xaa Phe Ile Leu Met Val Xaa Xaa
            20                  25                  30

Asp Cys Asp Xaa Asp Ala Thr Val Ile Leu Met Val Xaa Xaa Xaa Ala
            35                  40                  45

Ile Val Xaa Xaa Xaa Gly Xaa Xaa Ala Cys Gly
        50                  55

<210> SEQ ID NO 49
<211> LENGTH: 57
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(57)
<223> OTHER INFORMATION: Xaa = any amino acid

<400> SEQUENCE: 49

Ser Xaa Xaa Arg Xaa Trp Xaa Lys Gly Ala Asp Glu Ser Xaa Ser Gly
 1               5                  10                  15

Xaa Xaa Xaa Xaa Ile Leu Val Xaa Xaa Phe Ile Leu Met Val Xaa Xaa
            20                  25                  30

Asp Cys Asp Xaa Asp Ala Thr Val Ile Leu Met Val Xaa Xaa Ala Ile
            35                  40                  45

Val Xaa Xaa Gly Xaa Xaa Ala Cys Gly
        50                  55

<210> SEQ ID NO 50
<211> LENGTH: 58
<212> TYPE: PRT
<213> ORGANISM: Artificial Sequence
<220> FEATURE:

```
<223> OTHER INFORMATION: Polypeptide
<220> FEATURE:
<221> NAME/KEY: VARIANT
<222> LOCATION: (1)...(58)
<223> OTHER INFORMATION: Xaa = any amino acid

<400> SEQUENCE: 50

Arg Xaa Xaa Xaa Trp Xaa Lys Gly Ala Asp Glu Ser Xaa Ser Gly Xaa
 1               5                  10                  15

Xaa Xaa Xaa Ile Leu Val Xaa Xaa Phe Ile Leu Met Val Xaa Xaa Asp
            20                  25                  30

Cys Asp Xaa Asp Ala Thr Val Ile Leu Met Val Xaa Xaa Xaa Ala Ile
        35                  40                  45

Val Xaa Xaa Xaa Gly Xaa Xaa Ala Cys Gly
    50                  55

<210> SEQ ID NO 51
<211> LENGTH: 54
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(54)
<223> OTHER INFORMATION: Xaa = any amino acid

<400> SEQUENCE: 51

Trp Xaa Lys Gly Ala Asp Glu Ser Xaa Ser Gly Xaa Xaa Xaa Xaa Ile
 1               5                  10                  15

Leu Val Xaa Xaa Phe Ile Leu Met Val Xaa Xaa Asp Cys Asp Xaa Asp
            20                  25                  30

Ala Thr Val Ile Leu Met Val Xaa Xaa Xaa Ala Ile Val Xaa Xaa Xaa
        35                  40                  45

Gly Xaa Xaa Ala Cys Gly
    50

<210> SEQ ID NO 52
<211> LENGTH: 52
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(52)
<223> OTHER INFORMATION: Xaa = any amino acid

<400> SEQUENCE: 52

Lys Gly Ala Asp Glu Ser Xaa Ser Gly Xaa Xaa Xaa Xaa Ile Leu Val
 1               5                  10                  15

Xaa Xaa Phe Ile Leu Met Val Xaa Xaa Asp Cys Asp Xaa Asp Ala Thr
            20                  25                  30

Val Ile Leu Met Val Xaa Xaa Xaa Ala Ile Val Xaa Xaa Xaa Gly Xaa
        35                  40                  45

Xaa Ala Cys Gly
    50

<210> SEQ ID NO 53
<211> LENGTH: 49
<212> TYPE: PRT
<213> ORGANISM: Artificial Sequence
<220> FEATURE:
<223> OTHER INFORMATION: Polypeptide
<220> FEATURE:
```

```
<221> NAME/KEY: VARIANT
<222> LOCATION: (1)...(49)
<223> OTHER INFORMATION: Xaa = any amino acid

<400> SEQUENCE: 53

Lys Gly Xaa Xaa Ser Gly Xaa Xaa Xaa Xaa Ile Leu Val Xaa Xaa Phe
  1               5                  10                  15

Ile Leu Met Val Xaa Xaa Asp Cys Asp Xaa Asp Ala Thr Val Ile Leu
             20                  25                  30

Met Val Xaa Xaa Xaa Ala Ile Val Xaa Xaa Xaa Gly Xaa Xaa Ala Cys
         35                  40                  45

Gly

<210> SEQ ID NO 54
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 54

Gly Xaa Xaa Cys His Xaa Gly Xaa Xaa Ala Ser Thr Cys Phe Trp
  1               5                  10                  15

<210> SEQ ID NO 55
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(12)
<223> OTHER INFORMATION: Xaa = any amino acid

<400> SEQUENCE: 55

Cys His Xaa Gly Xaa Xaa Ala Ser Thr Cys Phe Trp
  1               5                  10

<210> SEQ ID NO 56
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 56

Ile Xaa Xaa Xaa Asp Xaa Val Xaa Ile Leu Val Ala Glu Phe Ile Leu
  1               5                  10                  15

Met Ser Thr Ala Pro Thr His Tyr Asp Ser Xaa Xaa Xaa Ala Gly Arg
             20                  25                  30

Ile Val Xaa Xaa Arg
         35

<210> SEQ ID NO 57
<211> LENGTH: 26
<212> TYPE: PRT
<213> ORGANISM: Artificial Sequence
<220> FEATURE:
```

```
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 57

Asp Xaa Val Xaa Xaa Glu Xaa Xaa Ala Pro Thr Xaa Asp Ser Thr Xaa
 1               5                   10                  15

Xaa Xaa Ala Gly Val Gln Arg Ile Leu Val
            20                  25

<210> SEQ ID NO 58
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 58

Tyr Ile Val Gly Lys Ala Ser Xaa Xaa Ile Leu Xaa Xaa Arg Xaa Xaa
 1               5                   10                  15

Xaa His Tyr

<210> SEQ ID NO 59
<211> LENGTH: 41
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(41)
<223> OTHER INFORMATION: Xaa = any amino acid

<400> SEQUENCE: 59

Pro Phe Leu Ala Asp Glu Gly Xaa Gly Xaa Xaa Thr Ile Leu Val Ala
 1               5                   10                  15

Gly Xaa Xaa Ile Leu Met Arg Arg Xaa Xaa Xaa Xaa Cys Gly Asn Ser
            20                  25                  30

Xaa Xaa Ala Gly Ser Xaa Ala Ser Val
        35                  40

<210> SEQ ID NO 60
<211> LENGTH: 31
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(31)
<223> OTHER INFORMATION: Xaa = any amino acid

<400> SEQUENCE: 60

Pro Xaa Xaa Xaa Gly Xaa Ala Gly Val Xaa Thr Ile Leu Val Ala Gly
 1               5                   10                  15

Xaa Xaa Ile Leu Met Arg Arg Xaa Leu Xaa Ala Cys Gly Ser Thr
            20                  25                  30

<210> SEQ ID NO 61
<211> LENGTH: 30
<212> TYPE: PRT
```

```
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid

<400> SEQUENCE: 61

Pro Xaa Xaa Gly Xaa Ala Gly Val Xaa Thr Ile Leu Val Ala Gly Xaa
 1               5                  10                  15

Xaa Ile Leu Met Arg Arg Xaa Leu Xaa Ala Cys Gly Ser Thr
            20                  25                  30

<210> SEQ ID NO 62
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 62

Pro Xaa Xaa Xaa Gly Xaa Xaa Xaa Thr Ile Leu Val Ala Gly Xaa Xaa
 1               5                  10                  15

Ile Leu Met Arg Arg Xaa Leu Xaa Ala Cys Gly Ser Thr
            20                  25

<210> SEQ ID NO 63
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 63

Pro Xaa Xaa Gly Xaa Xaa Xaa Thr Ile Leu Val Ala Gly Xaa Xaa Ile
 1               5                  10                  15

Leu Met Arg Arg Xaa Leu Xaa Ala Cys Gly Ser Thr
            20                  25

<210> SEQ ID NO 64
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 64

Gly Xaa Ala Gly Val Xaa Thr Ile Leu Val Ala Gly Xaa Xaa Ile Leu
 1               5                  10                  15

Met Arg Arg Xaa Leu Xaa Ala Cys Gly Ser Thr
            20                  25

<210> SEQ ID NO 65
<211> LENGTH: 21
<212> TYPE: PRT
```

```
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 65

Thr Ile Leu Val Ala Gly Xaa Xaa Ile Leu Met Arg Arg Xaa Leu Xaa
 1               5                  10                  15

Ala Cys Gly Ser Thr
            20

<210> SEQ ID NO 66
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 66

Pro Xaa Leu Xaa Xaa Gly Ala Cys Gly Ser Thr Val Xaa Gly Ile Ala
 1               5                  10                  15

Ser Ala Ser Val Gly Xaa Ala Ser Thr Ala Thr Xaa Ile Met Val Xaa
                20                  25                  30

Pro Ser Thr His Xaa Xaa Xaa Asp Glu Xaa Xaa Xaa Ala Gly Ser
            35                  40                  45

<210> SEQ ID NO 67
<211> LENGTH: 46
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(46)
<223> OTHER INFORMATION: Xaa = any amino acid

<400> SEQUENCE: 67

Pro Xaa Ile Leu Val Phe Ile Leu Xaa Xaa Gly Xaa Gly Ile Ala Ser
 1               5                  10                  15

Ala Ser Val Gly Xaa Ala Ser Thr Ala Thr Xaa Ile Met Val Xaa Pro
                20                  25                  30

Ser Thr His Xaa Xaa Xaa Asp Glu Xaa Xaa Xaa Ala Gly Ser
            35                  40                  45

<210> SEQ ID NO 68
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid

<400> SEQUENCE: 68

Leu Xaa Xaa Gly Ala Cys Gly Ser Thr Val Xaa Gly Ile Ala Ser Ala
 1               5                  10                  15

Ser Val Gly Xaa Ala Ser Thr Ala Thr Xaa Ile Met Val Xaa Pro Ser
```

```
                    20                  25                  30

Thr His Xaa Xaa Xaa Asp Glu Xaa Xaa Xaa Ala Gly Ser
        35                  40                  45

<210> SEQ ID NO 69
<211> LENGTH: 44
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(44)
<223> OTHER INFORMATION: Xaa = any amino acid

<400> SEQUENCE: 69

Leu Xaa Gly Ala Cys Gly Ser Thr Val Xaa Gly Ile Ala Ser Ala Ser
1               5                   10                  15

Val Gly Xaa Ala Ser Thr Ala Thr Xaa Ile Met Val Xaa Pro Ser Thr
            20                  25                  30

His Xaa Xaa Xaa Asp Glu Xaa Xaa Xaa Ala Gly Ser
        35                  40

<210> SEQ ID NO 70
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 70

Gly Xaa Xaa Gly Ile Ala Ser Ala Ser Val Gly Xaa Ala Ser Thr Ala
1               5                   10                  15

Thr Xaa Ile Met Val Xaa Pro Ser Thr His Xaa Xaa Xaa Asp Glu Xaa
            20                  25                  30

Xaa Xaa Ala Gly Ser
        35

<210> SEQ ID NO 71
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 71

Asp Gly Xaa Lys Pro Ser Val Xaa Arg Arg Ala Ile Leu Val Ile Leu
1               5                   10                  15

Met Val Phe His Trp Tyr Ala Gly Ser Thr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
```

```
<222> LOCATION: (1)...(25)
<223> OTHER INFORMATION: Xaa = any amino acid

<400> SEQUENCE: 72

Gly Xaa Lys Pro Ser Val Xaa Arg Arg Ala Ile Leu Val Ile Leu Met
1               5                   10                  15

Val Phe His Trp Tyr Ala Gly Ser Thr
            20                  25

<210> SEQ ID NO 73
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 73

Ala Xaa Ala Ile Pro Val Xaa Xaa Xaa Asp Gly Xaa Xaa Leu Pro Ser
1               5                   10                  15

Val Xaa Arg Xaa Ala Ile Leu Val Xaa Phe His Trp Tyr Ala Gly Ser
            20                  25                  30

Thr

<210> SEQ ID NO 74
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 74

Lys Pro Ser Val Xaa Arg Arg Ala Ile Leu Val Ile Leu Met Val Phe
1               5                   10                  15

His Trp Tyr Ala Gly Ser Thr
            20

<210> SEQ ID NO 75
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 75

Lys Pro Xaa Xaa Arg Arg Ala Ile Leu Val Ile Leu Met Val Phe His
1               5                   10                  15

Trp Tyr Ala Gly Ser Thr
            20

<210> SEQ ID NO 76
<211> LENGTH: 24
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(24)
<223> OTHER INFORMATION: Xaa = any amino acid

<400> SEQUENCE: 76

Arg Xaa Xaa Xaa Arg Xaa Xaa Xaa Xaa Gly Xaa Ile Leu Val Pro
 1               5                  10                  15

Gly Xaa Xaa Lys Ala Ser Ser Trp
            20

<210> SEQ ID NO 77
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 77

Arg Xaa Xaa Phe Ile Leu Val Arg Xaa Xaa Xaa Xaa Gly Xaa Ile
 1               5                  10                  15

Leu Val Pro Gly Xaa Lys Xaa Ser Trp
            20                  25

<210> SEQ ID NO 78
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 78

Arg Xaa Xaa Xaa Xaa Xaa Gly Xaa Ile Leu Val Pro Gly Xaa Lys Xaa
 1               5                  10                  15

Ser Trp

<210> SEQ ID NO 79
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(12)
<223> OTHER INFORMATION: Xaa = any amino acid

<400> SEQUENCE: 79

Gly Xaa Xaa Pro Gly Xaa Xaa Lys Ala Ser Ser Trp
 1               5                  10

<210> SEQ ID NO 80
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(12)
<223> OTHER INFORMATION: Xaa = any amino acid
```

```
<400> SEQUENCE: 80

Gly Xaa Ile Leu Val Pro Gly Xaa Lys Xaa Ser Trp
 1               5                  10

<210> SEQ ID NO 81
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 81

Gly Xaa Xaa Xaa Xaa Phe Xaa Arg Xaa Ala Gly Asn Gln Ser Thr Xaa
 1               5                  10                  15

Cys Xaa Xaa Xaa Cys Ser Xaa Xaa Xaa Ala Asp Asn Gln
             20                  25

<210> SEQ ID NO 82
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 82

Gly Xaa Xaa Xaa Phe Xaa Arg Xaa Ala Gly Asn Gln Ser Thr Xaa Cys
 1               5                  10                  15

Xaa Xaa Xaa Cys Ser Xaa Xaa Xaa Ala Asp Asn Gln
             20                  25

<210> SEQ ID NO 83
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 83

Phe Asn Phe Ile Leu Val Ala Asp Xaa Xaa Ile Leu Val Xaa Xaa Cys
 1               5                  10                  15

Gly

<210> SEQ ID NO 84
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 84

Phe Asn Xaa Ala Asp Xaa Xaa Ile Leu Val Xaa Xaa Cys Gly
```

<210> SEQ ID NO 85
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 85

Gly Xaa Pro Ser Xaa Ile Leu Val Ala Cys Asn Ser Asp Pro Gly Xaa
1               5                   10                  15

Xaa Ile Leu Met Ala Ile Val
            20

<210> SEQ ID NO 86
<211> LENGTH: 36
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(36)
<223> OTHER INFORMATION: Xaa = any amino acid

<400> SEQUENCE: 86

Gly Ala Ser Thr Ala Asn Pro Ser Thr Ala Pro Ser Gly Tyr Ile Val
1               5                   10                  15

Gly Xaa Xaa Xaa Ala Gly Asn Ser Gly Asn Ser Thr Xaa Xaa Xaa Asp
            20                  25                  30

Glu Asn Gln Thr
        35

<210> SEQ ID NO 87
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 87

Glu Phe Leu Asp Pro Ser Thr Asp Glu Xaa Gln Gly Xaa Xaa Gly Tyr
1               5                   10                  15

Xaa Xaa Xaa Xaa Ala Asp Glu Gly Asn Xaa Xaa Xaa Xaa Ala Ile Val
            20                  25                  30

Ala Cys Ser Thr Xaa Xaa Xaa Xaa Asp Glu Gly Gln Xaa His Tyr
            35                  40                  45

<210> SEQ ID NO 88
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid -continued

```
<400> SEQUENCE: 88

Pro Xaa Xaa Xaa Asp Pro Phe Tyr Ala Gly Leu Xaa Arg Ser Xaa Ala
1               5                   10                  15

Ser Thr Val Xaa Ala Glu Gly Thr Ala Ile Leu Val
            20                  25

<210> SEQ ID NO 89
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 89

Gln Gly Xaa Xaa Gly Tyr Xaa Xaa Xaa Xaa Ala Asp Glu Gly Asn Xaa
1               5                   10                  15

Xaa Xaa Xaa Ala Ile Val Ala Cys Ser Thr Xaa Xaa Xaa Xaa Asp Glu
            20                  25                  30

Gly Gln Xaa His Tyr
            35

<210> SEQ ID NO 90
<211> LENGTH: 44
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(44)
<223> OTHER INFORMATION: Xaa = any amino acid

<400> SEQUENCE: 90

Thr Xaa Ala Asn Pro Ser Thr His Xaa Phe Ile Leu Met Val Xaa Xaa
1               5                   10                  15

Xaa Phe Ile Leu Met Val Ile Leu Met Val Xaa Glu Ala Gln Ser Ile
            20                  25                  30

Leu Val Phe Tyr Arg Ala Gly Xaa Xaa Ile Leu Val
            35                  40

<210> SEQ ID NO 91
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 91

Leu Asp Glu Ile Val Ala Ser Thr Ser Xaa Gly Xaa Xaa Arg Xaa Ile
1               5                   10                  15

Leu Met

<210> SEQ ID NO 92
<211> LENGTH: 32
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(32)
<223> OTHER INFORMATION: Xaa = any amino acid

<400> SEQUENCE: 92

Arg Leu Asp Xaa Xaa Ala Ser Thr Xaa Gly Ala Leu Val Ile Leu Met
 1               5                  10                  15

Val Phe Ile Leu Val Phe Ile Leu Met Val Ser Thr Asp Asn Gln Thr
                20                  25                  30

<210> SEQ ID NO 93
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 93

Leu Asp Xaa Xaa Ala Ser Thr Xaa Gly Leu Ile Leu Met Val Phe Ile
 1               5                  10                  15

Leu Val Xaa Asp Asn Gln Ser Thr Asp Asn Gln Ser Thr
                20                  25

<210> SEQ ID NO 94
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 94

Met Lys Arg Ile Val Asn Gln Arg Xaa Ser Val Lys Xaa Xaa Cys Xaa
 1               5                  10                  15

Xaa Cys Lys Arg Xaa Ile Val Lys Arg Arg
                20                  25

<210> SEQ ID NO 95
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 95

Ser Val Lys Xaa Xaa Cys Xaa Xaa Cys Lys Arg Xaa Ile Val Lys Arg
 1               5                  10                  15

Arg

<210> SEQ ID NO 96
<211> LENGTH: 16
<212> TYPE: PRT
<213> ORGANISM: Artificial Sequence
<220> FEATURE:
<223> OTHER INFORMATION: Polypeptide
<220> FEATURE:
```

```
<221> NAME/KEY: VARIANT
<222> LOCATION: (1)...(16)
<223> OTHER INFORMATION: Xaa = any amino acid

<400> SEQUENCE: 96

Val Lys Xaa Xaa Cys Xaa Xaa Cys Lys Arg Xaa Ile Val Lys Arg Arg
 1               5                  10                  15

<210> SEQ ID NO 97
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 97

Lys Xaa Xaa Cys Xaa Xaa Cys Lys Arg Xaa Ile Val Lys Arg Arg
 1               5                  10                  15

<210> SEQ ID NO 98
<211> LENGTH: 34
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(34)
<223> OTHER INFORMATION: Xaa = any amino acid

<400> SEQUENCE: 98

Gly Val Xaa Xaa Glu Gly Xaa Asn Xaa Xaa Leu Xaa Ala Asn Ser Thr
 1               5                  10                  15

Xaa Ile Leu Val Xaa Asp Glu Gly Asn Gln Ser Xaa Xaa Xaa Asp Glu
            20                  25                  30

Asn Thr

<210> SEQ ID NO 99
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 99

Gln Phe His Pro Thr Glu Lys Arg Ser Xaa Xaa Xaa Gly Xaa Xaa Phe
 1               5                  10                  15

Ile Leu Met Val
            20

<210> SEQ ID NO 100
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid
```

<400> SEQUENCE: 100

Gly Ile Val Cys Leu Val Gly Xaa Gln Xaa Phe Leu Met Xaa Xaa Xaa
 1               5                  10                  15

Gly Ser Xaa Glu
            20

<210> SEQ ID NO 101
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 101

Gln Phe His Pro Thr Glu Lys Arg Ser Xaa Xaa Gly Xaa Xaa Phe Ile
 1               5                  10                  15

Leu Met Val

<210> SEQ ID NO 102
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 102

Phe His Pro Thr Glu Lys Arg Ser Xaa Xaa Xaa Gly Xaa Xaa Phe Ile
 1               5                  10                  15

Leu Met Val

<210> SEQ ID NO 103
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 103

Phe His Xaa Glu Lys Arg Ser Xaa Xaa Xaa Gly Xaa Xaa Phe Ile Leu
 1               5                  10                  15

Met Val

<210> SEQ ID NO 104
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 104

Cys Leu Val Gly Xaa Gln Xaa Phe Leu Met Xaa Xaa Xaa Gly Ser Xaa

```
                 1               5                  10                 15
Glu

<210> SEQ ID NO 105
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 105

His Pro Thr Glu Lys Arg Ser Xaa Xaa Xaa Gly Xaa Xaa Phe Ile Leu
 1               5                  10                 15

Met Val

<210> SEQ ID NO 106
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 106

His Pro Xaa Trp Xaa Met Gly Xaa Xaa Xaa Ser Thr Ile Leu Val Asp
 1               5                  10                 15

Asn Ser Ala Ser Ser Thr Leu Met Xaa Asn Lys Ala Gly Leu Phe Leu
            20                  25                  30

Glu Xaa Ile Leu Met Glu Ala Cys Thr Xaa Xaa Phe Leu Phe Tyr
        35                  40                  45

<210> SEQ ID NO 107
<211> LENGTH: 46
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(46)
<223> OTHER INFORMATION: Xaa = any amino acid

<400> SEQUENCE: 107

Pro Xaa Trp Xaa Met Gly Xaa Xaa Xaa Ser Thr Ile Leu Val Asp Asn
 1               5                  10                 15

Ser Ala Ser Ser Thr Leu Met Xaa Asn Lys Ala Gly Leu Phe Leu Glu
            20                  25                  30

Xaa Ile Leu Met Glu Ala Cys Thr Xaa Xaa Phe Leu Phe Tyr
        35                  40                  45

<210> SEQ ID NO 108
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid
```

<400> SEQUENCE: 108

Ser Ala Ser Ser Thr Leu Met Xaa Asn Lys Ala Gly Leu Phe Leu Glu
1               5                   10                  15

Xaa Ile Leu Met Glu Ala Cys Thr Xaa Xaa Phe Leu Phe Tyr
            20                  25                  30

<210> SEQ ID NO 109
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 109

Asn Lys Ala Gly Leu Phe Leu Glu Xaa Ile Leu Met Glu Ala Cys Thr
1               5                   10                  15

Xaa Xaa Phe Leu Phe Tyr
            20

<210> SEQ ID NO 110
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 110

Pro Ala Ile Val Asp Ser Glu His Xaa Ala Gly Ile Leu Val Xaa Xaa
1               5                   10                  15

Xaa Ile Leu Met
            20

<210> SEQ ID NO 111
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 111

Asp Ser Glu His Xaa Ala Gly Ile Leu Val Xaa Xaa Xaa Ile Leu Met
1               5                   10                  15

<210> SEQ ID NO 112
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)
<223> OTHER INFORMATION: Xaa = any amino acid

<400> SEQUENCE: 112

```
Gly Xaa Xaa Xaa Glu Xaa Ala Xaa Xaa Glu Xaa Xaa Xaa Glu Xaa Xaa
1               5                   10                  15

Xaa Ile Leu Val Xaa Asp Asn Arg Xaa Phe Ile Leu Met Val Xaa Xaa
            20                  25                  30

Xaa Xaa Phe Ile Leu Met Val
        35
```

```
<210> SEQ ID NO 113
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 113

Glu Cys Gly Thr Val Xaa Xaa Asp Leu Xaa Gly Xaa Xaa Xaa Xaa Leu
1               5                   10                  15

Xaa Gly
```

```
<210> SEQ ID NO 114
<211> LENGTH: 35
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(35)
<223> OTHER INFORMATION: Xaa = any amino acid

<400> SEQUENCE: 114

Glu Xaa Ala Xaa Xaa Glu Xaa Xaa Xaa Glu Xaa Xaa Xaa Ile Leu Val
1               5                   10                  15

Xaa Asp Asn Arg Xaa Phe Ile Leu Met Val Xaa Xaa Xaa Xaa Phe Ile
            20                  25                  30

Leu Met Val
        35
```

```
<210> SEQ ID NO 115
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 115

Phe Xaa Xaa Glu Xaa Xaa Xaa Asp Leu Phe Ile Met Xaa Glu Xaa Ala
1               5                   10                  15

Gly Thr Val
```

```
<210> SEQ ID NO 116
<211> LENGTH: 36
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(36)
```

<223> OTHER INFORMATION: Xaa = any amino acid

<400> SEQUENCE: 116

Leu Xaa Xaa Leu Xaa Arg Xaa Xaa Xaa Glu Ser Thr Ile Leu Ser Gly
1               5                   10                  15

Pro Gly Glu Xaa Xaa Arg Ala Ile Leu Val Xaa Ile Leu Met Xaa Xaa
            20                  25                  30

Xaa Ile Leu Val
        35

<210> SEQ ID NO 117
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 117

Val Xaa Xaa Gly Ile Leu Pro Val Ala Ser Gly Ala Ser Gly Lys Ser
1               5                   10                  15

Thr Ser Thr Val Leu Ala Ile Leu
            20

<210> SEQ ID NO 118
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 118

Arg Ser Ile Leu Met Asn Ile Leu Val Ala Ser Xaa Ala Cys Ser Thr
1               5                   10                  15

Ala Val Ala Cys Gly Ser Val Xaa Xaa Xaa Glu Xaa Xaa Lys Arg
            20                  25                  30

Gln

<210> SEQ ID NO 119
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 119

Leu Xaa Xaa Pro Xaa Xaa Xaa Xaa Asn Thr Val Gly Ala Asn Ser Thr
1               5                   10                  15

Xaa Xaa Arg Xaa Ala Cys Thr
            20

<210> SEQ ID NO 120
<211> LENGTH: 20
<212> TYPE: PRT
<213> ORGANISM: Artificial Sequence

```
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 120

Pro Xaa Xaa Xaa Xaa Asn Thr Val Gly Ala Asn Ser Thr Xaa Xaa Arg
1               5                   10                  15

Xaa Ala Cys Thr
        20

<210> SEQ ID NO 121
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 121

Asp Ala Pro Gly His Gly Asp Gly Xaa Asp Glu Asn Xaa Gly Xaa
1               5                   10                  15

<210> SEQ ID NO 122
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 122

Leu Xaa Xaa Trp Ala Xaa Glu Gln Arg Gly Xaa Leu Xaa Asn Xaa Xaa
1               5                   10                  15

Xaa Ser Thr Thr Val
        20

<210> SEQ ID NO 123
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 123

Ala Xaa Glu Asn Gln Arg Gly Phe Ile Met Val Leu Gly Leu Xaa Asn
1               5                   10                  15

Xaa Xaa Xaa Ser Thr Ala Thr Val
        20

<210> SEQ ID NO 124
<211> LENGTH: 18
<212> TYPE: PRT
<213> ORGANISM: Artificial Sequence
<220> FEATURE:
<223> OTHER INFORMATION: Polypeptide
<220> FEATURE:
```

```
<221> NAME/KEY: VARIANT
<222> LOCATION: (1)...(18)
<223> OTHER INFORMATION: Xaa = any amino acid

<400> SEQUENCE: 124

Trp Ala Xaa Glu Gln Arg Gly Xaa Leu Xaa Asn Xaa Xaa Xaa Ser Thr
 1               5                  10                  15

Thr Val

<210> SEQ ID NO 125
<211> LENGTH: 13
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(13)
<223> OTHER INFORMATION: Xaa = any amino acid

<400> SEQUENCE: 125

Ile Xaa Gly Gln Asp Pro Tyr Xaa Gly Asn Gln Ser Thr
 1               5                  10

<210> SEQ ID NO 126
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 126

Leu Xaa Ala Xaa Glu Gln Arg Gly Xaa Leu Gly Ile Leu Xaa Asn Thr
 1               5                  10                  15

Xaa Xaa Xaa Ser Thr Val
            20

<210> SEQ ID NO 127
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 127

Trp Ala Xaa Xaa Gly Xaa Leu Xaa Asn Xaa Xaa Xaa Ser Thr Thr Val
 1               5                  10                  15

<210> SEQ ID NO 128
<211> LENGTH: 11
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(11)
<223> OTHER INFORMATION: Xaa = any amino acid

<400> SEQUENCE: 128

Gly Gln Asp Pro Tyr Xaa Gly Asn Gln Ser Thr
```

```
<210> SEQ ID NO 129
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 129

Glu Xaa Xaa Xaa Xaa Arg Xaa Gln Xaa Phe Tyr Xaa Gly Xaa Cys Val
 1               5                  10                  15

Ile Leu Met Xaa Xaa Xaa Gly Asn Xaa Gly
            20                  25

<210> SEQ ID NO 130
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 130

Val Arg Xaa Xaa Xaa Xaa Tyr Xaa Arg Xaa Xaa Xaa Gly Lys
 1               5                  10

<210> SEQ ID NO 131
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 131

Arg Xaa Xaa Xaa Xaa Tyr Ile Leu Met Arg Xaa Xaa Xaa Gly Lys
 1               5                  10                  15

<210> SEQ ID NO 132
<211> LENGTH: 60
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(60)
<223> OTHER INFORMATION: Xaa = any amino acid

<400> SEQUENCE: 132

Thr Gly Xaa Glu Met Glu Ala Ile Leu Val Xaa Ala Cys Gly Ser Ala
 1               5                  10                  15

Thr Val Asn Gln Ser Thr Xaa Ala Cys Gly Ser Thr Xaa Xaa Ala Asn
            20                  25                  30

Thr Val Ile Leu Val Trp Tyr Asp Met Xaa Lys Xaa Xaa Asp Glu Gln
        35                  40                  45

Ser Xaa Ala Asp Glu Gly Ser Xaa Xaa Gly Ile Val
        50                  55                  60
```

-continued

```
            50                  55                  60

<210> SEQ ID NO 133
<211> LENGTH: 59
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(59)
<223> OTHER INFORMATION: Xaa = any amino acid

<400> SEQUENCE: 133

Gly Xaa Glu Met Glu Ala Ile Leu Val Xaa Ala Cys Gly Ser Ala Thr
1               5                   10                  15

Val Asn Gln Ser Thr Xaa Ala Cys Gly Ser Thr Xaa Xaa Ala Asn Thr
            20                  25                  30

Val Ile Leu Val Trp Tyr Asp Met Xaa Lys Xaa Xaa Asp Glu Gln Ser
        35                  40                  45

Xaa Ala Asp Glu Gly Ser Xaa Xaa Gly Ile Val
    50                  55

<210> SEQ ID NO 134
<211> LENGTH: 57
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(57)
<223> OTHER INFORMATION: Xaa = any amino acid

<400> SEQUENCE: 134

Glu Met Glu Ala Ile Leu Val Xaa Ala Cys Gly Ser Ala Thr Val Asn
1               5                   10                  15

Gln Ser Thr Xaa Ala Cys Gly Ser Thr Xaa Xaa Ala Asn Thr Val Ile
            20                  25                  30

Leu Val Trp Tyr Asp Met Xaa Lys Xaa Xaa Asp Glu Gln Ser Xaa Ala
        35                  40                  45

Asp Glu Gly Ser Xaa Xaa Gly Ile Val
    50                  55

<210> SEQ ID NO 135
<211> LENGTH: 58
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(58)
<223> OTHER INFORMATION: Xaa = any amino acid

<400> SEQUENCE: 135

Gly Xaa Met Glu Ala Ile Leu Val Xaa Ala Cys Gly Ser Ala Thr Val
1               5                   10                  15

Asn Gln Ser Thr Xaa Ala Cys Gly Ser Thr Xaa Xaa Ala Asn Thr Val
            20                  25                  30

Ile Leu Val Trp Tyr Asp Met Xaa Lys Xaa Xaa Asp Glu Gln Ser Xaa
        35                  40                  45

Ala Asp Glu Gly Ser Xaa Xaa Gly Ile Val
    50                  55
```

<210> SEQ ID NO 136
<211> LENGTH: 56
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(56)
<223> OTHER INFORMATION: Xaa = any amino acid

<400> SEQUENCE: 136

Met Glu Ala Ile Leu Val Xaa Ala Cys Gly Ser Ala Thr Val Asn Gln
 1               5                  10                  15

Ser Thr Xaa Ala Cys Gly Ser Thr Xaa Xaa Ala Asn Thr Val Ile Leu
            20                  25                  30

Val Trp Tyr Asp Met Xaa Lys Xaa Xaa Asp Glu Gln Ser Xaa Ala Asp
        35                  40                  45

Glu Gly Ser Xaa Xaa Gly Ile Val
    50                  55

<210> SEQ ID NO 137
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 137

Leu Xaa Xaa Xaa Asp Met Xaa Lys Xaa Xaa Asp Glu Gln Ser Xaa Ala
 1               5                  10                  15

Asp Glu Gly Ser Xaa Xaa Gly Ile Val
            20                  25

<210> SEQ ID NO 138
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 138

Gly Xaa Tyr Xaa Gly Xaa Ile Val Xaa Xaa Phe Leu Val Ala Asp Glu
 1               5                  10                  15

Thr Xaa Xaa Arg Xaa Xaa Gly Ile
            20

<210> SEQ ID NO 139
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 139

-continued

Tyr Xaa Gly Xaa Ile Val Xaa Xaa Phe Leu Val Ala Asp Glu Thr Xaa
1               5                   10                  15

Xaa Arg Xaa Xaa Gly Ile
        20

<210> SEQ ID NO 140
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 140

Gly Xaa Ile Val Xaa Xaa Phe Leu Val Ala Asp Glu Thr Xaa Xaa Arg
1               5                   10                  15

Xaa Xaa Gly Ile
        20

<210> SEQ ID NO 141
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 141

Cys Xaa Phe His Tyr Xaa Leu Pro Ser Thr Cys Ser Xaa Tyr Xaa Xaa
1               5                   10                  15

Xaa Xaa Phe Ile Leu Val Xaa Xaa Gly Asn Pro Ser
        20                  25

<210> SEQ ID NO 142
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 142

Pro Gly Gly Cys Asp Xaa Xaa Gly Xaa Arg Xaa Xaa Xaa Xaa Phe His
1               5                   10                  15

Xaa Xaa Xaa Phe Ile Leu Met Xaa Xaa Xaa Gly
        20                  25

<210> SEQ ID NO 143
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 143

```
Gly Gly Cys Asp Xaa Xaa Gly Xaa Arg Xaa Xaa Xaa Xaa Phe His Xaa
 1               5                  10                  15

Xaa Xaa Phe Ile Leu Met Xaa Xaa Xaa Gly
            20                  25
```

<210> SEQ ID NO 144
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 144

```
Pro Gly Gly Xaa Xaa Xaa Gly Xaa Arg Xaa Xaa Xaa Xaa Phe His Xaa
 1               5                  10                  15

Xaa Xaa Phe Ile Leu Met Xaa Xaa Xaa Gly
            20                  25
```

<210> SEQ ID NO 145
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 145

```
Gly Gly Xaa Xaa Xaa Gly Xaa Arg Xaa Xaa Xaa Xaa Phe His Xaa Xaa
 1               5                  10                  15

Xaa Phe Ile Leu Met Xaa Xaa Xaa Gly
            20                  25
```

<210> SEQ ID NO 146
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid

<400> SEQUENCE: 146

```
Ile Ala Gly Val Xaa Ala Gly Xaa Ala Glu Ser Ala Gly Xaa Leu Xaa
 1               5                  10                  15

Xaa Xaa Xaa Ala Xaa Xaa Xaa Pro Val Phe Ile Leu Ala Gly Val Pro
            20                  25                  30
```

<210> SEQ ID NO 147
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 147

Ala Gly Xaa Ala Glu Ser Ala Gly Xaa Leu Xaa Xaa Xaa Xaa Ala Xaa
1               5                   10                  15

Xaa Xaa Pro Val Phe Ile Leu Ala Gly Val Pro
            20                  25

<210> SEQ ID NO 148
<211> LENGTH: 38
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(38)
<223> OTHER INFORMATION: Xaa = any amino acid

<400> SEQUENCE: 148

Ile Xaa Xaa Ala Gly Xaa Ala Glu Ser Ala Gly Xaa Leu Xaa Xaa Xaa
1               5                   10                  15

Xaa Ala Ala Gly Asn Ser Xaa Xaa Xaa Pro Val Ile Val Xaa Ala
            20                  25                  30

Gly Val Pro Val Pro Val
        35

<210> SEQ ID NO 149
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 149

Gly Xaa Ala Glu Ser Ala Gly Xaa Leu Xaa Xaa Xaa Xaa Ala Xaa Xaa
1               5                   10                  15

Xaa Pro Val Phe Ile Leu Ala Gly Val Pro
            20                  25

<210> SEQ ID NO 150
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 150

Ala Xaa Xaa Xaa Xaa Pro Val Phe Ile Leu Ala Gly Val Pro
1               5                   10

<210> SEQ ID NO 151
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 151

```
Ser Xaa Gly Ile Met Xaa Cys Ala Gly Ser Xaa Xaa Asp Glu Ile Leu
 1               5                  10                  15
```

<210> SEQ ID NO 152
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 152

```
Gly Xaa Asp Xaa Xaa Ala Gly Asn Ser Gly Ala Gly Ser Gly Xaa Xaa
 1               5                  10                  15

Ala Thr Asp Ile Leu Met Xaa Ala Ser Thr Val
                20                  25
```

<210> SEQ ID NO 153
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 153

```
Gly Xaa Asp Xaa Xaa Ala Gly Asn Ser Gly Ala Gly Ser Gly Xaa Xaa
 1               5                  10                  15

Ala Thr Asp Ile Leu Met Xaa Ala Ser Thr Val
                20                  25
```

<210> SEQ ID NO 154
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 154

```
Gly Xaa Asp Xaa Xaa Xaa Gly Ala Gly Ser Gly Xaa Xaa Ala Thr Asp
 1               5                  10                  15

Ile Leu Met Xaa Ala Ser Thr Val
                20
```

<210> SEQ ID NO 155
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 155

```
Asp Xaa Xaa Ala Gly Asn Ser Gly Ala Gly Ser Gly Xaa Xaa Ala Thr
 1               5                  10                  15
```

```
Asp Ile Leu Met Xaa Ala Ser Thr Val
            20                  25

<210> SEQ ID NO 156
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 156

Gly Xaa Asp Xaa Xaa Gly Gly Xaa Xaa Xaa Asp Ile Leu Met Xaa Ala
1               5                   10                  15

Ser Thr Val

<210> SEQ ID NO 157
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 157

Gly Gly Gly Ser Thr Gly Ala Ser Thr Gly Ala Cys Gly Ser Ala Ser
1               5                   10                  15

Thr Pro Xaa Phe Ile Leu Val Ala Ser Val
            20                  25

<210> SEQ ID NO 158
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 158

Gly Gly Gly Thr Gly Ala Ser Thr Ala Gly Xaa Ala Ser Thr Val Ile
1               5                   10                  15

Pro Val

<210> SEQ ID NO 159
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 159

His Xaa Asp Asn Ala Ile Leu Val Xaa Ala Pro Xaa Xaa Xaa Gly Gly
1               5                   10                  15

Asn
```

-continued

```
<210> SEQ ID NO 160
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 160

Asn Leu Xaa Lys Arg Gly Ala Xaa Xaa Ala Xaa Xaa Ala Cys Asn Ser
1               5                   10                  15

Xaa Asp Glu Asn Xaa Xaa Xaa Asp Gly Asn Ser
            20                  25

<210> SEQ ID NO 161
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 161

Asp Asn Leu Gly Xaa Xaa Ala Xaa Xaa Ala Cys Asn Ser Val Xaa Cys
1               5                   10                  15

Asn Val Xaa Xaa Xaa Asp Glu Gly Asn
            20                  25

<210> SEQ ID NO 162
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 162

Glu Ala Asp Asp Xaa Ala Ile Leu Val Ala Gly Xaa Xaa Ala Asp Ser
1               5                   10                  15

Thr Val

<210> SEQ ID NO 163
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 163

Gly Xaa Ile Val Ala Cys Gly Thr Val Ile Leu Val Asp Asn Gly Xaa
1               5                   10                  15

Ser Leu Thr Ile Leu Val
            20
```

```
<210> SEQ ID NO 164
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 164

Gly Ser Phe Ile Val Ala Cys Gly Ser Thr Val Xaa Asp Asn Gly Xaa
 1               5                  10                  15

Cys Ser Leu Thr Ile Leu Val
            20

<210> SEQ ID NO 165
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 165

Ser Phe Ile Val Ala Cys Gly Ser Thr Val Xaa Asp Asn Gly Xaa Cys
 1               5                  10                  15

Ser Leu Thr Ile Leu Val
            20

<210> SEQ ID NO 166
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 166

Gly Ala Asp Glu Ser Ser Phe Ile Val Ala Ser Xaa Ala Asp Gly Asn
 1               5                  10                  15

Gln Gly Xaa Cys Xaa Thr
            20

<210> SEQ ID NO 167
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 167

Gly His Phe Ile Leu Val Leu Met Val Xaa Gly His Ile Val Xaa Xaa
 1               5                  10                  15

Xaa Ala Gly Thr Val Xaa Phe Ile Leu Val
            20                  25
```

```
<210> SEQ ID NO 168
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 168

Ser Ala Asn Ser Gly Xaa His Ala Ser Thr Asn Gly Xaa Ser Thr Xaa
 1               5                  10                  15

Ala Ile Val Arg Xaa Ala Ile Leu Val
            20                  25

<210> SEQ ID NO 169
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 169

Ser Gly Xaa His Ala Ser Thr Asn Gly Xaa Ser Thr Xaa Ala Ile Val
 1               5                  10                  15

Arg Xaa Ala Ile Leu Val
            20

<210> SEQ ID NO 170
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 170

Gly Xaa His Ala Ser Thr Asn Gly Xaa Ser Thr Xaa Ala Ile Val Arg
 1               5                  10                  15

Xaa Ala Ile Leu Val
            20

<210> SEQ ID NO 171
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 171

Gly Xaa His Ala Ser Thr Val Asn Gly Xaa Ser Thr Xaa Ala Ile Val
 1               5                  10                  15

Arg Xaa Ala Ile Leu Val
            20
```

```
<210> SEQ ID NO 172
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 172

Gly Gly Glu Thr Ala Xaa Xaa Gly Pro Asp Glu Gly Ser Phe Ile Leu
 1               5                  10                  15

Met Val

<210> SEQ ID NO 173
<211> LENGTH: 13
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(13)
<223> OTHER INFORMATION: Xaa = any amino acid

<400> SEQUENCE: 173

Asp Gly Ile Val Gly Ser Thr Lys Xaa Xaa Ile Leu Val
 1               5                  10

<210> SEQ ID NO 174
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 174

Gly Glu Thr Ala Xaa Xaa Gly Pro Asp Glu Gly Ser Phe Ile Leu Met
 1               5                  10                  15

Val

<210> SEQ ID NO 175
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 175

Glu Xaa Ala Ser Xaa Arg Pro Thr Val His Asp Asn Ser Thr Gly Xaa
 1               5                  10                  15

Xaa Ser Thr

<210> SEQ ID NO 176
<211> LENGTH: 17
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(17)
<223> OTHER INFORMATION: Xaa = any amino acid

<400> SEQUENCE: 176

Glu Xaa Ala Ser Xaa Arg Xaa His Asp Asn Ser Thr Gly Xaa Xaa Ser
 1               5                  10                  15

Thr

<210> SEQ ID NO 177
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 177

Arg Pro Thr Val His Asp Asn Ser Thr Gly Xaa Xaa Ser Thr
 1               5                  10

<210> SEQ ID NO 178
<211> LENGTH: 83
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(83)
<223> OTHER INFORMATION: Xaa = any amino acid

<400> SEQUENCE: 178

Arg Gly Arg Ser Thr Phe Ile Leu Xaa Xaa Xaa Xaa Ile Leu Met Val
 1               5                  10                  15

Phe Ile Leu Val Ile Leu Val Asp Asp Glu Ala Cys Ser Val Gln Glu
             20                  25                  30

Asn Ser Xaa Glu Pro Gln Ser Thr Xaa Xaa Xaa Ile Leu Met Val Xaa
         35                  40                  45

Xaa Phe Ile Leu Val Ile Leu Val Xaa Arg Xaa Gly Xaa Xaa Ala Gly
     50                  55                  60

Ser Thr Val Xaa Xaa Ile Val Xaa Xaa Xaa Asp Asn Xaa Xaa Xaa Xaa
65                  70                  75                  80

Asp Arg Ser

<210> SEQ ID NO 179
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 179

Gly Xaa Ala Thr Gly Cys Ser Thr Gly Lys Ser Thr Xaa Phe Ile Leu
 1               5                  10                  15

Met Ala Ser Thr Xaa Ala Cys Ser Thr Val Xaa Ala Gly
             20                  25
```

<210> SEQ ID NO 180
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid

<400> SEQUENCE: 180

Asn Xaa Xaa Xaa Gly Leu Pro Val Xaa Xaa Gly Phe Trp Tyr Xaa Xaa
 1               5                  10                  15

Xaa Leu Met Xaa Ile Leu Met Val Xaa Xaa Xaa Xaa Phe Tyr
            20                  25                  30

<210> SEQ ID NO 181
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 181

Leu His Tyr Gln Ile Leu Met Val Xaa Gly Arg Xaa Ala Gly Ser Arg
 1               5                  10                  15

Xaa Xaa Xaa Xaa Ala Gly Gln Ser
            20

<210> SEQ ID NO 182
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 182

Leu His Tyr Gln Xaa Xaa Gly Arg Xaa Ala Gly Ser Arg Xaa Xaa Xaa
 1               5                  10                  15

Xaa Ala Gly Gln Ser
            20

<210> SEQ ID NO 183
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 183

Leu Xaa Gln Ile Leu Met Val Xaa Gly Arg Xaa Ala Gly Ser Arg Xaa
 1               5                  10                  15

Xaa Xaa Xaa Ala Gly Gln Ser
            20

```
<210> SEQ ID NO 184
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 184

Gly Xaa Xaa Xaa Leu Xaa Gln Thr Ile Leu Met Xaa Gly Asn Arg Xaa
 1               5                  10                  15

Xaa Asn Arg Xaa Xaa Xaa Xaa Ala Gly Asn Gln Ser
            20                  25

<210> SEQ ID NO 185
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 185

Asp Ile Leu Val Gly Ala Ser Thr Gly Xaa Gly Xaa Pro Ala Gly Ser
 1               5                  10                  15

Val Ile Leu Val
            20

<210> SEQ ID NO 186
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 186

Asp Ala Ile Leu Val Gly Ala Ser Thr Gly Xaa Gly Xaa Pro Ala Gly
 1               5                  10                  15

Ser Val Ile Leu Val
            20

<210> SEQ ID NO 187
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: v

<400> SEQUENCE: 187

Arg Arg Arg Xaa Cys Xaa Xaa Cys Xaa Xaa Arg Phe Tyr Gly Ser Thr
 1               5                  10                  15

Thr Xaa Glu
```

```
<210> SEQ ID NO 188
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 188

Arg Arg Arg Xaa Cys Xaa Xaa Cys Xaa Xaa Arg Phe Tyr Gly Ser Thr
 1               5                  10                  15

Thr Xaa Glu

<210> SEQ ID NO 189
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 189

Arg Arg Arg Xaa Cys Xaa Xaa Cys Xaa Xaa Arg Xaa Thr Thr Xaa Glu
 1               5                  10                  15

<210> SEQ ID NO 190
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 190

Arg Arg Arg Xaa Cys Xaa Xaa Cys Xaa Xaa Arg Xaa Thr Xaa Glu
 1               5                  10                  15

<210> SEQ ID NO 191
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 191

Arg Arg Xaa Cys Xaa Xaa Cys Xaa Xaa Arg Xaa Thr Thr Xaa Glu
 1               5                  10                  15

<210> SEQ ID NO 192
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid
```

<400> SEQUENCE: 192

Leu Xaa Cys Thr His Phe Tyr Xaa Xaa Phe Ile Leu Met Val Xaa Xaa
1               5                   10                  15

Xaa Phe Ile Leu
            20

<210> SEQ ID NO 193
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 193

Cys Thr His Phe Tyr Xaa Xaa Phe Ile Leu Met Val Xaa Xaa Xaa Phe
1               5                   10                  15

Ile Leu

<210> SEQ ID NO 194
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 194

Gly Arg Asp Xaa Gly Thr Xaa Xaa Ile Leu Val Xaa Xaa Xaa Ala Ser
1               5                   10                  15

Xaa Xaa Lys Arg Xaa Phe Tyr Ile Leu Met Val Xaa Ala Ser Thr Xaa
                20                  25                  30

Xaa Xaa Xaa Arg Ala Val Xaa Arg Lys Arg Xaa Xaa Asp Glu Gln
            35                  40                  45

<210> SEQ ID NO 195
<211> LENGTH: 36
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(36)
<223> OTHER INFORMATION: Xaa = any amino acid

<400> SEQUENCE: 195

Asp Gly Pro Val Ala Gly Ser Thr Ala Gly Ser Ala Ser Thr Val Gly
1               5                   10                  15

Lys Gly Ser Ser Thr Xaa Ala Cys Gly Ser Thr Xaa Xaa Ile Leu Met
                20                  25                  30

Val Ala Gly Ser
            35

<210> SEQ ID NO 196
<211> LENGTH: 35
<212> TYPE: PRT
<213> ORGANISM: Artificial Sequence
<220> FEATURE:

```
<223> OTHER INFORMATION: Polypeptide
<220> FEATURE:
<221> NAME/KEY: VARIANT
<222> LOCATION: (1)...(35)
<223> OTHER INFORMATION: Xaa = any amino acid

<400> SEQUENCE: 196

Asp Gly Xaa Ala Gly Ser Thr Ala Gly Ser Ala Ser Thr Val Gly Lys
 1               5                  10                  15
Gly Ser Ser Thr Xaa Ala Cys Gly Ser Thr Xaa Xaa Ile Leu Met Val
            20                  25                  30
Ala Gly Ser
         35

<210> SEQ ID NO 197
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid

<400> SEQUENCE: 197

Asp Gly Xaa Xaa Ala Gly Ser Ala Ser Thr Val Gly Lys Gly Ser Ser
 1               5                  10                  15
Thr Xaa Ala Cys Gly Ser Thr Xaa Xaa Ile Leu Met Val Ala Gly Ser
            20                  25                  30

<210> SEQ ID NO 198
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid

<400> SEQUENCE: 198

Asp Gly Xaa Xaa Xaa Ala Ser Thr Val Gly Lys Gly Ser Ser Thr Xaa
 1               5                  10                  15
Ala Cys Gly Ser Thr Xaa Xaa Ile Leu Met Val Ala Gly Ser
            20                  25                  30

<210> SEQ ID NO 199
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 199

Asp Gly Xaa Xaa Xaa Xaa Gly Lys Gly Ser Ser Thr Xaa Ala Cys Gly
 1               5                  10                  15
Ser Thr Xaa Xaa Ile Leu Met Val Ala Gly Ser
            20                  25

<210> SEQ ID NO 200
<211> LENGTH: 26
```

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 200

Asp Gly Xaa Xaa Xaa Gly Lys Gly Ser Ser Thr Xaa Ala Cys Gly Ser
 1               5                  10                  15

Thr Xaa Xaa Ile Leu Met Val Ala Gly Ser
            20                  25

<210> SEQ ID NO 201
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 201

Gly Ala Ser Thr Xaa Gly Lys Thr Thr Ala Ser Thr Val Xaa Xaa Ile
 1               5                  10                  15

Leu Met Val Xaa Xaa Xaa Phe Ile Leu Met Val
            20                  25

<210> SEQ ID NO 202
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 202

Gly Ala Ser Thr Xaa Gly Lys Ala Ser Thr Gly Ser Thr Thr Val Ala
 1               5                  10                  15

Ser Thr Xaa Phe Ile Leu Met
            20

<210> SEQ ID NO 203
<211> LENGTH: 35
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(35)
<223> OTHER INFORMATION: Xaa = any amino acid

<400> SEQUENCE: 203

Glu Ile Leu Met Val Ile Phe Ile Leu Val Ala Xaa Ala Asp Gly Asn
 1               5                  10                  15

Pro Ser Thr Xaa Asn Ser Thr Xaa Ala Asp Glu Asn Gly Asn Ser Asp
            20                  25                  30

Glu Asn Gln
        35
```

<210> SEQ ID NO 204
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid

<400> SEQUENCE: 204

```
Leu Ala Ala Gly Xaa Gly Ser Xaa Arg Phe Ile Met Xaa Ser Xaa Xaa
 1               5                  10                  15

Xaa Lys Thr Val Leu Met Xaa Xaa Ile Leu Val Xaa Asp Gly Gln Xaa
            20                  25                  30

Xaa Leu Met Ile Leu Val Xaa Xaa Xaa Phe Ile Leu Val
        35                  40                  45
```

<210> SEQ ID NO 205
<211> LENGTH: 44
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(44)
<223> OTHER INFORMATION: Xaa = any amino acid

<400> SEQUENCE: 205

```
Ala Ala Gly Xaa Gly Ser Xaa Arg Phe Ile Met Xaa Ser Xaa Xaa Xaa
 1               5                  10                  15

Lys Thr Val Leu Met Xaa Xaa Ile Leu Val Xaa Asp Gly Gln Xaa Xaa
            20                  25                  30

Leu Met Ile Leu Val Xaa Xaa Xaa Phe Ile Leu Val
        35                  40
```

<210> SEQ ID NO 206
<211> LENGTH: 43
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(43)
<223> OTHER INFORMATION: Xaa = any amino acid

<400> SEQUENCE: 206

```
Ala Gly Xaa Gly Ser Xaa Arg Phe Ile Met Xaa Ser Xaa Xaa Xaa Lys
 1               5                  10                  15

Thr Val Leu Met Xaa Xaa Ile Leu Val Xaa Asp Gly Gln Xaa Xaa Leu
            20                  25                  30

Met Ile Leu Val Xaa Xaa Xaa Phe Ile Leu Val
        35                  40
```

<210> SEQ ID NO 207
<211> LENGTH: 42
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(42)
<223> OTHER INFORMATION: Xaa = any amino acid

```
<400> SEQUENCE: 207

Gly Xaa Gly Ser Xaa Arg Phe Ile Met Xaa Ser Xaa Xaa Xaa Lys Thr
1               5                   10                  15

Val Leu Met Xaa Xaa Ile Leu Val Xaa Asp Gly Gln Xaa Xaa Leu Met
            20                  25                  30

Ile Leu Val Xaa Xaa Xaa Phe Ile Leu Val
            35                  40

<210> SEQ ID NO 208
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)
<223> OTHER INFORMATION: Xaa = any amino acid

<400> SEQUENCE: 208

Gly Xaa Arg Phe Ile Met Xaa Ser Xaa Xaa Xaa Lys Thr Val Leu Met
1               5                   10                  15

Xaa Xaa Ile Leu Val Xaa Asp Gly Gln Xaa Xaa Leu Met Ile Leu Val
            20                  25                  30

Xaa Xaa Xaa Phe Ile Leu Val
            35

<210> SEQ ID NO 209
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 209

Arg Phe Ile Met Xaa Ser Xaa Xaa Xaa Lys Thr Val Leu Met Xaa Xaa
1               5                   10                  15

Ile Leu Val Xaa Asp Gly Gln Xaa Xaa Leu Met Ile Leu Val Xaa Xaa
            20                  25                  30

Xaa Phe Ile Leu Val
            35

<210> SEQ ID NO 210
<211> LENGTH: 46
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(46)
<223> OTHER INFORMATION: Xaa = any amino acid

<400> SEQUENCE: 210

Cys Xaa Xaa Xaa Xaa Thr Ala Gly Asn Ser Thr Ser Thr Xaa Ala Gly
1               5                   10                  15

Asn Gln Ser Thr Xaa Xaa Xaa Asp Glu Xaa Leu Met Gly Phe Ile Leu
            20                  25                  30

Met Val Xaa Xaa Xaa Xaa Ala Cys Asn Ser Thr Ala Gly Ser
            35                  40                  45
```

<210> SEQ ID NO 211
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 211

Gly Ser Ser Thr Asn Xaa Xaa Xaa His Xaa Xaa Ala Xaa Ala Ser
 1               5                  10                  15

<210> SEQ ID NO 212
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 212

Cys Asp Lys Xaa Xaa Pro Ala Gly Ser Xaa Xaa Ile Leu Met Ala Gly
 1               5                  10                  15

<210> SEQ ID NO 213
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 213

Glu Xaa His His Xaa Xaa Lys Xaa Asp Xaa Ile Leu Pro Ser Gly Ser
 1               5                  10                  15

Thr Ala Gly Leu
            20

<210> SEQ ID NO 214
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 214

His His Xaa Xaa Lys Xaa Asp Xaa Ile Leu Pro Ser Gly Ser Thr Ala
 1               5                  10                  15

Gly Leu

<210> SEQ ID NO 215
<211> LENGTH: 20
<212> TYPE: PRT
<213> ORGANISM: Artificial Sequence
<220> FEATURE:

<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 215

Glu Xaa His Xaa Xaa Xaa Lys Xaa Asp Xaa Ile Leu Pro Ser Gly Ser
 1               5                  10                  15

Thr Ala Gly Leu
            20

<210> SEQ ID NO 216
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 216

His Xaa Xaa Lys Xaa Asp Xaa Ile Leu Pro Ser Gly Ser Thr Ala Gly
 1               5                  10                  15

Leu

<210> SEQ ID NO 217
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 217

Glu Thr Gly Ala Gly Xaa His Trp Gly Xaa Ala Xaa Xaa Xaa Ala
 1               5                  10                  15

<210> SEQ ID NO 218
<211> LENGTH: 13
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(13)
<223> OTHER INFORMATION: Xaa = any amino acid

<400> SEQUENCE: 218

Glu Thr Gly Ala Gly Xaa His Trp Gly Xaa Ala Xaa Ala
 1               5                  10

<210> SEQ ID NO 219
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 219

```
Thr Gly Ala Gly Xaa His Trp Gly Xaa Ala Xaa Xaa Xaa Ala
1               5                   10
```

<210> SEQ ID NO 220
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 220

```
Gly Xaa Xaa Xaa Ala Xaa Glu Pro Ser Thr Ala Cys Asn Ser His Ala
1               5                   10                  15
Phe Ile Leu Val Xaa Xaa Ala Leu Val
            20                  25
```

<210> SEQ ID NO 221
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(12)
<223> OTHER INFORMATION: Xaa = any amino acid

<400> SEQUENCE: 221

```
Thr Gly Ala Gly Xaa His Trp Gly Xaa Ala Xaa Ala
1               5                   10
```

<210> SEQ ID NO 222
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 222

```
Gly Xaa Xaa Xaa Ala Glu Pro Ser Thr Ala Cys Asn Ser His Ala Phe
1               5                   10                  15
Ile Leu Val Xaa Xaa Ala Leu Val
            20
```

<210> SEQ ID NO 223
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 223

```
Gly Xaa Xaa Ala Xaa Glu Pro Ser Thr Ala Cys Asn Ser His Ala Phe
1               5                   10                  15
Ile Leu Val Xaa Xaa Ala Leu Val
            20
```

```
<210> SEQ ID NO 224
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 224

Gly His Xaa Pro Xaa Xaa Ala Pro Xaa Xaa Pro Gly Val Xaa Ile Leu
 1               5                  10                  15

Met Xaa Glu Xaa Xaa Ala Ala Gln Ser Thr
             20                  25

<210> SEQ ID NO 225
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 225

His Xaa Pro Xaa Xaa Ala Pro Xaa Xaa Pro Gly Val Xaa Ile Leu Met
 1               5                  10                  15

Xaa Glu Xaa Xaa Ala Ala Gln Ser Thr
             20                  25

<210> SEQ ID NO 226
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 226

His Xaa Pro Xaa Xaa Xaa Xaa Xaa Pro Gly Val Xaa Ile Leu Met Xaa
 1               5                  10                  15

Glu Xaa Xaa Ala Ala Gln Ser Thr
             20

<210> SEQ ID NO 227
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 227

Pro Xaa Xaa Ala Pro Xaa Xaa Pro Gly Val Xaa Ile Leu Met Xaa Glu
 1               5                  10                  15

Xaa Xaa Ala Ala Gln Ser Thr
             20
```

<210> SEQ ID NO 228
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 228

Pro Gly Val Xaa Ile Leu Met Xaa Glu Xaa Xaa Ala Ala Gln Ser Thr
1               5                   10                  15

<210> SEQ ID NO 229
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(12)
<223> OTHER INFORMATION: Xaa = any amino acid

<400> SEQUENCE: 229

Gly His Arg Phe Tyr Glu Ala Gly Xaa Asp Xaa Arg
1               5                   10

<210> SEQ ID NO 230
<211> LENGTH: 80
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(80)
<223> OTHER INFORMATION: Xaa = any amino acid

<400> SEQUENCE: 230

Asp Glu Ile Met Val Asp Xaa Gly Asn Ile Leu Val Gly Ser Gly Xaa
1               5                   10                  15

Xaa Ala Gly Ser Xaa Xaa Ile Met Val Ala Gly Ser Xaa Xaa Ile Leu
            20                  25                  30

Met Xaa Xaa Ile Leu Val Ala Gly Ser Xaa Xaa Xaa Gln Ile Leu Val
        35                  40                  45

Phe Ile Leu Met Val Ala Cys Ser Thr Val Ile Val Ser Thr His Xaa
    50                  55                  60

Ala Pro Val Xaa Ile Leu Val Xaa Ala Cys Gly Ser Xaa Ala Gly Ser
65                  70                  75                  80

<210> SEQ ID NO 231
<211> LENGTH: 44
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(44)
<223> OTHER INFORMATION: Xaa = any amino acid

<400> SEQUENCE: 231

Gly Xaa Ser Thr Gly Ala Ser Thr Val Gly Lys Ser Thr Ile Leu Met
1               5                   10                  15

Val Xaa Phe Ile Leu Val Xaa Ala Gly Ser Ile Leu Met Xaa Xaa Xaa
            20                  25                  30

Xaa Gly Ser Xaa Xaa Xaa Asp Glu Gly Asn Ser Thr
        35                  40

<210> SEQ ID NO 232
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 232

Ser Gly Glu Xaa Ala Asn Ser Arg Phe Ile Leu Met Val Xaa Leu Ala
1               5                   10                  15

Ser Phe Ile Leu Met Val
            20

<210> SEQ ID NO 233
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 233

Ser Xaa Gly Glu Xaa Ala Asn Ser Arg Phe Ile Leu Met Val Xaa Leu
1               5                   10                  15

Ala Ser Phe Ile Leu Met Val
            20

<210> SEQ ID NO 234
<211> LENGTH: 43
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(43)
<223> OTHER INFORMATION: Xaa = any amino acid

<400> SEQUENCE: 234

Lys Xaa Ile Leu Pro Xaa Xaa Ala Gly Ser Gly Xaa Gly Gly Ser Ala
1               5                   10                  15

Asp Asn Ser Thr Ala Asp Asn Xaa Ala Gly Thr Ala Gly Ser Thr Val
            20                  25                  30

Xaa Phe Leu Met Val Xaa Xaa Ile Leu Met Val
        35                  40

<210> SEQ ID NO 235
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)

<223> OTHER INFORMATION: Xaa = any amino acid

<400> SEQUENCE: 235

Pro Xaa Xaa Ala Gly Ser Gly Xaa Gly Gly Ser Ala Asp Asn Ser Thr
1               5                   10                  15

Ala Asp Asn Xaa Ala Gly Thr Ala Gly Ser Thr Val Xaa Phe Leu Met
            20                  25                  30

Val Xaa Xaa Ile Leu Met Val
        35

<210> SEQ ID NO 236
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 236

Gly Phe Ile Leu Met Val Ala Gly Gly Ser Xaa Xaa Ala Ala Gly
1               5                   10                  15

Ser Thr Val Xaa Ala Ile Leu Val
            20

<210> SEQ ID NO 237
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 237

Gly Xaa Gly Gly Ser Ala Asp Asn Ser Thr Ala Asp Asn Xaa Ala Gly
1               5                   10                  15

Thr Ala Gly Ser Thr Val Xaa Phe Leu Met Val Xaa Xaa Ile Leu Met
            20                  25                  30

Val

<210> SEQ ID NO 238
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid

<400> SEQUENCE: 238

Gly Ala Cys Thr Val Ile Leu Val Ile Val Xaa Gly Ala Asp Glu Gly
1               5                   10                  15

Asn Gln Ser Thr Xaa His Xaa Xaa Xaa Ile Val Ala Cys Ser Val Xaa
            20                  25                  30

Xaa Xaa Ala Gly Asn Ser Thr Xaa Xaa Ile Leu Met Val
        35                  40                  45

<210> SEQ ID NO 239

```
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid

<400> SEQUENCE: 239

Asp Ile Val Ala Ile Leu Val Ile Val Ala Cys Ser Thr Val Asp Glu
 1               5                   10                  15

Gly Phe Tyr Xaa Gly Asn Xaa Xaa Leu Lys Xaa Xaa Glu Gly
            20                  25                  30

<210> SEQ ID NO 240
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 240

Gly Phe Tyr Xaa Gly Asn Xaa Xaa Leu Lys Xaa Xaa Glu Gly
 1               5                   10

<210> SEQ ID NO 241
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 241

Val Ala Cys Ser Thr Val Xaa Gly Xaa Asn Xaa Xaa Leu Lys Xaa Xaa
 1               5                   10                  15

Glu Gly Ala Gly Ser
            20

<210> SEQ ID NO 242
<211> LENGTH: 10
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(10)
<223> OTHER INFORMATION: Xaa = any amino acid

<400> SEQUENCE: 242

Gly Asn Xaa Xaa Leu Lys Xaa Xaa Glu Gly
 1               5                   10

<210> SEQ ID NO 243
<211> LENGTH: 36
<212> TYPE: PRT
<213> ORGANISM: Artificial Sequence
<220> FEATURE:
<223> OTHER INFORMATION: Polypeptide
<220> FEATURE:
```

```
-continued

<221> NAME/KEY: VARIANT
<222> LOCATION: (1)...(36)
<223> OTHER INFORMATION: Xaa = any amino acid

<400> SEQUENCE: 243

Gly Gly Xaa Pro Xaa Xaa Xaa Xaa Glu Gly Asn Gln Xaa Xaa Xaa Xaa
 1               5                  10                  15

Ile Leu Met Xaa Xaa Asp Gly Glu Gly Phe Ile Leu Asp Ser Ala Ser
            20                  25                  30

Xaa Ala Ile Val
        35

<210> SEQ ID NO 244
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 244

Cys Xaa Gly Val Xaa Xaa Ala Ile Met Val Xaa Xaa Ala Val
 1               5                  10

<210> SEQ ID NO 245
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 245

Asn Xaa Asp Gly Glu Gly Ser Xaa Ala Gly Pro Val Xaa Xaa Cys Gly
 1               5                  10                  15

Asn Ala Gly Xaa Arg Ala Cys Thr Val Xaa Xaa Xaa Xaa Ala Ile Leu
            20                  25                  30

Val

<210> SEQ ID NO 246
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 246

Glu Arg Gly Xaa Xaa Xaa Thr Xaa Ala Ser Cys Gly Ser Thr Ala Gly
 1               5                  10                  15

Xaa Xaa Ala Gly Ser Ala Cys Ser Thr Val
            20                  25

<210> SEQ ID NO 247
<211> LENGTH: 31
<212> TYPE: PRT
<213> ORGANISM: Artificial Sequence
<220> FEATURE:
```

```
<223> OTHER INFORMATION: Polypeptide
<220> FEATURE:
<221> NAME/KEY: VARIANT
<222> LOCATION: (1)...(31)
<223> OTHER INFORMATION: Xaa = any amino acid

<400> SEQUENCE: 247

Asp Gly Glu Gly Ser Xaa Ala Gly Pro Val Xaa Xaa Cys Gly Asn Ala
1               5                   10                  15

Gly Xaa Arg Ala Cys Thr Val Xaa Xaa Xaa Xaa Ala Ile Leu Val
            20                  25                  30

<210> SEQ ID NO 248
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 248

Arg Gly Xaa Xaa Xaa Thr Xaa Ala Ser Cys Gly Ser Thr Ala Gly Xaa
1               5                   10                  15

Xaa Ala Gly Ser Ala Cys Ser Thr Val
            20                  25

<210> SEQ ID NO 249
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid

<400> SEQUENCE: 249

Gly Glu Gly Ser Xaa Ala Gly Pro Val Xaa Xaa Cys Gly Asn Ala Gly
1               5                   10                  15

Xaa Arg Ala Cys Thr Val Xaa Xaa Xaa Xaa Ala Ile Leu Val
            20                  25                  30

<210> SEQ ID NO 250
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 250

Gly Xaa Xaa Xaa Thr Xaa Ala Ser Cys Gly Ser Thr Ala Gly Xaa Xaa
1               5                   10                  15

Ala Gly Ser Ala Cys Ser Thr Val
            20

<210> SEQ ID NO 251
<211> LENGTH: 19
<212> TYPE: PRT
<213> ORGANISM: Artificial Sequence
<220> FEATURE:
```

-continued

<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 251

Cys Gly Asn Ala Gly Xaa Arg Ala Cys Thr Val Xaa Xaa Xaa Xaa Ala
1               5                   10                  15

Ile Leu Val

<210> SEQ ID NO 252
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 252

Thr Gly Ile Val Asn Ser Thr Ala Asp Xaa Asp Glu Arg Thr
1               5                   10

<210> SEQ ID NO 253
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 253

Arg Xaa Gly Xaa Thr Glu Xaa Ala Gly Ser Thr Xaa Ala Asp Glu Ser
1               5                   10                  15

Thr Ile Leu Xaa Xaa Xaa Xaa Gly Asn
            20                  25

<210> SEQ ID NO 254
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 254

Thr Gly Ile Val Asn Ser Thr Ala Asp Xaa Asp Glu Arg Thr
1               5                   10

<210> SEQ ID NO 255
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 255

```
Lys Xaa Xaa Ile Leu Thr Ala Gly Pro Xaa Thr Ile Met Xaa Xaa Xaa
 1               5                  10                  15

Ser Thr Val

<210> SEQ ID NO 256
<211> LENGTH: 8
<212> TYPE: PRT
<213> ORGANISM: Artificial Sequence
<220> FEATURE:
<223> OTHER INFORMATION: Polypeptide

<400> SEQUENCE: 256

Pro Asp Cys Gly Leu Met Lys Arg
 1               5

<210> SEQ ID NO 257
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 257

Gly Ser Thr Phe Asp Pro Xaa Xaa Xaa Gly His Xaa Xaa Ile Leu Met
 1               5                  10                  15

Val Phe Ile Leu Val Xaa Xaa Ala Gly Ser Thr
            20                  25

<210> SEQ ID NO 258
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 258

Phe Asp Pro Xaa Xaa Xaa Gly His Xaa Xaa Ile Leu Met Val Phe Ile
 1               5                  10                  15

Leu Val Xaa Xaa Ala Gly Ser Thr
            20

<210> SEQ ID NO 259
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 259

Asp Pro Xaa Xaa Xaa Gly His Xaa Xaa Ile Leu Met Val Phe Ile Leu
 1               5                  10                  15

Val Xaa Xaa Ala Gly Ser Thr
            20
```

```
<210> SEQ ID NO 260
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 260

Gly Xaa Xaa Xaa His His Xaa Xaa Glu Ala Gly Ser Thr Xaa Xaa Lys
1               5                   10                  15

Ala Gly Ser Val Xaa Ala Gly Ser Xaa Ala Ser Thr Val Ile Leu Met
            20                  25                  30

Val Xaa Xaa Ala Cys
        35

<210> SEQ ID NO 261
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 261

His His Xaa Xaa Glu Asp Xaa Ala Gly Ile Leu Ala Cys Ser Thr Val
1               5                   10                  15

Ile Leu Gly Xaa Xaa Phe Ile Leu Val
            20                  25

<210> SEQ ID NO 262
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 262

His His Xaa Xaa Glu Ala Gly Ser Thr Xaa Xaa Lys Ala Gly Ser Val
1               5                   10                  15

Xaa Ala Gly Ser Xaa Ala Ser Thr Val Ile Leu Met Val Xaa Xaa Ala
            20                  25                  30

Cys

<210> SEQ ID NO 263
<211> LENGTH: 36
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(36)
<223> OTHER INFORMATION: Xaa = any amino acid

<400> SEQUENCE: 263

Gly Xaa Xaa Xaa His Xaa Xaa Glu Ala Gly Ser Thr Xaa Xaa Lys Ala
1               5                   10                  15
```

```
Gly Ser Val Xaa Ala Gly Ser Xaa Ala Ser Thr Val Ile Leu Met Val
            20                  25                  30

Xaa Xaa Ala Cys
        35

<210> SEQ ID NO 264
<211> LENGTH: 36
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(36)
<223> OTHER INFORMATION: Xaa = any amino acid

<400> SEQUENCE: 264

Gly Xaa Xaa Xaa His Xaa Xaa Glu Ala Gly Ser Thr Xaa Xaa Lys Ala
1               5                   10                  15

Gly Ser Val Xaa Ala Gly Ser Xaa Ala Ser Thr Val Ile Leu Met Val
            20                  25                  30

Xaa Xaa Ala Cys
        35

<210> SEQ ID NO 265
<211> LENGTH: 34
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(34)
<223> OTHER INFORMATION: Xaa = any amino acid

<400> SEQUENCE: 265

Thr Asp Gly Pro Xaa Ala Asp Gly Asn Pro Ser Phe Xaa Asp Glu Asn
1               5                   10                  15

Thr His Leu Met Ile Leu Met Xaa Xaa Phe Ile Leu Met Val Xaa Xaa
            20                  25                  30

His Tyr

<210> SEQ ID NO 266
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 266

His Xaa Xaa Glu Asp Xaa Ala Gly Ile Leu Ala Cys Ser Thr Val Ile
1               5                   10                  15

Leu Gly Xaa Xaa Phe Ile Leu Val
            20

<210> SEQ ID NO 267
<211> LENGTH: 21
<212> TYPE: PRT
<213> ORGANISM: Artificial Sequence
<220> FEATURE:
<223> OTHER INFORMATION: Polypeptide
<220> FEATURE:
```

```
<221> NAME/KEY: VARIANT
<222> LOCATION: (1)...(21)
<223> OTHER INFORMATION: Xaa = any amino acid

<400> SEQUENCE: 267

Glu Asp Xaa Ala Gly Ile Leu Ala Cys Ser Thr Val Ile Leu Gly Xaa
 1               5                  10                  15

Xaa Phe Ile Leu Val
             20

<210> SEQ ID NO 268
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 268

Gly Gly Tyr Xaa Arg Ile Leu Met Val Xaa Lys Arg Xaa Xaa Xaa Arg
 1               5                  10                  15

Xaa Xaa Asp Gly Xaa Ala Gly Ser Thr Val Xaa Xaa Xaa Xaa Ile Leu
             20                  25                  30

Val

<210> SEQ ID NO 269
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid

<400> SEQUENCE: 269

Gly Tyr Xaa Arg Ile Leu Met Val Xaa Lys Arg Xaa Xaa Xaa Arg Xaa
 1               5                  10                  15

Xaa Asp Gly Xaa Ala Gly Ser Thr Val Xaa Xaa Xaa Xaa Ile Leu Val
             20                  25                  30

<210> SEQ ID NO 270
<211> LENGTH: 31
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(31)
<223> OTHER INFORMATION: Xaa = any amino acid

<400> SEQUENCE: 270

Gly Tyr Arg Ile Leu Met Val Xaa Lys Arg Xaa Xaa Xaa Arg Xaa Xaa
 1               5                  10                  15

Asp Gly Xaa Ala Gly Ser Thr Val Xaa Xaa Xaa Xaa Ile Leu Val
             20                  25                  30

<210> SEQ ID NO 271
<211> LENGTH: 48
<212> TYPE: PRT
<213> ORGANISM: Artificial Sequence
<220> FEATURE:
```

-continued

```
<223> OTHER INFORMATION: Polypeptide
<220> FEATURE:
<221> NAME/KEY: VARIANT
<222> LOCATION: (1)...(48)
<223> OTHER INFORMATION: Xaa = any amino acid

<400> SEQUENCE: 271

Tyr Xaa Asn Cys Ser Thr Xaa Xaa Xaa Lys Ala Ser Thr Xaa Ala
1               5                   10                  15

Cys Ser Thr Val Ala Asp Gly Xaa Xaa Cys Asp Gly Val Gly Thr Xaa
            20                  25                  30

Ala Gly Ser Thr Val Xaa Ala Gly Thr Val Xaa Xaa Xaa Ala Ile Val
        35                  40                  45

<210> SEQ ID NO 272
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 272

Gly Val Xaa Phe Met Ala Cys Gly Glu Xaa Ala Ser Val Xaa Xaa Ile
1               5                   10                  15

Leu Val Ala Cys Asn Ser Thr
            20

<210> SEQ ID NO 273
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 273

Val Xaa Phe Met Ala Cys Gly Glu Xaa Ala Ser Val Xaa Xaa Ile Leu
1               5                   10                  15

Val Ala Cys Asn Ser Thr
            20

<210> SEQ ID NO 274
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 274

Ser Gly Xaa Ala Xaa Gly Ala Ile Val Asp Xaa Xaa Ala Cys Ser Xaa
1               5                   10                  15

Xaa Xaa Ala Cys Ser Thr Val Ile Leu Met Val
            20                  25

<210> SEQ ID NO 275
<211> LENGTH: 26
```

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 275

Gly Xaa Ala Xaa Gly Ala Ile Val Asp Xaa Xaa Ala Cys Ser Xaa Xaa
 1               5                  10                  15

Xaa Ala Cys Ser Thr Val Ile Leu Met Val
            20                  25

<210> SEQ ID NO 276
<211> LENGTH: 58
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(58)
<223> OTHER INFORMATION: Xaa = any amino acid

<400> SEQUENCE: 276

Glu Met Xaa Thr Gly Glu Gly Lys Thr Ile Leu Xaa Xaa Xaa Xaa Ala
 1               5                  10                  15

Pro Val Xaa Xaa Xaa Xaa Ala Gly Ser Val Phe Ile Leu Met Xaa Xaa
            20                  25                  30

Xaa Xaa Cys Thr Val Xaa Ile Leu Met Val Xaa Thr Xaa Asn Asp Glu
        35                  40                  45

Tyr Leu Ala Ser Val Xaa Xaa Asp Gly Gln
    50                  55

<210> SEQ ID NO 277
<211> LENGTH: 57
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(57)
<223> OTHER INFORMATION: Xaa = any amino acid

<400> SEQUENCE: 277

Met Xaa Thr Gly Glu Gly Lys Thr Ile Leu Xaa Xaa Xaa Xaa Ala Pro
 1               5                  10                  15

Val Xaa Xaa Xaa Xaa Ala Gly Ser Val Phe Ile Leu Met Xaa Xaa Xaa
            20                  25                  30

Xaa Cys Thr Val Xaa Ile Leu Met Val Xaa Thr Xaa Asn Asp Glu Tyr
        35                  40                  45

Leu Ala Ser Val Xaa Xaa Asp Gly Gln
    50                  55

<210> SEQ ID NO 278
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid
```

<400> SEQUENCE: 278

Arg Asp Xaa Gln Ile Leu Xaa Gly Arg Ala Cys Ser Thr Ala Gly Arg
1               5                   10                  15

Xaa Gly Asp Xaa Gly Xaa Ala Ser Thr Xaa Phe Ile Xaa Xaa Ser Xaa
            20                  25                  30

Asp Glu Gly Gln Asp Xaa Leu Val Phe Ile Leu Met Val
        35                  40                  45

<210> SEQ ID NO 279
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid

<400> SEQUENCE: 279

Arg Ile Leu Val Asp Leu Xaa Gly Arg Ala Cys Ser Thr Ala Gly Arg
1               5                   10                  15

Xaa Gly Asp Xaa Gly Xaa Ala Ser Thr Xaa Phe Ile Xaa Xaa Ser Xaa
            20                  25                  30

Asp Glu Gly Gln Asp Xaa Leu Val Phe Ile Leu Met Val
        35                  40                  45

<210> SEQ ID NO 280
<211> LENGTH: 42
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(42)
<223> OTHER INFORMATION: Xaa = any amino acid

<400> SEQUENCE: 280

Gln Ile Leu Xaa Gly Arg Ala Cys Ser Thr Ala Gly Arg Xaa Gly Asp
1               5                   10                  15

Xaa Gly Xaa Ala Ser Thr Xaa Phe Ile Xaa Xaa Ser Xaa Asp Glu Gly
            20                  25                  30

Gln Asp Xaa Leu Val Phe Ile Leu Met Val
        35                  40

<210> SEQ ID NO 281
<211> LENGTH: 41
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(41)
<223> OTHER INFORMATION: Xaa = any amino acid

<400> SEQUENCE: 281

Asp Leu Xaa Gly Arg Ala Cys Ser Thr Ala Gly Arg Xaa Gly Asp Xaa
1               5                   10                  15

Gly Xaa Ala Ser Thr Xaa Phe Ile Xaa Xaa Ser Xaa Asp Glu Gly Gln
            20                  25                  30

Asp Xaa Leu Val Phe Ile Leu Met Val
        35                  40

<210> SEQ ID NO 282
<211> LENGTH: 43
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(43)
<223> OTHER INFORMATION: Xaa = any amino acid

<400> SEQUENCE: 282

Arg Xaa Xaa Leu Xaa Gly Arg Ala Cys Ser Thr Ala Gly Arg Xaa Gly
 1               5                  10                  15

Asp Xaa Gly Xaa Ala Ser Thr Xaa Phe Ile Xaa Xaa Ser Xaa Asp Glu
            20                  25                  30

Gly Gln Asp Xaa Leu Val Phe Ile Leu Met Val
        35                  40

<210> SEQ ID NO 283
<211> LENGTH: 40
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(40)
<223> OTHER INFORMATION: Xaa = any amino acid

<400> SEQUENCE: 283

Leu Xaa Gly Arg Ala Cys Ser Thr Ala Gly Arg Xaa Gly Asp Xaa Gly
 1               5                  10                  15

Xaa Ala Ser Thr Xaa Phe Ile Xaa Xaa Ser Xaa Asp Glu Gly Gln Asp
            20                  25                  30

Xaa Leu Val Phe Ile Leu Met Val
        35                  40

<210> SEQ ID NO 284
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 284

Thr Asn Gln Ser Met Ala Gly Arg Gly Thr Val Asp Ile Xaa Ile Leu
 1               5                  10                  15

Pro Asp Gly Ser Thr Xaa Asp Glu Gly Asn Ser
            20                  25

<210> SEQ ID NO 285
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 285

```
Met Ala Gly Arg Gly Thr Val Asp Ile Xaa Ile Leu Pro Asp Gly Ser
 1               5                  10                  15

Thr Xaa Asp Glu Gly Asn Ser
            20
```

<210> SEQ ID NO 286
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 286

```
Gly Asp Glu Ser Ser His Gly Xaa Xaa Ile Leu Met Val Gly Thr Val
 1               5                  10                  15

Xaa Ile Leu Val Ile Leu Val Asp Glu Asn Ser Thr Gly
            20                  25
```

<210> SEQ ID NO 287
<211> LENGTH: 38
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(38)
<223> OTHER INFORMATION: Xaa = any amino acid

<400> SEQUENCE: 287

```
Gly His Ala Glu Xaa Asp Xaa Xaa Ile Leu Xaa Asp Xaa Ala Ser Val
 1               5                  10                  15

Ala Ser Val Cys Asp Xaa Arg Ser Xaa Xaa Thr Pro Ser Thr Xaa Ala
            20                  25                  30

Xaa Xaa Xaa Ala Leu Val
        35
```

<210> SEQ ID NO 288
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 288

```
His Ala Glu Xaa Asp Xaa Xaa Ile Leu Xaa Asp Xaa Ala Ser Val Ala
 1               5                  10                  15

Ser Val Cys Asp Xaa Arg Ser Xaa Xaa Thr Pro Ser Thr Xaa Ala Xaa
            20                  25                  30

Xaa Xaa Ala Leu Val
        35
```

<210> SEQ ID NO 289
<211> LENGTH: 22
<212> TYPE: PRT
<213> ORGANISM: Artificial Sequence
<220> FEATURE:
<223> OTHER INFORMATION: Polypeptide

```
<220> FEATURE:
<221> NAME/KEY: VARIANT
<222> LOCATION: (1)...(22)
<223> OTHER INFORMATION: Xaa = any amino acid

<400> SEQUENCE: 289

Asp Ile Leu Val Xaa Asp Glu Gly Gln Ser Thr Ser Thr Gly Xaa Thr
1               5                   10                  15

Leu Xaa Xaa Xaa Xaa Leu
            20

<210> SEQ ID NO 290
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 290

Leu Xaa Gln Ala Ile Leu Val Ala Gly Pro Ser Thr Gly Arg Xaa Gly
1               5                   10                  15

Val Arg

<210> SEQ ID NO 291
<211> LENGTH: 67
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(67)
<223> OTHER INFORMATION: Xaa = any amino acid

<400> SEQUENCE: 291

His Ile Leu Gly Ile Leu Val Thr Glu Ala Ser Gly Xaa Xaa Xaa Xaa
1               5                   10                  15

Ala Gly Ser Xaa Ile Val Xaa Ser Ala Ser Thr Xaa Ala Gly Ser Phe
            20                  25                  30

Ile Leu Ala Gly Ser Xaa Ile Leu Met Leu Met Xaa Xaa Gly Asn Ile
        35                  40                  45

Leu Gly Ala Asp Asn Thr Ile Leu Met Val Arg Xaa Ser Ile Leu Met
    50                  55                  60

Ala Ser Thr
65

<210> SEQ ID NO 292
<211> LENGTH: 65
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(65)
<223> OTHER INFORMATION: Xaa = any amino acid

<400> SEQUENCE: 292

Leu Gly Ile Leu Val Thr Glu Ala Ser Gly Xaa Xaa Xaa Xaa Ala Gly
1               5                   10                  15

Ser Xaa Ile Val Xaa Ser Ala Ser Thr Xaa Ala Gly Ser Phe Ile Leu
            20                  25                  30
```

```
Ala Gly Ser Xaa Ile Leu Met Leu Met Xaa Xaa Gly Asn Ile Leu Gly
        35                  40                  45

Ala Asp Asn Thr Ile Leu Met Val Arg Xaa Ser Ile Leu Met Ala Ser
        50                  55                  60

Thr
65

<210> SEQ ID NO 293
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 293

Gly Cys Val Asn Ala Gly Ile Leu Pro Gly Glu Xaa Xaa Xaa Ala Ser
1               5                   10                  15

Thr Xaa Xaa Ala Gly Xaa Ala Ser Thr Val
        20                  25

<210> SEQ ID NO 294
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 294

Cys Val Asn Ala Gly Ile Leu Pro Gly Glu Xaa Xaa Xaa Ala Ser Thr
1               5                   10                  15

Xaa Xaa Ala Gly Xaa Ala Ser Thr Val
        20                  25

<210> SEQ ID NO 295
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(12)
<223> OTHER INFORMATION: Xaa = any amino acid

<400> SEQUENCE: 295

Arg Ile Val Gly Ala Val Asn Xaa Gly Ser Ile Leu
1               5                   10

<210> SEQ ID NO 296
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 296
```

```
Leu Xaa Xaa Xaa Gly Ala Asp Asn Thr Ile Leu Met Val Arg Xaa Ser
1               5                   10                  15

Ile Leu Met Ala Ser Thr
            20
```

<210> SEQ ID NO 297
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 297

```
Leu Xaa Xaa Xaa Gly Xaa Thr Ile Leu Met Val Arg Xaa Ser Ile Leu
1               5                   10                  15

Met Ala Ser Thr
            20
```

<210> SEQ ID NO 298
<211> LENGTH: 10
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(10)
<223> OTHER INFORMATION: Xaa = any amino acid

<400> SEQUENCE: 298

```
Ile Gly Ala Val Asn Xaa Gly Ser Ile Leu
1               5                   10
```

<210> SEQ ID NO 299
<211> LENGTH: 31
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(31)
<223> OTHER INFORMATION: Xaa = any amino acid

<400> SEQUENCE: 299

```
Gly Xaa Ser Thr Gly Ala Cys Ser Gly Lys Ser Thr Ser Xaa Ile
1               5                   10                  15

Leu Lys Arg Xaa Phe Ile Leu Met Val Asp Asn Xaa Ile Leu Met
            20                  25                  30
```

<210> SEQ ID NO 300
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 300

```
Arg Xaa Xaa Xaa Gly Ser Met Leu Val Phe Gln Xaa Xaa Xaa Leu Pro
1               5                   10                  15
```

Val Phe Trp

<210> SEQ ID NO 301
<211> LENGTH: 41
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(41)
<223> OTHER INFORMATION: Xaa = any amino acid

<400> SEQUENCE: 301

Glu Xaa Xaa Lys Xaa Xaa Asn Xaa Ile Val Xaa Ala Asn Ser Thr Val
 1               5                  10                  15

Xaa Xaa Xaa Cys Gly Xaa Xaa Xaa Xaa Ile Pro Val Xaa Xaa Xaa Xaa
                20                  25                  30

Ala Glu Gly Asn Xaa Xaa Ile Leu Val
            35                  40

<210> SEQ ID NO 302
<211> LENGTH: 38
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(38)
<223> OTHER INFORMATION: Xaa = any amino acid

<400> SEQUENCE: 302

Gly Xaa Xaa Ala Gly Xaa Ser Asp Ala Gly Asp Ala Ile Val Ala Ile
 1               5                  10                  15

Leu Val Xaa His Ala Ser Thr Ile Leu Val Xaa Asp Asn Ala Ser Xaa
                20                  25                  30

Xaa Gly Ser Ala Gly Val
        35

<210> SEQ ID NO 303
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid

<400> SEQUENCE: 303

Ser Asp Ala Gly Asp Ala Ile Val Ala Ile Leu Val Xaa His Ala Ser
 1               5                  10                  15

Thr Ile Leu Val Xaa Asp Asn Ala Ser Xaa Xaa Gly Ser Ala Gly Val
                20                  25                  30

<210> SEQ ID NO 304
<211> LENGTH: 38
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(38)
<223> OTHER INFORMATION: Xaa = any amino acid -continued

<400> SEQUENCE: 304

Gly Xaa Xaa Xaa Xaa Asp Ala Gly Thr Asp Ala Ile Pro Val Ala Ile
1               5                   10                  15

Leu Val Xaa His Ala Ser Thr Ile Leu Val Xaa Asp Asn Ala Ser Xaa
            20                  25                  30

Xaa Gly Ser Ala Gly Val
        35

<210> SEQ ID NO 305
<211> LENGTH: 31
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(31)
<223> OTHER INFORMATION: Xaa = any amino acid

<400> SEQUENCE: 305

Asp Ala Gly Asp Ala Ile Val Ala Ile Leu Val Xaa His Ala Ser Thr
1               5                   10                  15

Ile Leu Val Xaa Asp Asn Ala Ser Xaa Xaa Gly Ser Ala Gly Val
            20                  25                  30

<210> SEQ ID NO 306
<211> LENGTH: 35
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(35)
<223> OTHER INFORMATION: Xaa = any amino acid

<400> SEQUENCE: 306

Gly Xaa Gly Xaa Asp Xaa His Xaa Phe Ile Leu Xaa Xaa Asp Glu Gly
1               5                   10                  15

Asn Ser Xaa Xaa Xaa Xaa Ile Leu Pro Ala Cys Gly Val Gly Ile Val
            20                  25                  30

Ile Leu Val
        35

<210> SEQ ID NO 307
<211> LENGTH: 34
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(34)
<223> OTHER INFORMATION: Xaa = any amino acid

<400> SEQUENCE: 307

Gly Xaa Gly Asp Xaa His Xaa Phe Ile Leu Xaa Xaa Asp Glu Gly Asn
1               5                   10                  15

Ser Xaa Xaa Xaa Xaa Ile Leu Pro Ala Cys Gly Val Gly Ile Val Ile
            20                  25                  30

Leu Val

<210> SEQ ID NO 308
<211> LENGTH: 33

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 308

Gly Xaa Asp Xaa His Xaa Phe Ile Leu Xaa Xaa Asp Glu Gly Asn Ser
 1               5                  10                  15

Xaa Xaa Xaa Xaa Ile Leu Pro Ala Cys Gly Val Gly Ile Val Ile Leu
            20                  25                  30

Val

<210> SEQ ID NO 309
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 309

Glu Ala Ser Thr Val His Pro Xaa Xaa Ala Xaa Cys Ser Asp Ala Gly
 1               5                  10                  15

Asn Ser

<210> SEQ ID NO 310
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 310

Glu Xaa His Xaa Xaa Pro Xaa Xaa Ala Xaa Cys Ser Asp Ala Gly Asn
 1               5                  10                  15

Ser

<210> SEQ ID NO 311
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 311

Glu His Xaa Xaa Pro Xaa Xaa Ala Xaa Cys Ser Asp Ala Gly Asn Ser
 1               5                  10                  15

<210> SEQ ID NO 312
<211> LENGTH: 46
<212> TYPE: PRT
<213> ORGANISM: Artificial Sequence
<220> FEATURE:
```

<223> OTHER INFORMATION: Polypeptide
<220> FEATURE:
<221> NAME/KEY: VARIANT
<222> LOCATION: (1)...(46)
<223> OTHER INFORMATION: Xaa = any amino acid

<400> SEQUENCE: 312

Ile Xaa Xaa Leu Val Xaa Xaa His Xaa Xaa Xaa Xaa Lys Asp Xaa Xaa
 1               5                  10                  15

Gly Ser Thr Xaa Xaa Ala Gly Phe Leu Xaa Xaa Xaa Xaa Ala Gly Asn
             20                  25                  30

Ser Xaa Arg Lys Arg Xaa Leu Met Ile Leu Xaa Phe His Tyr
         35                  40                  45

<210> SEQ ID NO 313
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)
<223> OTHER INFORMATION: Xaa = any amino acid

<400> SEQUENCE: 313

His Xaa Xaa Xaa Xaa Lys Asp Xaa Xaa Gly Ser Thr Xaa Xaa Ala Gly
 1               5                  10                  15

Phe Leu Xaa Xaa Xaa Xaa Ala Gly Asn Ser Xaa Arg Lys Arg Xaa Leu
             20                  25                  30

Met Ile Leu Xaa Phe His Tyr
             35

<210> SEQ ID NO 314
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 314

Gly Xaa Xaa Ala Asp Glu Gly Gln Ser Ala Leu Val Gln Xaa Xaa Leu
 1               5                  10                  15

Xaa Xaa Xaa Ile Xaa Xaa Leu Val Xaa Xaa His
             20                  25

<210> SEQ ID NO 315
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 315

Gly Xaa Ser Thr Glu Xaa Ala Ile Leu Pro Ile Val Ser Ser Xaa Ala
 1               5                  10                  15

Gly Thr Xaa Xaa Xaa Ala Ile Leu Val
             20                  25

```
<210> SEQ ID NO 316
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 316

Gly Xaa Glu Xaa Ala Ile Leu Pro Ile Val Ser Ser Xaa Ala Gly Thr
 1               5                  10                  15

Xaa Xaa Xaa Ala Ile Leu Val
            20

<210> SEQ ID NO 317
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 317

Gly Glu Xaa Ala Ile Leu Pro Ile Val Ser Ser Xaa Ala Gly Thr Xaa
 1               5                  10                  15

Xaa Xaa Ala Ile Leu Val
            20

<210> SEQ ID NO 318
<211> LENGTH: 41
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(41)
<223> OTHER INFORMATION: Xaa = any amino acid

<400> SEQUENCE: 318

His Pro Xaa Phe Trp Tyr Ser Thr Gly Xaa Xaa Lys Arg Xaa Xaa Xaa
 1               5                  10                  15

Xaa Ala Asp Glu Gly Ser Thr Gly Ser Xaa Ala Ile Val Ala Asp Glu
            20                  25                  30

Ser Xaa Phe Xaa Xaa Lys Arg Phe Tyr
        35                  40

<210> SEQ ID NO 319
<211> LENGTH: 43
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(43)
<223> OTHER INFORMATION: Xaa = any amino acid

<400> SEQUENCE: 319

His Pro Xaa Phe Trp Tyr Ala Glu Ser Thr Gly Xaa Xaa Lys Arg Xaa
 1               5                  10                  15
```

```
Xaa Xaa Xaa Ala Asp Glu Gly Ser Thr Gly Ser Xaa Ala Ile Val Ala
            20                  25                  30

Asp Glu Ser Xaa Phe Xaa Xaa Lys Arg Phe Tyr
            35                  40

<210> SEQ ID NO 320
<211> LENGTH: 40
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(40)
<223> OTHER INFORMATION: Xaa = any amino acid

<400> SEQUENCE: 320

Pro Xaa Phe Trp Tyr Ser Thr Gly Xaa Xaa Lys Arg Xaa Xaa Xaa Xaa
1               5                   10                  15

Ala Asp Glu Gly Ser Thr Gly Ser Xaa Ala Ile Val Ala Asp Glu Ser
            20                  25                  30

Xaa Phe Xaa Xaa Lys Arg Phe Tyr
            35                  40

<210> SEQ ID NO 321
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 321

His Gly Xaa Xaa Gly Xaa Xaa Glu Asp Thr Gly Xaa Ile Leu Met Val
1               5                   10                  15

Xaa Ala Gly Ser
            20

<210> SEQ ID NO 322
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(33)
<223> OTHER INFORMATION: Xaa = any amino acid

<400> SEQUENCE: 322

Val Xaa Xaa Xaa Ala Ser Val Xaa Lys Xaa Xaa Ala Ile Leu Val Xaa
1               5                   10                  15

Xaa Ala Ile Met Val Xaa Xaa Ala Ile Leu Val Phe Xaa Val Xaa Xaa
            20                  25                  30

Val

<210> SEQ ID NO 323
<211> LENGTH: 33
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
```

```
<222> LOCATION: (1)...(33)
<223> OTHER INFORMATION: Xaa = any amino acid

<400> SEQUENCE: 323

Val Xaa Xaa Xaa Ala Ser Val Xaa Lys Xaa Xaa Ala Ile Leu Val Xaa
 1               5                  10                  15

Xaa Ala Ile Met Val Xaa Xaa Ala Ile Leu Val Phe Xaa Xaa Val Xaa
            20                  25                  30

Val

<210> SEQ ID NO 324
<211> LENGTH: 34
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(34)
<223> OTHER INFORMATION: Xaa = any amino acid

<400> SEQUENCE: 324

Val Xaa Xaa Xaa Ala Ser Val Xaa Lys Xaa Xaa Ala Ile Leu Val Xaa
 1               5                  10                  15

Xaa Ala Ile Met Val Xaa Xaa Ala Ile Leu Val Phe Xaa Xaa Val Xaa
            20                  25                  30

Xaa Val

<210> SEQ ID NO 325
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 325

Lys Xaa Xaa Ala Ile Leu Val Xaa Xaa Ala Ile Met Val Xaa Xaa Ala
 1               5                  10                  15

Ile Leu Val Phe Xaa Val Xaa Xaa Val
            20                  25

<210> SEQ ID NO 326
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 326

Lys Xaa Xaa Ala Ile Leu Val Xaa Xaa Ala Ile Met Val Xaa Xaa Ala
 1               5                  10                  15

Ile Leu Val Phe Xaa Xaa Val Xaa Val
            20                  25

<210> SEQ ID NO 327
<211> LENGTH: 26
<212> TYPE: PRT
<213> ORGANISM: Artificial Sequence
```

```
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 327

Lys Xaa Xaa Ala Ile Leu Val Xaa Xaa Ala Ile Met Val Xaa Xaa Ala
 1               5                  10                  15

Ile Leu Val Phe Xaa Xaa Val Xaa Xaa Val
             20                  25

<210> SEQ ID NO 328
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 328

Asp Xaa Ala Ile Val Phe Ile Leu Val Ala Ser Gly Ile Val Asn Xaa
 1               5                  10                  15

Gly Xaa Asn

<210> SEQ ID NO 329
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 329

Asp Xaa Ala Ile Val Phe Ile Leu Val Ala Ser Gly Ile Val Asn Xaa
 1               5                  10                  15

Xaa Gly Asn

<210> SEQ ID NO 330
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: v

<400> SEQUENCE: 330

Asp Xaa Ala Ile Val Phe Ile Leu Val Ala Ser Gly Ile Val Asn Xaa
 1               5                  10                  15

Xaa Gly Xaa Asn
             20

<210> SEQ ID NO 331
<211> LENGTH: 22
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(22)
<223> OTHER INFORMATION: Xaa = any amino acid

<400> SEQUENCE: 331

Asp Phe Ile Leu Met Val Xaa Phe Ile Leu Val Ser Gly Xaa Asn Xaa
1               5                   10                  15

Ala Gly Thr Xaa Asn Thr
            20

<210> SEQ ID NO 332
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 332

Gly Xaa Gly Asn Tyr Xaa Xaa Xaa Glu Xaa Xaa Phe His Trp Xaa Xaa
1               5                   10                  15

Xaa Phe Ile Leu Val Xaa Gly Pro
            20

<210> SEQ ID NO 333
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 333

Gly Xaa Gly Asn Xaa Tyr Xaa Xaa Glu Xaa Xaa Phe His Trp Xaa Xaa
1               5                   10                  15

Xaa Phe Ile Leu Val Xaa Gly Pro
            20

<210> SEQ ID NO 334
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 334

Gly Xaa Gly Asn Xaa Tyr Xaa Xaa Xaa Glu Xaa Xaa Phe His Trp Xaa
1               5                   10                  15

Xaa Xaa Phe Ile Leu Val Xaa Gly Pro
            20                  25

<210> SEQ ID NO 335
<211> LENGTH: 22
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(22)
<223> OTHER INFORMATION: Xaa = any amino acid

<400> SEQUENCE: 335

Gly Asn Tyr Xaa Xaa Xaa Glu Xaa Xaa Phe His Trp Xaa Xaa Xaa Phe
 1               5                  10                  15

Ile Leu Val Xaa Gly Pro
            20

<210> SEQ ID NO 336
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 336

Gly Asn Xaa Tyr Xaa Xaa Glu Xaa Xaa Phe His Trp Xaa Xaa Xaa Phe
 1               5                  10                  15

Ile Leu Val Xaa Gly Pro
            20

<210> SEQ ID NO 337
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 337

Gly Asn Xaa Tyr Xaa Xaa Xaa Glu Xaa Xaa Phe His Trp Xaa Xaa Xaa
 1               5                  10                  15

Phe Ile Leu Val Xaa Gly Pro
            20

<210> SEQ ID NO 338
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 338

Arg Xaa Leu Xaa Asn Xaa Gly His Ser Thr Phe Ile Leu Val Ala Gly
 1               5                  10                  15

Xaa Ala Gly Leu Val Ile Leu Val Glu
            20                  25

<210> SEQ ID NO 339
<211> LENGTH: 25
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(25)
<223> OTHER INFORMATION: Xaa = any amino acid

<400> SEQUENCE: 339

Arg Xaa Xaa Leu Asn Xaa Gly His Ser Thr Phe Ile Leu Val Ala Gly
 1               5                  10                  15

Xaa Ala Gly Leu Val Ile Leu Val Glu
            20                  25

<210> SEQ ID NO 340
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 340

Arg Xaa Xaa Leu Xaa Asn Xaa Gly His Ser Thr Phe Ile Leu Val Ala
 1               5                  10                  15

Gly Xaa Ala Gly Leu Val Ile Leu Val Glu
            20                  25

<210> SEQ ID NO 341
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 341

Gly Gly Gly Ala Thr Val Xaa Xaa Asp Xaa Ala Gly Thr Val Gly Xaa
 1               5                  10                  15

Ala Xaa Xaa Xaa Xaa Xaa Arg Gly
            20

<210> SEQ ID NO 342
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 342

Gly Gly Gly Ala Thr Val Xaa Xaa Asp Xaa Ala Gly Thr Val Gly Xaa
 1               5                  10                  15

Xaa Ala Xaa Xaa Xaa Xaa Arg Gly
            20

<210> SEQ ID NO 343
<211> LENGTH: 25
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(25)
<223> OTHER INFORMATION: Xaa = any amino acid

<400> SEQUENCE: 343

Gly Gly Gly Ala Thr Val Xaa Xaa Asp Xaa Ala Gly Thr Val Gly Xaa
  1               5                  10                  15

Xaa Ala Xaa Xaa Xaa Xaa Xaa Arg Gly
             20                  25

<210> SEQ ID NO 344
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 344

Leu Xaa Asn Xaa Gly His Ser Thr Phe Ile Leu Val Ala Gly Xaa Ala
  1               5                  10                  15

Gly Leu Val Ile Leu Val Glu
             20

<210> SEQ ID NO 345
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 345

Arg Xaa Xaa Leu Xaa Xaa Xaa Gly His Ser Thr Phe Ile Leu Val Ala
  1               5                  10                  15

Gly Xaa Ala Gly Leu Val Ile Leu Val Glu
             20                  25

<210> SEQ ID NO 346
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 346

Arg Xaa Xaa Xaa Leu Xaa Xaa Gly His Ser Thr Phe Ile Leu Val Ala
  1               5                  10                  15

Gly Xaa Ala Gly Leu Val Ile Leu Val Glu
             20                  25

<210> SEQ ID NO 347
<211> LENGTH: 27
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(27)
<223> OTHER INFORMATION: Xaa = any amino acid

<400> SEQUENCE: 347

Arg Xaa Xaa Xaa Leu Xaa Xaa Xaa Gly His Ser Thr Phe Ile Leu Val
 1               5                  10                  15

Ala Gly Xaa Ala Gly Leu Val Ile Leu Val Glu
            20                  25

<210> SEQ ID NO 348
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 348

Gly Gly Ala Thr Val Xaa Xaa Asp Xaa Ala Gly Thr Val Gly Xaa Ala
 1               5                  10                  15

Xaa Xaa Xaa Xaa Xaa Arg Gly
            20

<210> SEQ ID NO 349
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 349

Gly Gly Ala Thr Val Xaa Xaa Asp Xaa Ala Gly Thr Val Gly Xaa Xaa
 1               5                  10                  15

Ala Xaa Xaa Xaa Xaa Arg Gly
            20

<210> SEQ ID NO 350
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 350

Gly Gly Ala Thr Val Xaa Xaa Asp Xaa Ala Gly Thr Val Gly Xaa Xaa
 1               5                  10                  15

Ala Xaa Xaa Xaa Xaa Xaa Arg Gly
            20

<210> SEQ ID NO 351
<211> LENGTH: 22
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(22)
<223> OTHER INFORMATION: Xaa = any amino acid

<400> SEQUENCE: 351

Gly Ala Thr Val Xaa Xaa Asp Xaa Ala Gly Thr Val Gly Xaa Ala Xaa
  1               5                  10                  15

Xaa Xaa Xaa Xaa Arg Gly
             20

<210> SEQ ID NO 352
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 352

Ala Thr Val Xaa Xaa Asp Xaa Ala Gly Thr Val Gly Xaa Xaa Ala Xaa
  1               5                  10                  15

Xaa Xaa Xaa Arg Gly
             20

<210> SEQ ID NO 353
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 353

Gly Ala Thr Val Xaa Xaa Asp Xaa Ala Gly Thr Val Gly Xaa Xaa Ala
  1               5                  10                  15

Xaa Xaa Xaa Xaa Xaa Arg Gly
             20

<210> SEQ ID NO 354
<211> LENGTH: 61
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(61)
<223> OTHER INFORMATION: Xaa = any amino acid

<400> SEQUENCE: 354

Ser Arg Xaa Xaa Xaa Xaa Xaa Trp Xaa Lys Gly Ala Asp Glu Ser Xaa
  1               5                  10                  15

Ser Gly Xaa Xaa Xaa Xaa Ile Leu Val Xaa Xaa Phe Ile Leu Met Val
             20                  25                  30

Xaa Xaa Asp Cys Asp Xaa Asp Ala Thr Val Ile Leu Met Val Xaa Xaa
         35                  40                  45

Xaa Ala Ile Val Xaa Xaa Xaa Gly Xaa Xaa Ala Cys Gly
         50                  55                  60
```

```
<210> SEQ ID NO 355
<211> LENGTH: 59
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(59)
<223> OTHER INFORMATION: Xaa = any amino acid

<400> SEQUENCE: 355

Ser Xaa Xaa Arg Xaa Xaa Xaa Trp Xaa Lys Gly Ala Asp Glu Ser Xaa
 1               5                  10                  15

Ser Gly Xaa Xaa Xaa Xaa Ile Leu Val Xaa Xaa Phe Ile Leu Met Val
            20                  25                  30

Xaa Xaa Asp Cys Asp Xaa Asp Ala Thr Val Ile Leu Met Val Xaa Xaa
        35                  40                  45

Ala Ile Val Xaa Xaa Gly Xaa Xaa Ala Cys Gly
    50                  55

<210> SEQ ID NO 356
<211> LENGTH: 59
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(59)
<223> OTHER INFORMATION: Xaa = any amino acid

<400> SEQUENCE: 356

Ser Xaa Xaa Xaa Xaa Arg Xaa Trp Xaa Lys Gly Ala Asp Glu Ser Xaa
 1               5                  10                  15

Ser Gly Xaa Xaa Xaa Xaa Ile Leu Val Xaa Xaa Phe Ile Leu Met Val
            20                  25                  30

Xaa Xaa Asp Cys Asp Xaa Asp Ala Thr Val Ile Leu Met Val Xaa Xaa
        35                  40                  45

Ala Ile Val Xaa Xaa Gly Xaa Xaa Ala Cys Gly
    50                  55

<210> SEQ ID NO 357
<211> LENGTH: 61
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(61)
<223> OTHER INFORMATION: Xaa = any amino acid

<400> SEQUENCE: 357

Ser Xaa Xaa Xaa Xaa Arg Xaa Xaa Trp Xaa Lys Gly Ala Asp Glu
 1               5                  10                  15

Ser Xaa Ser Gly Xaa Xaa Xaa Xaa Ile Leu Val Xaa Xaa Phe Ile Leu
                20                  25                  30

Met Val Xaa Xaa Asp Cys Asp Xaa Asp Ala Thr Val Ile Leu Met Val
            35                  40                  45

Xaa Xaa Ala Ile Val Xaa Xaa Gly Xaa Xaa Ala Cys Gly
        50                  55                  60

<210> SEQ ID NO 358
<211> LENGTH: 60
```

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(60)
<223> OTHER INFORMATION: Xaa = any amino acid

<400> SEQUENCE: 358

Arg Xaa Xaa Xaa Xaa Xaa Trp Xaa Lys Gly Ala Asp Glu Ser Xaa Ser
 1               5                  10                  15

Gly Xaa Xaa Xaa Xaa Ile Leu Val Xaa Xaa Phe Ile Leu Met Val Xaa
             20                  25                  30

Xaa Asp Cys Asp Xaa Asp Ala Thr Val Ile Leu Met Val Xaa Xaa Xaa
         35                  40                  45

Ala Ile Val Xaa Xaa Xaa Gly Xaa Xaa Ala Cys Gly
     50                  55                  60

<210> SEQ ID NO 359
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 359

Gly Xaa Xaa Xaa Xaa Cys His Xaa Gly Xaa Xaa Ala Ser Thr Cys Phe
 1               5                  10                  15

Trp

<210> SEQ ID NO 360
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)
<223> OTHER INFORMATION: Xaa = any amino acid

<400> SEQUENCE: 360

Ile Xaa Xaa Xaa Xaa Xaa Asp Xaa Val Xaa Ile Leu Val Ala Glu Phe
 1               5                  10                  15

Ile Leu Met Ser Thr Ala Pro Thr His Tyr Asp Ser Xaa Xaa Xaa Ala
             20                  25                  30

Gly Arg Ile Val Xaa Xaa Arg
         35

<210> SEQ ID NO 361
<211> LENGTH: 42
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(42)
<223> OTHER INFORMATION: Xaa = any amino acid

<400> SEQUENCE: 361

Pro Phe Leu Ala Asp Glu Gly Xaa Gly Xaa Xaa Xaa Thr Ile Leu Val
```

```
                   1               5                  10                  15
Ala Gly Xaa Xaa Ile Leu Met Arg Arg Xaa Xaa Xaa Xaa Cys Gly Asn
                        20                  25                  30

Ser Xaa Xaa Ala Gly Ser Xaa Ala Ser Val
            35                  40

<210> SEQ ID NO 362
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid

<400> SEQUENCE: 362

Pro Xaa Xaa Xaa Gly Xaa Ala Gly Val Xaa Thr Ile Leu Val Ala Gly
 1               5                  10                  15

Xaa Xaa Ile Leu Met Arg Arg Xaa Xaa Leu Xaa Ala Cys Gly Ser Thr
                20                  25                  30

<210> SEQ ID NO 363
<211> LENGTH: 31
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(31)
<223> OTHER INFORMATION: Xaa = any amino acid

<400> SEQUENCE: 363

Pro Xaa Xaa Gly Xaa Ala Gly Val Xaa Thr Ile Leu Val Ala Gly Xaa
 1               5                  10                  15

Xaa Ile Leu Met Arg Arg Xaa Xaa Leu Xaa Ala Cys Gly Ser Thr
            20                  25                  30

<210> SEQ ID NO 364
<211> LENGTH: 31
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(31)
<223> OTHER INFORMATION: Xaa = any amino acid

<400> SEQUENCE: 364

Pro Xaa Xaa Xaa Gly Xaa Ala Gly Val Xaa Thr Ile Leu Val Ala Gly
 1               5                  10                  15

Xaa Xaa Ile Leu Met Arg Arg Xaa Leu Xaa Ala Cys Gly Ser Thr
                20                  25                  30

<210> SEQ ID NO 365
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid
```

-continued

```
<400> SEQUENCE: 365

Pro Xaa Xaa Xaa Gly Xaa Ala Gly Val Xaa Thr Ile Leu Val Ala Gly
1               5                   10                  15

Xaa Xaa Ile Leu Met Arg Arg Xaa Xaa Leu Xaa Ala Cys Gly Ser Thr
            20                  25                  30

<210> SEQ ID NO 366
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid

<400> SEQUENCE: 366

Pro Xaa Xaa Xaa Gly Xaa Xaa Xaa Thr Ile Leu Val Ala Gly Xaa Xaa
1               5                   10                  15

Ile Leu Met Arg Arg Xaa Xaa Leu Xaa Ala Cys Gly Ser Thr
            20                  25                  30

<210> SEQ ID NO 367
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 367

Pro Xaa Xaa Gly Xaa Xaa Xaa Thr Ile Leu Val Ala Gly Xaa Xaa Ile
1               5                   10                  15

Leu Met Arg Arg Xaa Xaa Leu Xaa Ala Cys Gly Ser Thr
            20                  25

<210> SEQ ID NO 368
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 368

Pro Xaa Xaa Xaa Gly Xaa Xaa Xaa Thr Ile Leu Val Ala Gly Xaa Xaa
1               5                   10                  15

Ile Leu Met Arg Arg Xaa Leu Xaa Ala Cys Gly Ser Thr
            20                  25

<210> SEQ ID NO 369
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)

<400> SEQUENCE: 369
```

Pro Xaa Xaa Gly Xaa Xaa Xaa Thr Ile Leu Val Ala Gly Xaa Xaa
1               5                   10                  15

Ile Leu Met Arg Arg Xaa Xaa Leu Xaa Ala Cys Gly Ser Thr
            20                  25                  30

<210> SEQ ID NO 370
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 370

Gly Xaa Ala Gly Val Xaa Thr Ile Leu Val Ala Gly Xaa Xaa Ile Leu
1               5                   10                  15

Met Arg Arg Xaa Xaa Leu Xaa Ala Cys Gly Ser Thr
            20                  25

<210> SEQ ID NO 371
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 371

Thr Ile Leu Val Ala Gly Xaa Xaa Ile Leu Met Arg Arg Xaa Xaa Leu
1               5                   10                  15

Xaa Ala Cys Gly Ser Thr
            20

<210> SEQ ID NO 372
<211> LENGTH: 48
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(48)
<223> OTHER INFORMATION: Xaa = any amino acid

<400> SEQUENCE: 372

Pro Xaa Leu Xaa Xaa Xaa Gly Ala Cys Gly Ser Thr Val Xaa Gly Ile
1               5                   10                  15

Ala Ser Ala Ser Val Gly Xaa Ala Ser Thr Ala Thr Xaa Ile Met Val
            20                  25                  30

Xaa Pro Ser Thr His Xaa Xaa Xaa Asp Glu Xaa Xaa Xaa Ala Gly Ser
        35                  40                  45

<210> SEQ ID NO 373
<211> LENGTH: 48
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(48)

-continued

<223> OTHER INFORMATION: Xaa = any amino acid

<400> SEQUENCE: 373

Pro Xaa Xaa Leu Xaa Xaa Gly Ala Cys Gly Ser Thr Val Xaa Gly Ile
1               5                   10                  15

Ala Ser Ala Ser Val Gly Xaa Ala Ser Thr Ala Thr Xaa Ile Met Val
            20                  25                  30

Xaa Pro Ser Thr His Xaa Xaa Xaa Asp Glu Xaa Xaa Xaa Ala Gly Ser
        35                  40                  45

<210> SEQ ID NO 374
<211> LENGTH: 49
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(49)
<223> OTHER INFORMATION: Xaa = any amino acid

<400> SEQUENCE: 374

Pro Xaa Xaa Leu Xaa Xaa Xaa Gly Ala Cys Gly Ser Thr Val Xaa Gly
1               5                   10                  15

Ile Ala Ser Ala Ser Val Gly Xaa Ala Ser Thr Ala Thr Xaa Ile Met
            20                  25                  30

Val Xaa Pro Ser Thr His Xaa Xaa Xaa Asp Glu Xaa Xaa Xaa Ala Gly
        35                  40                  45

Ser

<210> SEQ ID NO 375
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 375

Pro Xaa Ile Leu Val Phe Ile Leu Xaa Xaa Gly Xaa Gly Xaa Ile Ala
1               5                   10                  15

Ser Ala Ser Val Gly Xaa Ala Ser Thr Ala Thr Xaa Ile Met Val Xaa
            20                  25                  30

Pro Ser Thr His Xaa Xaa Xaa Asp Glu Xaa Xaa Xaa Ala Gly Ser
        35                  40                  45

<210> SEQ ID NO 376
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 376

Pro Xaa Ile Leu Val Phe Ile Leu Xaa Xaa Gly Xaa Gly Xaa Ile Ala
1               5                   10                  15

Ser Ala Ser Val Gly Xaa Ala Ser Thr Ala Thr Xaa Ile Met Val Xaa
            20                  25                  30

Pro Ser Thr His Xaa Xaa Xaa Asp Glu Xaa Xaa Xaa Ala Gly Ser
        35                  40                  45

<210> SEQ ID NO 377
<211> LENGTH: 48
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(48)
<223> OTHER INFORMATION: Xaa = any amino acid

<400> SEQUENCE: 377

Pro Xaa Ile Leu Val Phe Ile Leu Xaa Xaa Gly Xaa Xaa Gly Xaa Ile
1               5                   10                  15

Ala Ser Ala Ser Val Gly Xaa Ala Ser Thr Ala Thr Xaa Ile Met Val
            20                  25                  30

Xaa Pro Ser Thr His Xaa Xaa Xaa Asp Glu Xaa Xaa Xaa Ala Gly Ser
        35                  40                  45

<210> SEQ ID NO 378
<211> LENGTH: 46
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(46)
<223> OTHER INFORMATION: Xaa = any amino acid

<400> SEQUENCE: 378

Leu Xaa Xaa Xaa Gly Ala Cys Gly Ser Thr Val Xaa Gly Ile Ala Ser
1               5                   10                  15

Ala Ser Val Gly Xaa Ala Ser Thr Ala Thr Xaa Ile Met Val Xaa Pro
            20                  25                  30

Ser Thr His Xaa Xaa Xaa Asp Glu Xaa Xaa Xaa Ala Gly Ser
        35                  40                  45

<210> SEQ ID NO 379
<211> LENGTH: 46
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(46)
<223> OTHER INFORMATION: Xaa = any amino acid

<400> SEQUENCE: 379

Leu Xaa Xaa Xaa Gly Ala Cys Gly Ser Thr Val Xaa Gly Ile Ala Ser
1               5                   10                  15

Ala Ser Val Gly Xaa Ala Ser Thr Ala Thr Xaa Ile Met Val Xaa Pro
            20                  25                  30

Ser Thr His Xaa Xaa Xaa Asp Glu Xaa Xaa Xaa Ala Gly Ser
        35                  40                  45

<210> SEQ ID NO 380
<211> LENGTH: 34
<212> TYPE: PRT
<213> ORGANISM: Artificial Sequence
<220> FEATURE:
<223> OTHER INFORMATION: Polypeptide

```
<220> FEATURE:
<221> NAME/KEY: VARIANT
<222> LOCATION: (1)...(34)
<223> OTHER INFORMATION: Xaa = any amino acid

<400> SEQUENCE: 380

Ala Xaa Ala Ile Pro Val Xaa Xaa Xaa Asp Xaa Gly Xaa Xaa Leu Pro
  1               5                  10                  15

Ser Val Xaa Arg Xaa Ala Ile Leu Val Xaa Phe His Trp Tyr Ala Gly
             20                  25                  30

Ser Thr

<210> SEQ ID NO 381
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 381

Arg Xaa Xaa Phe Ile Leu Val Arg Xaa Xaa Xaa Xaa Gly Xaa Ile
  1               5                  10                  15

Leu Val Pro Gly Xaa Lys Xaa Xaa Ser Trp
             20                  25

<210> SEQ ID NO 382
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 382

Arg Xaa Xaa Phe Ile Leu Val Arg Xaa Xaa Xaa Xaa Gly Xaa Ile
  1               5                  10                  15

Leu Val Pro Gly Xaa Xaa Lys Xaa Ser Trp
             20                  25

<210> SEQ ID NO 383
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 383

Arg Xaa Xaa Phe Ile Leu Val Arg Xaa Xaa Xaa Xaa Gly Xaa Ile
  1               5                  10                  15

Leu Val Pro Gly Xaa Xaa Lys Xaa Xaa Ser Trp
             20                  25

<210> SEQ ID NO 384
<211> LENGTH: 19
<212> TYPE: PRT
<213> ORGANISM: Artificial Sequence
```

```
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 384

Arg Xaa Xaa Xaa Xaa Xaa Gly Xaa Ile Leu Val Pro Gly Xaa Lys Xaa
1               5                   10                  15

Xaa Ser Trp

<210> SEQ ID NO 385
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 385

Arg Xaa Xaa Xaa Xaa Xaa Gly Xaa Ile Leu Val Pro Gly Xaa Xaa Lys
1               5                   10                  15

Xaa Ser Trp

<210> SEQ ID NO 386
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 386

Arg Xaa Xaa Xaa Xaa Xaa Gly Xaa Ile Leu Val Pro Gly Xaa Xaa Lys
1               5                   10                  15

Xaa Xaa Ser Trp
            20

<210> SEQ ID NO 387
<211> LENGTH: 13
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(13)
<223> OTHER INFORMATION: Xaa = any amino acid

<400> SEQUENCE: 387

Gly Xaa Ile Leu Val Pro Gly Xaa Lys Xaa Xaa Ser Trp
1               5                   10

<210> SEQ ID NO 388
<211> LENGTH: 13
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(13)
```

<223> OTHER INFORMATION: Xaa = any amino acid

<400> SEQUENCE: 388

Gly Xaa Ile Leu Val Pro Gly Xaa Xaa Lys Xaa Ser Trp
1               5                   10

<210> SEQ ID NO 389
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 389

Gly Xaa Ile Leu Val Pro Gly Xaa Xaa Lys Xaa Xaa Ser Trp
1               5                   10

<210> SEQ ID NO 390
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 390

Gly Xaa Xaa Xaa Xaa Phe Xaa Arg Xaa Ala Gly Asn Gln Ser Thr Xaa
1               5                   10                  15

Cys Xaa Xaa Xaa Cys Ser Xaa Xaa Xaa Ala Asp Asn Gln
            20                  25

<210> SEQ ID NO 391
<211> LENGTH: 49
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(49)
<223> OTHER INFORMATION: Xaa = any amino acid

<400> SEQUENCE: 391

Glu Phe Leu Asp Pro Ser Thr Asp Glu Xaa Gln Gly Xaa Xaa Gly Xaa
1               5                   10                  15

Xaa Tyr Xaa Xaa Xaa Xaa Ala Asp Glu Gly Asn Xaa Xaa Xaa Xaa Ala
            20                  25                  30

Ile Val Ala Cys Ser Thr Xaa Xaa Xaa Xaa Asp Glu Gly Gln Xaa His
        35                  40                  45

Tyr

<210> SEQ ID NO 392
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 392

Pro Xaa Xaa Xaa Xaa Asp Pro Phe Tyr Ala Gly Leu Xaa Arg Ser Xaa
1               5                   10                  15

Ala Ser Thr Val Xaa Ala Glu Gly Thr Ala Ile Leu Val
            20                  25

<210> SEQ ID NO 393
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)
<223> OTHER INFORMATION: Xaa = any amino acid

<400> SEQUENCE: 393

Gln Gly Xaa Xaa Gly Xaa Xaa Tyr Xaa Xaa Xaa Xaa Ala Asp Glu Gly
1               5                   10                  15

Asn Xaa Xaa Xaa Xaa Ala Ile Val Ala Cys Ser Thr Xaa Xaa Xaa Xaa
            20                  25                  30

Asp Glu Gly Gln Xaa His Tyr
            35

<210> SEQ ID NO 394
<211> LENGTH: 34
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(34)
<223> OTHER INFORMATION: Xaa = any amino acid

<400> SEQUENCE: 394

Arg Leu Xaa Xaa Asp Xaa Xaa Ala Ser Thr Xaa Gly Ala Leu Val Ile
1               5                   10                  15

Leu Met Val Phe Ile Leu Val Phe Ile Leu Met Val Ser Thr Asp Asn
            20                  25                  30

Gln Thr

<210> SEQ ID NO 395
<211> LENGTH: 34
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(34)
<223> OTHER INFORMATION: Xaa = any amino acid

<400> SEQUENCE: 395

Arg Xaa Xaa Leu Asp Xaa Xaa Ala Ser Thr Xaa Gly Ala Leu Val Ile
1               5                   10                  15

Leu Met Val Phe Ile Leu Val Phe Ile Leu Met Val Ser Thr Asp Asn
            20                  25                  30

Gln Thr

<210> SEQ ID NO 396
<211> LENGTH: 36
<212> TYPE: PRT

-continued

<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(36)
<223> OTHER INFORMATION: Xaa = any amino acid

<400> SEQUENCE: 396

Arg Xaa Xaa Leu Xaa Xaa Asp Xaa Xaa Ala Ser Thr Xaa Gly Ala Leu
1               5                   10                  15

Val Ile Leu Met Val Phe Ile Leu Val Phe Ile Leu Met Val Ser Thr
            20                  25                  30

Asp Asn Gln Thr
        35

<210> SEQ ID NO 397
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid

<400> SEQUENCE: 397

Leu Asp Xaa Xaa Ala Ser Thr Xaa Gly Xaa Leu Ile Leu Met Val Phe
1               5                   10                  15

Ile Leu Val Xaa Asp Asn Gln Ser Thr Asp Asn Gln Ser Thr
            20                  25                  30

<210> SEQ ID NO 398
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 398

Gln Phe His Pro Thr Glu Lys Arg Ser Xaa Xaa Xaa Gly Xaa Xaa Phe
1               5                   10                  15

Ile Leu Met Val
            20

<210> SEQ ID NO 399
<211> LENGTH: 41
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(41)
<223> OTHER INFORMATION: Xaa = any amino acid

<400> SEQUENCE: 399

Gly Xaa Xaa Xaa Glu Xaa Ala Xaa Xaa Glu Xaa Xaa Xaa Xaa Xaa Glu
1               5                   10                  15

Xaa Xaa Xaa Ile Leu Val Xaa Asp Asn Arg Xaa Phe Ile Leu Met Val
            20                  25                  30

Xaa Xaa Xaa Xaa Phe Ile Leu Met Val

```
            35                  40

<210> SEQ ID NO 400
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 400

Glu Cys Gly Thr Val Xaa Xaa Asp Leu Xaa Gly Xaa Xaa Xaa Xaa
 1               5                  10                  15

Leu Xaa Gly

<210> SEQ ID NO 401
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 401

Glu Cys Gly Thr Val Xaa Xaa Asp Leu Xaa Xaa Gly Xaa Xaa Xaa
 1               5                  10                  15

Xaa Leu Xaa Gly
            20

<210> SEQ ID NO 402
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 402

Glu Cys Gly Thr Val Xaa Xaa Asp Leu Xaa Xaa Xaa Gly Xaa Xaa Xaa
 1               5                  10                  15

Xaa Xaa Leu Xaa Gly
                20

<210> SEQ ID NO 403
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 403

Glu Xaa Ala Xaa Xaa Glu Xaa Xaa Xaa Xaa Glu Xaa Xaa Xaa Ile
 1               5                  10                  15

Leu Val Xaa Asp Asn Arg Xaa Phe Ile Leu Met Val Xaa Xaa Xaa Xaa
                20                  25                  30
```

```
Phe Ile Leu Met Val
        35

<210> SEQ ID NO 404
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 404

Phe Xaa Xaa Glu Xaa Xaa Xaa Xaa Xaa Asp Leu Phe Ile Met Xaa Glu
 1               5                  10                  15

Xaa Ala Gly Thr Val
        20

<210> SEQ ID NO 405
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 405

Phe Xaa Xaa Xaa Xaa Glu Xaa Xaa Xaa Asp Leu Phe Ile Met Xaa Glu
 1               5                  10                  15

Xaa Ala Gly Thr Val
        20

<210> SEQ ID NO 406
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 406

Phe Xaa Xaa Xaa Xaa Glu Xaa Xaa Xaa Xaa Asp Leu Phe Ile Met
 1               5                  10                  15

Xaa Glu Xaa Ala Gly Thr Val
        20

<210> SEQ ID NO 407
<211> LENGTH: 38
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(38)
<223> OTHER INFORMATION: Xaa = any amino acid

<400> SEQUENCE: 407

Leu Xaa Xaa Leu Xaa Xaa Xaa Arg Xaa Xaa Xaa Glu Ser Thr Ile Leu
 1               5                  10                  15
```

Ser Gly Pro Gly Glu Xaa Xaa Arg Ala Ile Leu Val Xaa Ile Leu Met
            20                  25                  30

Xaa Xaa Xaa Ile Leu Val
        35

<210> SEQ ID NO 408
<211> LENGTH: 38
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(38)
<223> OTHER INFORMATION: Xaa = any amino acid

<400> SEQUENCE: 408

Leu Xaa Xaa Xaa Xaa Leu Xaa Arg Xaa Xaa Xaa Glu Ser Thr Ile Leu
1               5                   10                  15

Ser Gly Pro Gly Glu Xaa Xaa Arg Ala Ile Leu Val Xaa Ile Leu Met
            20                  25                  30

Xaa Xaa Xaa Ile Leu Val
        35

<210> SEQ ID NO 409
<211> LENGTH: 40
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(40)
<223> OTHER INFORMATION: Xaa = any amino acid

<400> SEQUENCE: 409

Leu Xaa Xaa Xaa Xaa Leu Xaa Xaa Arg Xaa Xaa Xaa Glu Ser Thr
1               5                   10                  15

Ile Leu Ser Gly Pro Gly Glu Xaa Xaa Arg Ala Ile Leu Val Xaa Ile
            20                  25                  30

Leu Met Xaa Xaa Xaa Ile Leu Val
        35                  40

<210> SEQ ID NO 410
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 410

Val Xaa Xaa Xaa Gly Ile Leu Pro Val Ala Ser Gly Ala Ser Gly Lys
1               5                   10                  15

Ser Thr Ser Thr Val Leu Ala Ile Leu
            20                  25

<210> SEQ ID NO 411
<211> LENGTH: 34
<212> TYPE: PRT
<213> ORGANISM: Artificial Sequence
<220> FEATURE:
<223> OTHER INFORMATION: Polypeptide

```
<220> FEATURE:
<221> NAME/KEY: VARIANT
<222> LOCATION: (1)...(34)
<223> OTHER INFORMATION: Xaa = any amino acid

<400> SEQUENCE: 411

Arg Xaa Ser Ile Leu Met Asn Ile Leu Val Ala Ser Xaa Ala Cys Ser
 1               5                  10                  15

Thr Ala Val Ala Cys Gly Ser Val Xaa Xaa Xaa Xaa Glu Xaa Xaa Lys
             20                  25                  30

Arg Gln

<210> SEQ ID NO 412
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 412

Leu Xaa Xaa Xaa Pro Xaa Xaa Xaa Xaa Asn Thr Val Gly Ala Asn Ser
 1               5                  10                  15

Thr Xaa Xaa Arg Xaa Ala Cys Thr
             20

<210> SEQ ID NO 413
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 413

Leu Xaa Xaa Trp Ala Xaa Glu Gln Arg Gly Xaa Leu Xaa Xaa Asn Xaa
 1               5                  10                  15

Xaa Xaa Ser Thr Thr Val
             20

<210> SEQ ID NO 414
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 414

Leu Xaa Xaa Trp Ala Xaa Glu Gln Arg Gly Xaa Xaa Leu Xaa Asn Xaa
 1               5                  10                  15

Xaa Xaa Ser Thr Thr Val
             20

<210> SEQ ID NO 415
<211> LENGTH: 23
<212> TYPE: PRT
<213> ORGANISM: Artificial Sequence
```

```
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 415

Leu Xaa Xaa Trp Ala Xaa Glu Gln Arg Gly Xaa Xaa Leu Xaa Xaa Asn
 1               5                  10                  15

Xaa Xaa Xaa Ser Thr Thr Val
             20

<210> SEQ ID NO 416
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 416

Trp Ala Xaa Glu Gln Arg Gly Xaa Leu Xaa Xaa Asn Xaa Xaa Xaa Ser
 1               5                  10                  15

Thr Thr Val

<210> SEQ ID NO 417
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 417

Trp Ala Xaa Glu Gln Arg Gly Xaa Xaa Leu Xaa Asn Xaa Xaa Xaa Ser
 1               5                  10                  15

Thr Thr Val

<210> SEQ ID NO 418
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 418

Trp Ala Xaa Glu Gln Arg Gly Xaa Xaa Leu Xaa Xaa Asn Xaa Xaa Xaa
 1               5                  10                  15

Ser Thr Thr Val
             20

<210> SEQ ID NO 419
<211> LENGTH: 14
<212> TYPE: PRT
<213> ORGANISM: Artificial Sequence
<220> FEATURE:
<223> OTHER INFORMATION: Polypeptide
```

```
<220> FEATURE:
<221> NAME/KEY: VARIANT
<222> LOCATION: (1)...(14)
<223> OTHER INFORMATION: Xaa = any amino acid

<400> SEQUENCE: 419

Ile Xaa Xaa Gly Gln Asp Pro Tyr Xaa Gly Asn Gln Ser Thr
 1               5                  10

<210> SEQ ID NO 420
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 420

Leu Xaa Ala Xaa Glu Gln Arg Gly Xaa Xaa Leu Gly Ile Leu Xaa Asn
 1               5                  10                  15

Thr Xaa Xaa Xaa Ser Thr Val
            20

<210> SEQ ID NO 421
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 421

Leu Xaa Xaa Xaa Ala Xaa Glu Gln Arg Gly Xaa Leu Gly Ile Leu Xaa
 1               5                  10                  15

Asn Thr Xaa Xaa Xaa Ser Thr Val
            20

<210> SEQ ID NO 422
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 422

Leu Xaa Xaa Xaa Ala Xaa Glu Gln Arg Gly Xaa Xaa Leu Gly Ile Leu
 1               5                  10                  15

Xaa Asn Thr Xaa Xaa Xaa Ser Thr Val
            20                  25

<210> SEQ ID NO 423
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
```

<223> OTHER INFORMATION: Xaa = any amino acid

<400> SEQUENCE: 423

Trp Ala Xaa Xaa Gly Xaa Leu Xaa Xaa Asn Xaa Xaa Xaa Ser Thr Thr
1               5                   10                  15

Val

<210> SEQ ID NO 424
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 424

Trp Ala Xaa Xaa Gly Xaa Xaa Leu Xaa Asn Xaa Xaa Xaa Ser Thr Thr
1               5                   10                  15

Val

<210> SEQ ID NO 425
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 425

Trp Ala Xaa Xaa Gly Xaa Xaa Leu Xaa Xaa Asn Xaa Xaa Xaa Ser Thr
1               5                   10                  15

Thr Val

<210> SEQ ID NO 426
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 426

Val Arg Xaa Xaa Xaa Xaa Tyr Xaa Xaa Arg Xaa Xaa Xaa Gly Lys
1               5                   10                  15

<210> SEQ ID NO 427
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 427

Val Xaa Arg Xaa Xaa Xaa Xaa Tyr Xaa Arg Xaa Xaa Xaa Gly Lys
1               5                   10                  15

```
<210> SEQ ID NO 428
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 428

Val Xaa Arg Xaa Xaa Xaa Xaa Tyr Xaa Xaa Arg Xaa Xaa Xaa Gly Lys
 1               5                  10                  15

<210> SEQ ID NO 429
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 429

Arg Xaa Xaa Xaa Xaa Xaa Tyr Ile Leu Met Arg Xaa Xaa Xaa Gly Lys
 1               5                  10                  15

<210> SEQ ID NO 430
<211> LENGTH: 59
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(59)
<223> OTHER INFORMATION: Xaa = any amino acid

<400> SEQUENCE: 430

Gly Xaa Xaa Met Glu Ala Ile Leu Val Xaa Ala Cys Gly Ser Ala Thr
 1               5                  10                  15

Val Asn Gln Ser Thr Xaa Ala Cys Gly Ser Thr Xaa Xaa Ala Asn Thr
            20                  25                  30

Val Ile Leu Val Trp Tyr Asp Met Xaa Lys Xaa Xaa Asp Glu Gln Ser
        35                  40                  45

Xaa Ala Asp Glu Gly Ser Xaa Xaa Gly Ile Val
    50                  55

<210> SEQ ID NO 431
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 431

Leu Xaa Xaa Xaa Xaa Asp Met Xaa Lys Xaa Xaa Asp Glu Gln Ser Xaa
 1               5                  10                  15

Ala Asp Glu Gly Ser Xaa Xaa Gly Ile Val
            20                  25
```

```
<210> SEQ ID NO 432
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 432

Gly Xaa Tyr Xaa Xaa Xaa Gly Xaa Ile Val Xaa Xaa Phe Leu Val Ala
 1               5                  10                  15

Asp Glu Thr Xaa Xaa Arg Xaa Xaa Gly Ile
            20                  25

<210> SEQ ID NO 433
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 433

Gly Xaa Xaa Xaa Tyr Xaa Gly Xaa Ile Val Xaa Xaa Phe Leu Val Ala
 1               5                  10                  15

Asp Glu Thr Xaa Xaa Arg Xaa Xaa Gly Ile
            20                  25

<210> SEQ ID NO 434
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 434

Gly Xaa Xaa Xaa Tyr Xaa Xaa Xaa Gly Xaa Ile Val Xaa Xaa Phe Leu
 1               5                  10                  15

Val Ala Asp Glu Thr Xaa Xaa Arg Xaa Xaa Gly Ile
            20                  25

<210> SEQ ID NO 435
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 435

Tyr Xaa Xaa Xaa Gly Xaa Ile Val Xaa Xaa Phe Leu Val Ala Asp Glu
 1               5                  10                  15

Thr Xaa Xaa Arg Xaa Xaa Gly Ile
            20
```

```
<210> SEQ ID NO 436
<211> LENGTH: 29
<212> TYPE: PRT
<213> ORGANISM: Artificial Sequence
<220> FEATURE:
<223

-continued

Xaa Xaa Xaa Xaa Ala Xaa Xaa Xaa Xaa Pro Val Phe Ile Leu Ala Gly
            20                  25                  30

Val Pro

<210> SEQ ID NO 440
<211> LENGTH: 35
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(35)
<223> OTHER INFORMATION: Xaa = any amino acid

<400> SEQUENCE: 440

Ile Ala Gly Val Xaa Ala Gly Xaa Ala Glu Ser Ala Gly Xaa Leu Xaa
1               5                   10                  15

Xaa Xaa Xaa Xaa Ala Xaa Xaa Xaa Xaa Pro Val Phe Ile Leu Ala
            20                  25                  30

Gly Val Pro
        35

<210> SEQ ID NO 441
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 441

Ala Gly Xaa Ala Glu Ser Ala Gly Xaa Leu Xaa Xaa Xaa Xaa Ala Xaa
1               5                   10                  15

Xaa Xaa Xaa Xaa Pro Val Phe Ile Leu Ala Gly Val Pro
            20                  25

<210> SEQ ID NO 442
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 442

Ala Gly Xaa Ala Glu Ser Ala Gly Xaa Leu Xaa Xaa Xaa Xaa Xaa Ala
1               5                   10                  15

Xaa Xaa Xaa Pro Val Phe Ile Leu Ala Gly Val Pro
            20                  25

<210> SEQ ID NO 443
<211> LENGTH: 30
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(30)
<223> OTHER INFORMATION: Xaa = any amino acid -continued

```
<400> SEQUENCE: 443

Ala Gly Xaa Ala Glu Ser Ala Gly Xaa Leu Xaa Xaa Xaa Xaa Xaa Ala
1               5                   10                  15

Xaa Xaa Xaa Xaa Xaa Pro Val Phe Ile Leu Ala Gly Val Pro
            20                  25                  30

<210> SEQ ID NO 444
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)
<223> OTHER INFORMATION: Xaa = any amino acid

<400> SEQUENCE: 444

Ile Xaa Xaa Ala Gly Xaa Ala Glu Ser Ala Gly Xaa Leu Xaa Xaa Xaa
1               5                   10                  15

Xaa Xaa Ala Ala Gly Asn Ser Xaa Xaa Xaa Xaa Pro Val Ile Val Xaa
            20                  25                  30

Ala Gly Val Pro Val Pro Val
            35

<210> SEQ ID NO 445
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)
<223> OTHER INFORMATION: Xaa = any amino acid

<400> SEQUENCE: 445

Ile Xaa Xaa Xaa Ala Gly Xaa Ala Glu Ser Ala Gly Xaa Leu Xaa Xaa
1               5                   10                  15

Xaa Xaa Ala Ala Gly Asn Ser Xaa Xaa Xaa Xaa Pro Val Ile Val Xaa
            20                  25                  30

Ala Gly Val Pro Val Pro Val
            35

<210> SEQ ID NO 446
<211> LENGTH: 40
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(40)
<223> OTHER INFORMATION: Xaa = any amino acid

<400> SEQUENCE: 446

Ile Xaa Xaa Xaa Ala Gly Xaa Ala Glu Ser Ala Gly Xaa Leu Xaa Xaa
1               5                   10                  15

Xaa Xaa Xaa Ala Ala Gly Asn Ser Xaa Xaa Xaa Xaa Pro Val Ile Val
            20                  25                  30

Xaa Ala Gly Val Pro Val Pro Val
            35                  40

<210> SEQ ID NO 447
<211> LENGTH: 28
```

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 447

Gly Xaa Ala Glu Ser Ala Gly Xaa Leu Xaa Xaa Xaa Xaa Ala Xaa Xaa
 1               5                  10                  15

Xaa Xaa Xaa Pro Val Phe Ile Leu Ala Gly Val Pro
            20                  25

<210> SEQ ID NO 448
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 448

Gly Xaa Ala Glu Ser Ala Gly Xaa Leu Xaa Xaa Xaa Xaa Xaa Ala Xaa
 1               5                  10                  15

Xaa Xaa Pro Val Phe Ile Leu Ala Gly Val Pro
            20                  25

<210> SEQ ID NO 449
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 449

Gly Xaa Ala Glu Ser Ala Gly Xaa Leu Xaa Xaa Xaa Xaa Xaa Ala Xaa
 1               5                  10                  15

Xaa Xaa Xaa Xaa Pro Val Phe Ile Leu Ala Gly Val Pro
            20                  25

<210> SEQ ID NO 450
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 450

Ala Xaa Xaa Xaa Xaa Xaa Pro Val Phe Ile Leu Ala Gly Val Pro
 1               5                  10                  15

<210> SEQ ID NO 451
<211> LENGTH: 28
<212> TYPE: PRT
<213> ORGANISM: Artificial Sequence
<220> FEATURE:
```

<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 451

Gly Xaa Xaa Asp Xaa Xaa Ala Gly Asn Ser Gly Ala Gly Ser Gly Xaa
1               5                   10                  15

Xaa Ala Thr Asp Ile Leu Met Xaa Ala Ser Thr Val
            20                  25

<210> SEQ ID NO 452
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 452

Gly Xaa Xaa Asp Xaa Xaa Xaa Gly Ala Gly Ser Gly Xaa Xaa Ala Thr
1               5                   10                  15

Asp Ile Leu Met Xaa Ala Ser Thr Val
            20                  25

<210> SEQ ID NO 453
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 453

Gly Xaa Asp Xaa Xaa Gly Xaa Gly Xaa Xaa Xaa Asp Ile Leu Met Xaa
1               5                   10                  15

Ala Ser Thr Val
            20

<210> SEQ ID NO 454
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (10)...(20)
<223> OTHER INFORMATION: Xaa = any amino acid

<400> SEQUENCE: 454

Gly Xaa Asp Xaa Xaa Xaa Gly Gly Xaa Xaa Xaa Asp Ile Leu Met Xaa
1               5                   10                  15

Ala Ser Thr Val
            20

<210> SEQ ID NO 455
<211> LENGTH: 21
<212> TYPE: PRT
<213> ORGANISM: Artificial Sequence
<220> FEATURE:

```
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 455

Gly Xaa Asp Xaa Xaa Xaa Gly Xaa Gly Xaa Xaa Xaa Asp Ile Leu Met
 1               5                  10                  15

Xaa Ala Ser Thr Val
             20

<210> SEQ ID NO 456
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 456

Gly Gly Xaa Gly Ser Thr Gly Ala Ser Thr Gly Ala Cys Gly Ser Ala
 1               5                  10                  15

Ser Thr Pro Xaa Phe Ile Leu Val Ala Ser Val
             20                  25

<210> SEQ ID NO 457
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 457

Gly Xaa Gly Gly Ser Thr Gly Ala Ser Thr Gly Ala Cys Gly Ser Ala
 1               5                  10                  15

Ser Thr Pro Xaa Phe Ile Leu Val Ala Ser Val
             20                  25

<210> SEQ ID NO 458
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 458

Gly Xaa Gly Xaa Gly Ser Thr Gly Ala Ser Thr Gly Ala Cys Gly Ser
 1               5                  10                  15

Ala Ser Thr Pro Xaa Phe Ile Leu Val Ala Ser Val
             20                  25

<210> SEQ ID NO 459
<211> LENGTH: 19
<212> TYPE: PRT
<213> ORGANISM: Artificial Sequence
<220> FEATURE:
```

<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 459

Gly Gly Xaa Gly Thr Gly Ala Ser Thr Ala Gly Xaa Ala Ser Thr Val
1               5                   10                  15

Ile Pro Val

<210> SEQ ID NO 460
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 460

Gly Xaa Gly Gly Thr Gly Ala Ser Thr Ala Gly Xaa Ala Ser Thr Val
1               5                   10                  15

Ile Pro Val

<210> SEQ ID NO 461
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 461

Gly Xaa Gly Xaa Gly Thr Gly Ala Ser Thr Ala Gly Xaa Ala Ser Thr
1               5                   10                  15

Val Ile Pro Val
            20

<210> SEQ ID NO 462
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 462

Asn Leu Xaa Lys Arg Gly Ala Xaa Xaa Xaa Ala Xaa Xaa Ala Cys Asn
1               5                   10                  15

Ser Xaa Asp Glu Asn Xaa Xaa Xaa Asp Gly Asn Ser
            20                  25

<210> SEQ ID NO 463
<211> LENGTH: 28
<212> TYPE: PRT
<213> ORGANISM: Artificial Sequence
<220> FEATURE:
<223> OTHER INFORMATION: Polypeptide
<220> FEATURE:

```
<221> NAME/KEY: VARIANT
<222> LOCATION: (1)...(28)
<223> OTHER INFORMATION: Xaa = any amino acid

<400> SEQUENCE: 463

Asn Leu Xaa Lys Arg Gly Xaa Ala Xaa Xaa Ala Xaa Xaa Ala Cys Asn
 1               5                  10                  15

Ser Xaa Asp Glu Asn Xaa Xaa Xaa Asp Gly Asn Ser
            20                  25

<210> SEQ ID NO 464
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 464

Asn Leu Xaa Lys Arg Gly Xaa Ala Xaa Xaa Ala Xaa Xaa Ala Cys
 1               5                  10                  15

Asn Ser Xaa Asp Glu Asn Xaa Xaa Xaa Asp Gly Asn Ser
            20                  25

<210> SEQ ID NO 465
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 465

Asp Asn Leu Gly Xaa Xaa Xaa Xaa Ala Xaa Xaa Ala Cys Asn Ser Val
 1               5                  10                  15

Xaa Cys Asn Val Xaa Xaa Xaa Asp Glu Gly Asn
            20                  25

<210> SEQ ID NO 466
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 466

Asp Asn Leu Xaa Xaa Gly Xaa Xaa Ala Xaa Xaa Ala Cys Asn Ser Val
 1               5                  10                  15

Xaa Cys Asn Val Xaa Xaa Xaa Asp Glu Gly Asn
            20                  25

<210> SEQ ID NO 467
<211> LENGTH: 29
<212> TYPE: PRT
<213> ORGANISM: Artificial Sequence
<220> FEATURE:
<223> OTHER INFORMATION: Polypeptide
<220> FEATURE:
```

```
<221> NAME/KEY: VARIANT
<222> LOCATION: (1)...(29)
<223> OTHER INFORMATION: Xaa = any amino acid

<400> SEQUENCE: 467

Asp Asn Leu Xaa Xaa Gly Xaa Xaa Xaa Ala Xaa Xaa Ala Cys Asn
 1               5                  10                  15

Ser Val Xaa Cys Asn Val Xaa Xaa Xaa Asp Glu Gly Asn
            20                  25

<210> SEQ ID NO 468
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 468

Gly Xaa Ser Phe Ile Val Ala Cys Gly Ser Thr Val Xaa Asp Asn Gly
 1               5                  10                  15

Xaa Cys Ser Leu Thr Ile Leu Val
            20

<210> SEQ ID NO 469
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 469

Gly Ala Asp Glu Ser Ser Phe Ile Val Ala Ser Xaa Ala Asp Gly Asn
 1               5                  10                  15

Gln Gly Xaa Cys Xaa Xaa Xaa Thr
            20

<210> SEQ ID NO 470
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 470

Ser Xaa Gly Xaa His Ala Ser Thr Asn Gly Xaa Ser Thr Xaa Ala Ile
 1               5                  10                  15

Val Arg Xaa Ala Ile Leu Val
            20

<210> SEQ ID NO 471
<211> LENGTH: 31
<212> TYPE: PRT
<213> ORGANISM: Artificial Sequence
<220> FEATURE:
<223> OTHER INFORMATION: Polypeptide
<220> FEATURE:
```

```
<221> NAME/KEY: VARIANT
<222> LOCATION: (1)...(31)
<223> OTHER INFORMATION: Xaa = any amino acid

<400> SEQUENCE: 471

Asn Xaa Xaa Xaa Xaa Gly Leu Pro Val Xaa Xaa Gly Phe Trp Tyr Xaa
1               5                   10                  15

Xaa Xaa Leu Met Xaa Ile Leu Met Val Xaa Xaa Xaa Xaa Phe Tyr
            20                  25                  30

<210> SEQ ID NO 472
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 472

Arg Xaa Arg Arg Xaa Cys Xaa Xaa Cys Xaa Xaa Arg Phe Tyr Gly Ser
1               5                   10                  15

Thr Thr Xaa Glu
            20

<210> SEQ ID NO 473
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 473

Arg Arg Arg Xaa Xaa Cys Xaa Xaa Cys Xaa Xaa Arg Phe Tyr Gly Ser
1               5                   10                  15

Thr Thr Xaa Glu
            20

<210> SEQ ID NO 474
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 474

Arg Xaa Arg Arg Xaa Cys Xaa Xaa Cys Xaa Xaa Arg Phe Tyr Gly Ser
1               5                   10                  15

Thr Thr Xaa Glu
            20

<210> SEQ ID NO 475
<211> LENGTH: 21
<212> TYPE: PRT
<213> ORGANISM: Artificial Sequence
<220> FEATURE:
<223> OTHER INFORMATION: Polypeptide
<220> FEATURE:
```

```
<221> NAME/KEY: VARIANT
<222> LOCATION: (1)...(21)
<223> OTHER INFORMATION: Xaa = any amino acid

<400> SEQUENCE: 475

Arg Xaa Arg Arg Xaa Xaa Cys Xaa Xaa Cys Xaa Xaa Arg Phe Tyr Gly
 1               5                  10                  15

Ser Thr Thr Xaa Glu
            20

<210> SEQ ID NO 476
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 476

Arg Arg Arg Xaa Cys Xaa Xaa Cys Xaa Xaa Arg Xaa Thr Xaa Xaa Thr
 1               5                  10                  15

Xaa Glu

<210> SEQ ID NO 477
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 477

Arg Arg Arg Xaa Cys Xaa Xaa Cys Xaa Xaa Arg Xaa Xaa Thr Thr Xaa
 1               5                  10                  15

Glu

<210> SEQ ID NO 478
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 478

Arg Arg Arg Xaa Cys Xaa Xaa Cys Xaa Xaa Arg Xaa Xaa Thr Xaa Xaa
 1               5                  10                  15

Thr Xaa Glu

<210> SEQ ID NO 479
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid
```

<400> SEQUENCE: 479

Arg Arg Arg Xaa Cys Xaa Xaa Cys Xaa Xaa Arg Xaa Xaa Thr Xaa Glu
1               5                   10                  15

<210> SEQ ID NO 480
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 480

Arg Arg Arg Xaa Xaa Cys Xaa Xaa Cys Xaa Xaa Arg Xaa Thr Xaa Glu
1               5                   10                  15

<210> SEQ ID NO 481
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 481

Arg Arg Arg Xaa Xaa Cys Xaa Xaa Cys Xaa Xaa Arg Xaa Xaa Thr Xaa
1               5                   10                  15

Glu

<210> SEQ ID NO 482
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 482

Arg Arg Xaa Cys Xaa Xaa Cys Xaa Xaa Arg Xaa Thr Xaa Xaa Thr Xaa
1               5                   10                  15

Glu

<210> SEQ ID NO 483
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 483

Arg Arg Xaa Cys Xaa Xaa Cys Xaa Xaa Arg Xaa Xaa Thr Thr Xaa Glu
1               5                   10                  15

<210> SEQ ID NO 484

```
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 484

Arg Arg Xaa Cys Xaa Xaa Cys Xaa Xaa Arg Xaa Xaa Thr Xaa Xaa Thr
1               5                   10                  15

Xaa Glu

<210> SEQ ID NO 485
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 485

Leu Xaa Xaa Xaa Cys Thr His Phe Tyr Xaa Xaa Phe Ile Leu Met Val
1               5                   10                  15

Xaa Xaa Xaa Phe Ile Leu
            20

<210> SEQ ID NO 486
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 486

Asp Gly Xaa Xaa Xaa Xaa Xaa Gly Lys Gly Ser Ser Thr Xaa Ala Cys
1               5                   10                  15

Gly Ser Thr Xaa Xaa Ile Leu Met Val Ala Gly Ser
            20                  25

<210> SEQ ID NO 487
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 487

Gly Ala Ser Thr Xaa Gly Lys Thr Xaa Thr Ala Ser Thr Val Xaa Xaa
1               5                   10                  15

Ile Leu Met Val Xaa Xaa Xaa Phe Ile Leu Met Val
            20                  25

<210> SEQ ID NO 488
<211> LENGTH: 28
```

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 488

Gly Ala Ser Thr Xaa Gly Lys Xaa Thr Thr Ala Ser Thr Val Xaa Xaa
1               5                   10                  15

Ile Leu Met Val Xaa Xaa Xaa Phe Ile Leu Met Val
            20                  25

<210> SEQ ID NO 489
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 489

Gly Ala Ser Thr Xaa Gly Lys Xaa Thr Xaa Thr Ala Ser Thr Val Xaa
1               5                   10                  15

Xaa Ile Leu Met Val Xaa Xaa Xaa Phe Ile Leu Met Val
            20                  25

<210> SEQ ID NO 490
<211> LENGTH: 41
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(41)
<223> OTHER INFORMATION: Xaa = any amino acid

<400> SEQUENCE: 490

Gly Xaa Xaa Xaa Arg Phe Ile Met Xaa Ser Xaa Xaa Xaa Lys Thr Val
1               5                   10                  15

Leu Met Xaa Xaa Ile Leu Val Xaa Asp Gly Gln Xaa Xaa Leu Met Ile
            20                  25                  30

Leu Val Xaa Xaa Xaa Phe Ile Leu Val
            35                  40

<210> SEQ ID NO 491
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 491

Gly Xaa Ser Ser Thr Asn Xaa Xaa Xaa His Xaa Xaa Ala Xaa Ala Ser
1               5                   10                  15

<210> SEQ ID NO 492
<211> LENGTH: 17
```

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 492

Glu Thr Gly Ala Gly Xaa His Trp Gly Xaa Xaa Xaa Ala Xaa Xaa Xaa
 1               5                  10                  15

Ala

<210> SEQ ID NO 493
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 493

Glu Thr Gly Ala Gly Xaa His Trp Gly Xaa Ala Xaa Xaa Xaa Ala
 1               5                  10                  15

<210> SEQ ID NO 494
<211> LENGTH: 15
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(15)
<223> OTHER INFORMATION: Xaa = any amino acid

<400> SEQUENCE: 494

Glu Thr Gly Ala Gly Xaa His Trp Gly Xaa Xaa Xaa Ala Xaa Ala
 1               5                  10                  15

<210> SEQ ID NO 495
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 495

Glu Thr Gly Ala Gly Xaa His Trp Gly Xaa Xaa Xaa Ala Xaa Xaa Xaa
 1               5                  10                  15

Ala

<210> SEQ ID NO 496
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid
```

```
<400> SEQUENCE: 496

Thr Gly Ala Gly Xaa His Trp Gly Xaa Xaa Xaa Ala Xaa Xaa Xaa Ala
1               5                   10                  15

<210> SEQ ID NO 497
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 497

Thr Gly Ala Gly Xaa His Trp Gly Xaa Ala Xaa Xaa Xaa Ala
1               5                   10

<210> SEQ ID NO 498
<211> LENGTH: 14
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(14)
<223> OTHER INFORMATION: Xaa = any amino acid

<400> SEQUENCE: 498

Thr Gly Ala Gly Xaa His Trp Gly Xaa Xaa Xaa Ala Xaa Ala
1               5                   10

<210> SEQ ID NO 499
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 499

Thr Gly Ala Gly Xaa His Trp Gly Xaa Xaa Xaa Ala Xaa Xaa Xaa Ala
1               5                   10                  15

<210> SEQ ID NO 500
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 500

Gly Xaa Xaa Xaa Ala Xaa Glu Pro Ser Thr Ala Cys Asn Ser His Ala
1               5                   10                  15

Phe Ile Leu Val Xaa Xaa Ala Leu Val
            20                  25

<210> SEQ ID NO 501
<211> LENGTH: 25
```

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 501

Gly Xaa Xaa Ala Xaa Xaa Glu Pro Ser Thr Ala Cys Asn Ser His Ala
 1               5                  10                  15

Phe Ile Leu Val Xaa Xaa Ala Leu Val
             20                  25

<210> SEQ ID NO 502
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 502

Gly Xaa Xaa Xaa Ala Xaa Glu Pro Ser Thr Ala Cys Asn Ser His Ala
 1               5                  10                  15

Phe Ile Leu Val Xaa Xaa Ala Leu Val
             20                  25

<210> SEQ ID NO 503
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 503

Gly Xaa Xaa Xaa Ala Xaa Xaa Glu Pro Ser Thr Ala Cys Asn Ser His
 1               5                  10                  15

Ala Phe Ile Leu Val Xaa Xaa Ala Leu Val
                 20                  25

<210> SEQ ID NO 504
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 504

Gly His Xaa Pro Xaa Xaa Ala Pro Xaa Xaa Pro Gly Val Xaa Ile Leu
 1               5                  10                  15

Met Xaa Glu Xaa Xaa Xaa Xaa Ala Ala Gln Ser Thr
             20                  25

<210> SEQ ID NO 505
<211> LENGTH: 27
```

```
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 505

His Xaa Pro Xaa Xaa Ala Pro Xaa Xaa Pro Gly Val Xaa Ile Leu Met
 1               5                  10                  15

Xaa Glu Xaa Xaa Xaa Xaa Ala Ala Gln Ser Thr
            20                  25

<210> SEQ ID NO 506
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 506

His Xaa Pro Xaa Xaa Xaa Xaa Pro Gly Val Xaa Ile Leu Met Xaa
 1               5                  10                  15

Glu Xaa Xaa Xaa Xaa Ala Ala Gln Ser Thr
            20                  25

<210> SEQ ID NO 507
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 507

Pro Xaa Xaa Ala Pro Xaa Xaa Pro Gly Val Xaa Ile Leu Met Xaa Glu
 1               5                  10                  15

Xaa Xaa Xaa Xaa Ala Ala Gln Ser Thr
            20                  25

<210> SEQ ID NO 508
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 508

Pro Gly Val Xaa Ile Leu Met Xaa Glu Xaa Xaa Xaa Xaa Ala Ala Gln
 1               5                  10                  15

Ser Thr

<210> SEQ ID NO 509
<211> LENGTH: 23
<212> TYPE: PRT
```

<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 509

Ser Gly Xaa Glu Xaa Ala Asn Ser Arg Phe Ile Leu Met Val Xaa Leu
1               5                   10                  15

Ala Ser Phe Ile Leu Met Val
            20

<210> SEQ ID NO 510
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 510

Ser Xaa Gly Glu Xaa Ala Asn Ser Arg Phe Ile Leu Met Val Xaa Leu
1               5                   10                  15

Ala Ser Phe Ile Leu Met Val
            20

<210> SEQ ID NO 511
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 511

Ser Xaa Gly Xaa Glu Xaa Ala Asn Ser Arg Phe Ile Leu Met Val Xaa
1               5                   10                  15

Leu Ala Ser Phe Ile Leu Met Val
            20

<210> SEQ ID NO 512
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 512

Ser Xaa Gly Xaa Glu Xaa Ala Asn Ser Arg Phe Ile Leu Met Val Xaa
1               5                   10                  15

Leu Ala Ser Phe Ile Leu Met Val
            20

<210> SEQ ID NO 513
<211> LENGTH: 24
<212> TYPE: PRT

<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 513

Ser Xaa Xaa Gly Glu Xaa Ala Asn Ser Arg Phe Ile Leu Met Val Xaa
 1               5                  10                  15

Leu Ala Ser Phe Ile Leu Met Val
            20

<210> SEQ ID NO 514
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 514

Ser Xaa Xaa Gly Xaa Glu Xaa Ala Asn Ser Arg Phe Ile Leu Met Val
 1               5                  10                  15

Xaa Leu Ala Ser Phe Ile Leu Met Val
            20                  25

<210> SEQ ID NO 515
<211> LENGTH: 44
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(44)
<223> OTHER INFORMATION: Xaa = any amino acid

<400> SEQUENCE: 515

Lys Xaa Ile Leu Pro Xaa Xaa Ala Gly Ser Gly Xaa Gly Gly Xaa Ser
 1               5                  10                  15

Ala Asp Asn Ser Thr Ala Asp Asn Xaa Ala Gly Thr Ala Gly Ser Thr
            20                  25                  30

Val Xaa Phe Leu Met Val Xaa Xaa Ile Leu Met Val
        35                  40

<210> SEQ ID NO 516
<211> LENGTH: 44
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(44)
<223> OTHER INFORMATION: Xaa = any amino acid

<400> SEQUENCE: 516

Lys Xaa Ile Leu Pro Xaa Xaa Ala Gly Ser Gly Xaa Xaa Gly Gly Ser
 1               5                  10                  15

Ala Asp Asn Ser Thr Ala Asp Asn Xaa Ala Gly Thr Ala Gly Ser Thr
            20                  25                  30

Val Xaa Phe Leu Met Val Xaa Xaa Ile Leu Met Val

-continued

```
                35                  40

<210> SEQ ID NO 517
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid

<400> SEQUENCE: 517

Lys Xaa Ile Leu Pro Xaa Xaa Ala Gly Ser Gly Xaa Xaa Gly Gly Xaa
1               5                   10                  15

Ser Ala Asp Asn Ser Thr Ala Asp Asn Xaa Ala Gly Thr Ala Gly Ser
            20                  25                  30

Thr Val Xaa Phe Leu Met Val Xaa Xaa Ile Leu Met Val
        35                  40                  45

<210> SEQ ID NO 518
<211> LENGTH: 40
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(40)
<223> OTHER INFORMATION: Xaa = any amino acid

<400> SEQUENCE: 518

Pro Xaa Xaa Ala Gly Ser Gly Xaa Gly Gly Xaa Ser Ala Asp Asn Ser
1               5                   10                  15

Thr Ala Asp Asn Xaa Ala Gly Thr Ala Gly Ser Thr Val Xaa Phe Leu
            20                  25                  30

Met Val Xaa Xaa Ile Leu Met Val
        35                  40

<210> SEQ ID NO 519
<211> LENGTH: 40
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(40)
<223> OTHER INFORMATION: Xaa = any amino acid

<400> SEQUENCE: 519

Pro Xaa Xaa Ala Gly Ser Gly Xaa Xaa Gly Gly Ser Ala Asp Asn Ser
1               5                   10                  15

Thr Ala Asp Asn Xaa Ala Gly Thr Ala Gly Ser Thr Val Xaa Phe Leu
            20                  25                  30

Met Val Xaa Xaa Ile Leu Met Val
        35                  40

<210> SEQ ID NO 520
<211> LENGTH: 41
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
```

```
<222> LOCATION: (1)...(41)
<223> OTHER INFORMATION: Xaa = any amino acid

<400> SEQUENCE: 520

Pro Xaa Xaa Ala Gly Ser Gly Xaa Xaa Gly Gly Xaa Ser Ala Asp Asn
 1               5                   10                  15

Ser Thr Ala Asp Asn Xaa Ala Gly Thr Ala Gly Ser Thr Val Xaa Phe
             20                  25                  30

Leu Met Val Xaa Xaa Ile Leu Met Val
             35                  40

<210> SEQ ID NO 521
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 521

Gly Phe Ile Leu Met Val Ala Gly Gly Gly Ser Xaa Xaa Xaa Ala Gly
 1               5                   10                  15

Ser Thr Val Xaa Ala Ile Leu Val
             20

<210> SEQ ID NO 522
<211> LENGTH: 34
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(34)
<223> OTHER INFORMATION: Xaa = any amino acid

<400> SEQUENCE: 522

Gly Xaa Gly Gly Xaa Ser Ala Asp Asn Ser Thr Ala Asp Asn Xaa Ala
 1               5                   10                  15

Gly Thr Ala Gly Ser Thr Val Xaa Phe Leu Met Val Xaa Xaa Ile Leu
             20                  25                  30

Met Val

<210> SEQ ID NO 523
<211> LENGTH: 34
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(34)
<223> OTHER INFORMATION: Xaa = any amino acid

<400> SEQUENCE: 523

Gly Xaa Xaa Gly Gly Ser Ala Asp Asn Ser Thr Ala Asp Asn Xaa Ala
 1               5                   10                  15

Gly Thr Ala Gly Ser Thr Val Xaa Phe Leu Met Val Xaa Xaa Ile Leu
             20                  25                  30

Met Val

<210> SEQ ID NO 524
```

```
<211> LENGTH: 35
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(35)
<223> OTHER INFORMATION: Xaa = any amino acid

<400> SEQUENCE: 524

Gly Xaa Xaa Gly Gly Xaa Ser Ala Asp Asn Ser Thr Ala Asp Asn Xaa
 1               5                  10                  15

Ala Gly Thr Ala Gly Ser Thr Val Xaa Phe Leu Met Val Xaa Xaa Ile
            20                  25                  30

Leu Met Val
        35

<210> SEQ ID NO 525
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid

<400> SEQUENCE: 525

Asp Ile Val Ala Ile Leu Val Ile Val Ala Cys Ser Thr Val Asp Glu
 1               5                  10                  15

Gly Phe Tyr Xaa Gly Asn Xaa Xaa Leu Lys Xaa Xaa Glu Xaa Xaa Gly
            20                  25                  30

<210> SEQ ID NO 526
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 526

Gly Phe Tyr Xaa Gly Asn Xaa Xaa Leu Lys Xaa Xaa Glu Xaa Xaa Gly
 1               5                  10                  15

<210> SEQ ID NO 527
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 527

Val Ala Cys Ser Thr Val Xaa Gly Xaa Asn Xaa Xaa Xaa Leu Lys Xaa
 1               5                  10                  15

Xaa Glu Gly Ala Gly Ser
            20

<210> SEQ ID NO 528
```

-continued

```
<211> LENGTH: 23
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 528

Val Ala Cys Ser Thr Val Xaa Gly Xaa Xaa Xaa Asn Xaa Xaa Leu Lys
1               5                   10                  15

Xaa Xaa Glu Gly Ala Gly Ser
            20

<210> SEQ ID NO 529
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 529

Val Ala Cys Ser Thr Val Xaa Gly Xaa Xaa Xaa Asn Xaa Xaa Xaa Leu
1               5                   10                  15

Lys Xaa Xaa Glu Gly Ala Gly Ser
                20

<210> SEQ ID NO 530
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(12)
<223> OTHER INFORMATION: Xaa = any amino acid

<400> SEQUENCE: 530

Gly Asn Xaa Xaa Leu Lys Xaa Xaa Glu Xaa Xaa Gly
1               5                   10

<210> SEQ ID NO 531
<211> LENGTH: 38
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(38)
<223> OTHER INFORMATION: Xaa = any amino acid

<400> SEQUENCE: 531

Gly Xaa Xaa Gly Xaa Pro Xaa Xaa Xaa Glu Gly Asn Gln Xaa Xaa
1               5                   10                  15

Xaa Xaa Ile Leu Met Xaa Xaa Asp Gly Glu Gly Phe Ile Leu Asp Ser
            20                  25                  30

Ala Ser Xaa Ala Ile Val
        35

<210> SEQ ID NO 532
```

```
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 532

Glu Arg Gly Xaa Xaa Xaa Xaa Thr Xaa Ala Ser Cys Gly Ser Thr Ala
 1               5                  10                  15

Gly Xaa Xaa Ala Gly Ser Ala Cys Ser Thr Val
            20                  25

<210> SEQ ID NO 533
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 533

Arg Gly Xaa Xaa Xaa Xaa Thr Xaa Ala Ser Cys Gly Ser Thr Ala Gly
 1               5                  10                  15

Xaa Xaa Ala Gly Ser Ala Cys Ser Thr Val
            20                  25

<210> SEQ ID NO 534
<211> LENGTH: 25
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(25)
<223> OTHER INFORMATION: Xaa = any amino acid

<400> SEQUENCE: 534

Gly Xaa Xaa Xaa Xaa Thr Xaa Ala Ser Cys Gly Ser Thr Ala Gly Xaa
 1               5                  10                  15

Xaa Ala Gly Ser Ala Cys Ser Thr Val
            20                  25

<210> SEQ ID NO 535
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 535

Thr Gly Ile Val Asn Ser Thr Ala Asp Xaa Asp Glu Arg Xaa Xaa Thr
 1               5                  10                  15

<210> SEQ ID NO 536
<211> LENGTH: 16
<212> TYPE: PRT
<213> ORGANISM: Artificial Sequence
```

```
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 536

Thr Gly Ile Val Asn Ser Thr Ala Asp Xaa Asp Glu Arg Xaa Xaa Thr
1               5                   10                  15

<210> SEQ ID NO 537
<211> LENGTH: 16
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(16)
<223> OTHER INFORMATION: Xaa = any amino acid

<400> SEQUENCE: 537

Thr Xaa Xaa Gly Ile Val Asn Ser Thr Ala Asp Xaa Asp Glu Arg Thr
1               5                   10                  15

<210> SEQ ID NO 538
<211> LENGTH: 18
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(18)
<223> OTHER INFORMATION: Xaa = any amino acid

<400> SEQUENCE: 538

Thr Xaa Xaa Gly Ile Val Asn Ser Thr Ala Asp Xaa Asp Glu Arg Xaa
1               5                   10                  15

Xaa Thr

<210> SEQ ID NO 539
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(37)
<223> OTHER INFORMATION: Xaa = any amino acid

<400> SEQUENCE: 539

Gly Xaa Xaa Xaa His Xaa Xaa Xaa Glu Ala Gly Ser Thr Xaa Xaa Lys
1               5                   10                  15

Ala Gly Ser Val Xaa Ala Gly Ser Xaa Ala Ser Thr Val Ile Leu Met
            20                  25                  30

Val Xaa Xaa Ala Cys
        35

<210> SEQ ID NO 540
<211> LENGTH: 37
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
```

<222> LOCATION: (1)...(37)
<223> OTHER INFORMATION: Xaa = any amino acid

<400> SEQUENCE: 540

Gly Xaa Xaa Xaa His Xaa Xaa Glu Ala Gly Ser Thr Xaa Xaa Lys
1               5                   10                  15

Ala Gly Ser Val Xaa Ala Gly Ser Xaa Ala Ser Thr Val Ile Leu Met
            20                  25                  30

Val Xaa Xaa Ala Cys
        35

<210> SEQ ID NO 541
<211> LENGTH: 32
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(32)
<223> OTHER INFORMATION: Xaa = any amino acid

<400> SEQUENCE: 541

Gly Tyr Xaa Arg Ile Leu Met Val Xaa Lys Arg Xaa Xaa Xaa Arg Xaa
1               5                   10                  15

Xaa Asp Gly Xaa Ala Gly Ser Thr Val Xaa Xaa Xaa Xaa Ile Leu Val
            20                  25                  30

<210> SEQ ID NO 542
<211> LENGTH: 46
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(46)
<223> OTHER INFORMATION: Xaa = any amino acid

<400> SEQUENCE: 542

Arg Xaa Asp Xaa Gln Ile Leu Xaa Gly Arg Ala Cys Ser Thr Ala Gly
1               5                   10                  15

Arg Xaa Gly Asp Xaa Gly Xaa Ala Ser Thr Xaa Phe Ile Xaa Xaa Ser
            20                  25                  30

Xaa Asp Glu Gly Gln Asp Xaa Leu Val Phe Ile Leu Met Val
        35                  40                  45

<210> SEQ ID NO 543
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 543

Arg Ile Leu Val Asp Leu Xaa Xaa Xaa Gly Arg Ala Cys Ser Thr Ala
1               5                   10                  15

Gly Arg Xaa Gly Asp Xaa Gly Xaa Ala Ser Thr Xaa Phe Ile Xaa Xaa
            20                  25                  30

Ser Xaa Asp Glu Gly Gln Asp Xaa Leu Val Phe Ile Leu Met Val
        35                  40                  45

<210> SEQ ID NO 544
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 544

Arg Ile Leu Val Asp Xaa Xaa Leu Xaa Gly Arg Ala Cys Ser Thr Ala
1               5                   10                  15

Gly Arg Xaa Gly Asp Xaa Gly Xaa Ala Ser Thr Xaa Phe Ile Xaa Xaa
            20                  25                  30

Ser Xaa Asp Glu Gly Gln Asp Xaa Leu Val Phe Ile Leu Met Val
        35                  40                  45

<210> SEQ ID NO 545
<211> LENGTH: 49
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(49)
<223> OTHER INFORMATION: Xaa = any amino acid

<400> SEQUENCE: 545

Arg Ile Leu Val Asp Xaa Xaa Leu Xaa Xaa Xaa Gly Arg Ala Cys Ser
1               5                   10                  15

Thr Ala Gly Arg Xaa Gly Asp Xaa Gly Xaa Ala Ser Thr Xaa Phe Ile
            20                  25                  30

Xaa Xaa Ser Xaa Asp Glu Gly Gln Asp Xaa Leu Val Phe Ile Leu Met
        35                  40                  45

Val

<210> SEQ ID NO 546
<211> LENGTH: 43
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(43)
<223> OTHER INFORMATION: Xaa = any amino acid

<400> SEQUENCE: 546

Asp Leu Xaa Xaa Xaa Gly Arg Ala Cys Ser Thr Ala Gly Arg Xaa Gly
1               5                   10                  15

Asp Xaa Gly Xaa Ala Ser Thr Xaa Phe Ile Xaa Xaa Ser Xaa Asp Glu
            20                  25                  30

Gly Gln Asp Xaa Leu Val Phe Ile Leu Met Val
        35                  40

<210> SEQ ID NO 547
<211> LENGTH: 43
<212> TYPE: PRT
<213> ORGANISM: Artificial Sequence
<220> FEATURE:
<223> OTHER INFORMATION: Polypeptide
<220> FEATURE:
<221> NAME/KEY: VARIANT

```
<222> LOCATION: (1)...(43)
<223> OTHER INFORMATION: Xaa = any amino acid

<400> SEQUENCE: 547

Asp Xaa Xaa Leu Xaa Gly Arg Ala Cys Ser Thr Ala Gly Arg Xaa Gly
1               5                   10                  15

Asp Xaa Gly Xaa Ala Ser Thr Xaa Phe Ile Xaa Xaa Ser Xaa Asp Glu
            20                  25                  30

Gly Gln Asp Xaa Leu Val Phe Ile Leu Met Val
        35                  40

<210> SEQ ID NO 548
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid

<400> SEQUENCE: 548

Asp Xaa Xaa Leu Xaa Xaa Xaa Gly Arg Ala Cys Ser Thr Ala Gly Arg
1               5                   10                  15

Xaa Gly Asp Xaa Gly Xaa Ala Ser Thr Xaa Phe Ile Xaa Xaa Ser Xaa
            20                  25                  30

Asp Glu Gly Gln Asp Xaa Leu Val Phe Ile Leu Met Val
        35                  40                  45

<210> SEQ ID NO 549
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid

<400> SEQUENCE: 549

Arg Xaa Xaa Leu Xaa Xaa Xaa Gly Arg Ala Cys Ser Thr Ala Gly Arg
1               5                   10                  15

Xaa Gly Asp Xaa Gly Xaa Ala Ser Thr Xaa Phe Ile Xaa Xaa Ser Xaa
            20                  25                  30

Asp Glu Gly Gln Asp Xaa Leu Val Phe Ile Leu Met Val
        35                  40                  45

<210> SEQ ID NO 550
<211> LENGTH: 45
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(45)
<223> OTHER INFORMATION: Xaa = any amino acid

<400> SEQUENCE: 550

Arg Xaa Xaa Xaa Xaa Leu Xaa Gly Arg Ala Cys Ser Thr Ala Gly Arg
1               5                   10                  15

Xaa Gly Asp Xaa Gly Xaa Ala Ser Thr Xaa Phe Ile Xaa Xaa Ser Xaa
            20                  25                  30
```

Asp Glu Gly Gln Asp Xaa Leu Val Phe Ile Leu Met Val
         35                  40                  45

<210> SEQ ID NO 551
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 551

Arg Xaa Xaa Xaa Xaa Leu Xaa Xaa Xaa Gly Arg Ala Cys Ser Thr Ala
 1               5                  10                  15

Gly Arg Xaa Gly Asp Xaa Gly Xaa Ala Ser Thr Xaa Phe Ile Xaa Xaa
             20                  25                  30

Ser Xaa Asp Glu Gly Gln Asp Xaa Leu Val Phe Ile Leu Met Val
         35                  40                  45

<210> SEQ ID NO 552
<211> LENGTH: 42
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(42)
<223> OTHER INFORMATION: Xaa = any amino acid

<400> SEQUENCE: 552

Leu Xaa Xaa Xaa Gly Arg Ala Cys Ser Thr Ala Gly Arg Xaa Gly Asp
 1               5                  10                  15

Xaa Gly Xaa Ala Ser Thr Xaa Phe Ile Xaa Xaa Ser Xaa Asp Glu Gly
             20                  25                  30

Gln Asp Xaa Leu Val Phe Ile Leu Met Val
         35                  40

<210> SEQ ID NO 553
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

<400> SEQUENCE: 553

Leu Xaa Gln Ala Ile Leu Val Ala Gly Pro Ser Thr Gly Xaa Arg Xaa
 1               5                  10                  15

Gly Val Arg

<210> SEQ ID NO 554
<211> LENGTH: 19
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(19)
<223> OTHER INFORMATION: Xaa = any amino acid

```
<400> SEQUENCE: 554

Leu Xaa Xaa Gln Ala Ile Leu Val Ala Gly Pro Ser Thr Gly Arg Xaa
 1               5                  10                  15

Gly Val Arg

<210> SEQ ID NO 555
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 555

Leu Xaa Xaa Gln Ala Ile Leu Val Ala Gly Pro Ser Thr Gly Xaa Arg
 1               5                  10                  15

Xaa Gly Val Arg
            20

<210> SEQ ID NO 556
<211> LENGTH: 67
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(67)
<223> OTHER INFORMATION: Xaa = any amino acid

<400> SEQUENCE: 556

Leu Xaa Xaa Gly Ile Leu Val Thr Glu Ala Ser Gly Xaa Xaa Xaa Xaa
 1               5                  10                  15

Ala Gly Ser Xaa Ile Val Xaa Ser Ala Ser Thr Xaa Ala Gly Ser Phe
                20                  25                  30

Ile Leu Ala Gly Ser Xaa Ile Leu Met Leu Met Xaa Xaa Gly Asn Ile
            35                  40                  45

Leu Gly Ala Asp Asn Thr Ile Leu Met Val Arg Xaa Ser Ile Leu Met
        50                  55                  60

Ala Ser Thr
65

<210> SEQ ID NO 557
<211> LENGTH: 27
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 557

Gly Cys Val Xaa Asn Ala Gly Ile Leu Pro Gly Glu Xaa Xaa Xaa Ala
 1               5                  10                  15

Ser Thr Xaa Xaa Ala Gly Xaa Ala Ser Thr Val
                20                  25

<210> SEQ ID NO 558
<211> LENGTH: 27
<212> TYPE: PRT
```

```
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(27)
<223> OTHER INFORMATION: Xaa = any amino acid

<400> SEQUENCE: 558

Gly Cys Xaa Val Asn Ala Gly Ile Leu Pro Gly Glu Xaa Xaa Xaa Ala
 1               5                  10                  15

Ser Thr Xaa Xaa Ala Gly Xaa Ala Ser Thr Val
            20                  25

<210> SEQ ID NO 559
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 559

Gly Cys Xaa Val Xaa Asn Ala Gly Ile Leu Pro Gly Glu Xaa Xaa Xaa
 1               5                  10                  15

Ala Ser Thr Xaa Xaa Ala Gly Xaa Ala Ser Thr Val
            20                  25

<210> SEQ ID NO 560
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 560

Cys Val Xaa Asn Ala Gly Ile Leu Pro Gly Glu Xaa Xaa Xaa Ala Ser
 1               5                  10                  15

Thr Xaa Xaa Ala Gly Xaa Ala Ser Thr Val
            20                  25

<210> SEQ ID NO 561
<211> LENGTH: 26
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 561

Cys Xaa Val Asn Ala Gly Ile Leu Pro Gly Glu Xaa Xaa Xaa Ala Ser
 1               5                  10                  15

Thr Xaa Xaa Ala Gly Xaa Ala Ser Thr Val
            20                  25

<210> SEQ ID NO 562
<211> LENGTH: 26
<212> TYPE: PRT
```

```
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(26)
<223> OTHER INFORMATION: Xaa = any amino acid

<400> SEQUENCE: 562

Cys Xaa Val Asn Ala Gly Ile Leu Pro Gly Glu Xaa Xaa Xaa Ala Ser
 1               5                  10                  15

Thr Xaa Xaa Ala Gly Xaa Ala Ser Thr Val
            20                  25

<210> SEQ ID NO 563
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 563

Leu Xaa Xaa Xaa Xaa Xaa Gly Ala Asp Asn Thr Ile Leu Met Val Arg
 1               5                  10                  15

Xaa Ser Ile Leu Met Ala Ser Thr
            20

<210> SEQ ID NO 564
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(22)
<223> OTHER INFORMATION: Xaa = any amino acid

<400> SEQUENCE: 564

Leu Xaa Xaa Xaa Gly Xaa Xaa Xaa Thr Ile Leu Met Val Arg Xaa Ser
 1               5                  10                  15

Ile Leu Met Ala Ser Thr
            20

<210> SEQ ID NO 565
<211> LENGTH: 21
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(21)
<223> OTHER INFORMATION: Xaa = any amino acid

<400> SEQUENCE: 565

Leu Xaa Xaa Xaa Xaa Gly Xaa Thr Ile Leu Met Val Arg Xaa Ser Ile
 1               5                  10                  15

Leu Met Ala Ser Thr
            20

<210> SEQ ID NO 566
<211> LENGTH: 23
<212> TYPE: PRT
```

<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(23)
<223> OTHER INFORMATION: Xaa = any amino acid

<400> SEQUENCE: 566

Leu Xaa Xaa Xaa Xaa Gly Xaa Xaa Xaa Thr Ile Leu Met Val Arg Xaa
 1               5                  10                  15

Ser Ile Leu Met Ala Ser Thr
            20

<210> SEQ ID NO 567
<211> LENGTH: 12
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(12)
<223> OTHER INFORMATION: Xaa = any amino acid

<400> SEQUENCE: 567

Ile Xaa Xaa Gly Ala Val Asn Xaa Gly Ser Ile Leu
 1               5                  10

<210> SEQ ID NO 568
<211> LENGTH: 42
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(42)
<223> OTHER INFORMATION: Xaa = any amino acid

<400> SEQUENCE: 568

Glu Xaa Xaa Lys Xaa Xaa Xaa Asn Xaa Ile Val Xaa Ala Asn Ser Thr
 1               5                  10                  15

Val Xaa Xaa Xaa Cys Gly Xaa Xaa Xaa Xaa Ile Pro Val Xaa Xaa Xaa
            20                  25                  30

Xaa Ala Glu Gly Asn Xaa Xaa Ile Leu Val
            35                  40

<210> SEQ ID NO 569
<211> LENGTH: 39
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(39)
<223> OTHER INFORMATION: Xaa = any amino acid

<400> SEQUENCE: 569

Gly Xaa Xaa Xaa Xaa Xaa Asp Ala Gly Thr Asp Ala Ile Pro Val Ala
 1               5                  10                  15

Ile Leu Val Xaa His Ala Ser Thr Ile Leu Val Xaa Asp Asn Ala Ser
            20                  25                  30

Xaa Xaa Gly Ser Ala Gly Val
            35

```
<210> SEQ ID NO 570
<211> LENGTH: 35
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(35)
<223> OTHER INFORMATION: Xaa = any amino acid

<400> SEQUENCE: 570

Gly Xaa Gly Xaa Asp Xaa His Xaa Phe Ile Leu Xaa Xaa Asp Glu Gly
 1               5                  10                  15

Asn Ser Xaa Xaa Xaa Xaa Ile Leu Pro Ala Cys Gly Val Gly Ile Val
            20                  25                  30

Ile Leu Val
        35

<210> SEQ ID NO 571
<211> LENGTH: 20
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(20)
<223> OTHER INFORMATION: Xaa = any amino acid

<400> SEQUENCE: 571

Glu Ala Ser Thr Val His Xaa Xaa Pro Xaa Xaa Ala Xaa Cys Ser Asp
 1               5                  10                  15

Ala Gly Asn Ser
            20

<210> SEQ ID NO 572
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(17)
<223> OTHER INFORMATION: Xaa = any amino acid

<400> SEQUENCE: 572

Glu Xaa His Xaa Xaa Pro Xaa Xaa Ala Xaa Cys Ser Asp Ala Gly Asn
 1               5                  10                  15

Ser

<210> SEQ ID NO 573
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 573

Ile Xaa Xaa Leu Val Xaa Xaa His Xaa Xaa Xaa Xaa Lys Xaa Asp Xaa
 1               5                  10                  15

Xaa Gly Ser Thr Xaa Xaa Ala Gly Phe Leu Xaa Xaa Xaa Xaa Ala Gly
            20                  25                  30
```

```
Asn Ser Xaa Arg Lys Arg Xaa Leu Met Ile Leu Xaa Phe His Tyr
        35                  40                  45
```

<210> SEQ ID NO 574
<211> LENGTH: 47
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(47)
<223> OTHER INFORMATION: Xaa = any amino acid

<400> SEQUENCE: 574

```
Ile Xaa Xaa Leu Val Xaa Xaa His Xaa Xaa Xaa Xaa Lys Asp Xaa
 1               5                  10                  15

Xaa Gly Ser Thr Xaa Xaa Ala Gly Phe Leu Xaa Xaa Xaa Ala Gly
            20                  25                  30

Asn Ser Xaa Arg Lys Arg Xaa Leu Met Ile Leu Xaa Phe His Tyr
        35                  40                  45
```

<210> SEQ ID NO 575
<211> LENGTH: 48
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(48)
<223> OTHER INFORMATION: Xaa = any amino acid

<400> SEQUENCE: 575

```
Ile Xaa Xaa Leu Val Xaa Xaa His Xaa Xaa Xaa Xaa Lys Xaa Asp
 1               5                  10                  15

Xaa Xaa Gly Ser Thr Xaa Xaa Ala Gly Phe Leu Xaa Xaa Xaa Ala
            20                  25                  30

Gly Asn Ser Xaa Arg Lys Arg Xaa Leu Met Ile Leu Xaa Phe His Tyr
        35                  40                  45
```

<210> SEQ ID NO 576
<211> LENGTH: 40
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(40)
<223> OTHER INFORMATION: Xaa = any amino acid

<400> SEQUENCE: 576

```
His Xaa Xaa Xaa Xaa Lys Xaa Asp Xaa Xaa Gly Ser Thr Xaa Xaa Ala
 1               5                  10                  15

Gly Phe Leu Xaa Xaa Xaa Xaa Ala Gly Asn Ser Xaa Arg Lys Arg Xaa
            20                  25                  30

Leu Met Ile Leu Xaa Phe His Tyr
        35                  40
```

<210> SEQ ID NO 577
<211> LENGTH: 40
<212> TYPE: PRT
<213> ORGANISM: Artificial Sequence
<220> FEATURE:
<223> OTHER INFORMATION: Polypeptide

```
<220> FEATURE:
<221> NAME/KEY: VARIANT
<222> LOCATION: (1)...(40)
<223> OTHER INFORMATION: Xaa = any amino acid

<400> SEQUENCE: 577

His Xaa Xaa Xaa Xaa Xaa Lys Asp Xaa Xaa Gly Ser Thr Xaa Xaa Ala
 1               5                  10                  15

Gly Phe Leu Xaa Xaa Xaa Xaa Ala Gly Asn Ser Xaa Arg Lys Arg Xaa
             20                  25                  30

Leu Met Ile Leu Xaa Phe His Tyr
         35                  40

<210> SEQ ID NO 578
<211> LENGTH: 41
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(41)
<223> OTHER INFORMATION: Xaa = any amino acid

<400> SEQUENCE: 578

His Xaa Xaa Xaa Xaa Xaa Lys Xaa Asp Xaa Xaa Gly Ser Thr Xaa Xaa
 1               5                  10                  15

Ala Gly Phe Leu Xaa Xaa Xaa Xaa Ala Gly Asn Ser Xaa Arg Lys Arg
             20                  25                  30

Xaa Leu Met Ile Leu Xaa Phe His Tyr
             35                  40

<210> SEQ ID NO 579
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 579

Gly Xaa Xaa Ala Asp Glu Gly Gln Ser Ala Leu Val Gln Xaa Xaa Leu
 1               5                  10                  15

Xaa Xaa Xaa Xaa Ile Xaa Xaa Leu Val Xaa Xaa His
             20                  25

<210> SEQ ID NO 580
<211> LENGTH: 28
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(28)
<223> OTHER INFORMATION: Xaa = any amino acid

<400> SEQUENCE: 580

Gly Xaa Xaa Ala Asp Glu Gly Gln Ser Ala Leu Val Gln Xaa Xaa Xaa
 1               5                  10                  15

Leu Xaa Xaa Xaa Ile Xaa Xaa Leu Val Xaa Xaa His
             20                  25
```

```
<210> SEQ ID NO 581
<211> LENGTH: 29
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(29)
<223> OTHER INFORMATION: Xaa = any amino acid

<400> SEQUENCE: 581

Gly Xaa Xaa Ala Asp Glu Gly Gln Ser Ala Leu Val Gln Xaa Xaa Xaa
 1               5                  10                  15

Leu Xaa Xaa Xaa Xaa Ile Xaa Xaa Leu Val Xaa Xaa His
            20                  25

<210> SEQ ID NO 582
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 582

Gly Xaa Xaa Glu Xaa Ala Ile Leu Pro Ile Val Ser Ser Xaa Ala Gly
 1               5                  10                  15

Thr Xaa Xaa Xaa Ala Ile Leu Val
            20

<210> SEQ ID NO 583
<211> LENGTH: 24
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (1)...(24)
<223> OTHER INFORMATION: Xaa = any amino acid

<400> SEQUENCE: 583

Gly Xaa Xaa Glu Xaa Ala Ile Leu Pro Ile Val Ser Ser Xaa Ala Gly
 1               5                  10                  15

Thr Xaa Xaa Xaa Ala Ile Leu Val
            20

<210> SEQ ID NO 584
<211> LENGTH: 8
<212> TYPE: PRT
<213> ORGANISM: Artificial Sequence
<220> FEATURE:
<223> OTHER INFORMATION: Polypeptide

<400> SEQUENCE: 584

Pro Asp Cys Gly Leu Met Lys Arg
 1               5
```